United States Patent
Kieval et al.

(10) Patent No.: US 8,755,907 B2
(45) Date of Patent: Jun. 17, 2014

(54) DEVICES AND METHODS FOR ELECTRODE IMPLANTATION

(71) Applicant: CVRx, Inc., Minneapolis, MN (US)

(72) Inventors: Robert S. Kieval, Medina, MN (US); Martin A. Rossing, Coon Rapids, MN (US)

(73) Assignee: CVRx, Inc., Minneapolis, MN (US)

( * ) Notice: Subject to any disclaimer, the term of this patent is extended or adjusted under 35 U.S.C. 154(b) by 0 days.

(21) Appl. No.: 13/898,972

(22) Filed: May 21, 2013

(65) Prior Publication Data

US 2013/0253626 A1 Sep. 26, 2013

Related U.S. Application Data

(63) Continuation of application No. 12/940,798, filed on Nov. 5, 2010, which is a continuation of application No. 12/112,899, filed on Apr. 30, 2008, now Pat. No. 8,478,414, which is a continuation of application No. 10/970,829, filed on Oct. 20, 2004, now Pat. No. 7,480,532.

(60) Provisional application No. 60/513,642, filed on Oct. 22, 2003.

(51) Int. Cl.
*A61N 1/18* (2006.01)
(52) U.S. Cl.
USPC ............ 607/118; 607/115; 607/126; 607/149
(58) Field of Classification Search
USPC .................. 607/115, 118, 126, 149
See application file for complete search history.

(56) References Cited

U.S. PATENT DOCUMENTS

| | | | |
|---|---|---|---|
| 3,522,811 A | 8/1970 | Schwartz et al. |
| 3,645,267 A | 2/1972 | Hagfors |
| 3,650,277 A | 3/1972 | Sjostrand |
| 3,943,936 A | 3/1976 | Rasor et al. |
| 4,014,318 A | 3/1977 | Dockum et al. |

(Continued)

FOREIGN PATENT DOCUMENTS

| | | |
|---|---|---|
| WO | WO97/18856 A1 | 5/1997 |
| WO | WO99/26530 A1 | 6/1999 |

(Continued)

OTHER PUBLICATIONS

Application and File History for U.S. Appl. No. 10/970,829, filed Oct. 20, 2004. Inventors: Kieval et al., now U.S. Patent No. 7,480,532.

(Continued)

*Primary Examiner* — Christopher D Koharski
*Assistant Examiner* — Natasha Patel
(74) *Attorney, Agent, or Firm* — Patterson Thuente Pedersen, P.A.

(57) ABSTRACT

Systems and methods provide baroreflex activation to treat or reduce pain and/or to cause or enhance sedation or sleep. Methods involve activating the baroreflex system to provide pain reduction, sedation, improved sleep or some combination thereof. Systems include at least one baroreflex activation device, at least one sensor for sensing physiological activity of the patient, and a processor coupled with the baroreflex activation device(s) and the sensor(s) for processing sensed data received from the sensor and for activating the baroreflex activation device. In some embodiments, the system is fully implantable within a patient, such as in an intravascular, extravascular or intramural location.

16 Claims, 29 Drawing Sheets

(56) References Cited

U.S. PATENT DOCUMENTS

| | | |
|---|---|---|
| 4,256,094 A | 3/1981 | Kapp et al. |
| 4,323,073 A | 4/1982 | Ferris |
| 4,331,157 A | 5/1982 | Keller, Jr. et al. |
| 4,481,953 A | 11/1984 | Gold et al. |
| 4,525,074 A | 6/1985 | Murakami |
| 4,531,943 A | 7/1985 | Van Tassel et al. |
| 4,551,862 A | 11/1985 | Haber |
| 4,586,501 A | 5/1986 | Claracq |
| 4,590,946 A | 5/1986 | Loeb et al. |
| 4,640,286 A | 2/1987 | Thomson |
| 4,641,664 A | 2/1987 | Botvidsson |
| 4,664,120 A | 5/1987 | Hess |
| 4,682,583 A | 7/1987 | Burton et al. |
| 4,702,254 A | 10/1987 | Zabara |
| 4,709,690 A | 12/1987 | Habor |
| 4,719,921 A | 1/1988 | Chirife |
| 4,739,762 A | 4/1988 | Palmaz |
| 4,762,130 A | 8/1988 | Fogarty et al. |
| 4,762,820 A | 8/1988 | Gavras |
| 4,770,177 A | 9/1988 | Schroeppel |
| 4,791,931 A | 12/1988 | Slate |
| 4,800,882 A | 1/1989 | Gianturco |
| 4,803,988 A | 2/1989 | Thomson |
| 4,813,418 A | 3/1989 | Harris |
| 4,825,871 A | 5/1989 | Cansell |
| 4,828,544 A | 5/1989 | Lane et al. |
| 4,830,003 A | 5/1989 | Wolff et al. |
| 4,860,751 A | 8/1989 | Callaghan |
| 4,867,164 A | 9/1989 | Zabara |
| 4,881,939 A | 11/1989 | Newman |
| 4,886,062 A | 12/1989 | Wiktor |
| 4,887,608 A | 12/1989 | Mohl et al. |
| 4,917,092 A | 4/1990 | Todd et al. |
| 4,960,133 A | 10/1990 | Hewson |
| 4,967,159 A | 10/1990 | Manes |
| 4,969,458 A | 11/1990 | Wiktor |
| 5,025,807 A | 6/1991 | Zabara |
| 5,040,533 A | 8/1991 | Fearnot |
| 5,078,736 A | 1/1992 | Behl |
| 5,113,869 A | 5/1992 | Nappholz et al. |
| 5,117,826 A | 6/1992 | Bartelt et al. |
| 5,144,960 A | 9/1992 | Mehra et al. |
| 5,170,802 A | 12/1992 | Mehra |
| 5,181,911 A | 1/1993 | Shturman |
| 5,199,428 A | 4/1993 | Obel et al. |
| 5,215,089 A | 6/1993 | Baker, Jr. |
| 5,222,971 A | 6/1993 | Willard et al. |
| 5,224,491 A | 7/1993 | Mehra |
| 5,259,394 A | 11/1993 | Bens |
| 5,282,468 A | 2/1994 | Klepinski |
| 5,295,959 A | 3/1994 | Gurbel et al. |
| 5,299,569 A | 4/1994 | Wernicke et al. |
| 5,304,206 A | 4/1994 | Baker, Jr. et al. |
| 5,314,453 A | 5/1994 | Jeutter |
| 5,318,592 A | 6/1994 | Schaldach |
| 5,330,507 A | 7/1994 | Schwartz |
| 5,330,515 A | 7/1994 | Rutecki et al. |
| 5,335,657 A | 8/1994 | Terry et al. |
| 5,351,394 A | 10/1994 | Weinberg |
| 5,411,535 A | 5/1995 | Fujii et al. |
| 5,411,540 A | 5/1995 | Edell et al. |
| 5,458,626 A | 10/1995 | Krause |
| 5,507,784 A | 4/1996 | Hill et al. |
| 5,509,888 A | 4/1996 | Miller |
| 5,522,854 A | 6/1996 | Ideker et al. |
| 5,529,067 A | 6/1996 | Larsen et al. |
| 5,531,766 A | 7/1996 | Kroll et al. |
| 5,531,779 A | 7/1996 | Dahl et al. |
| 5,535,752 A | 7/1996 | Halperin et al. |
| 5,540,734 A | 7/1996 | Zabara |
| 5,540,735 A | 7/1996 | Wingrove |
| 5,545,132 A | 8/1996 | Fagan et al. |
| 5,545,202 A | 8/1996 | Dahl et al. |
| 5,571,150 A | 11/1996 | Wernicke et al. |
| 5,575,809 A | 11/1996 | Sasaki |
| 5,578,061 A | 11/1996 | Stroetmann et al. |
| 5,634,878 A | 6/1997 | Grundei et al. |
| 5,643,330 A | 7/1997 | Holsheimer et al. |
| 5,651,378 A | 7/1997 | Matheny et al. |
| 5,662,689 A | 9/1997 | Elsberry et al. |
| 5,683,430 A | 11/1997 | Markowitz et al. |
| 5,690,681 A | 11/1997 | Geddes et al. |
| 5,692,882 A | 12/1997 | Bozeman, Jr. et al. |
| 5,695,468 A | 12/1997 | Lafontaine et al. |
| 5,700,282 A | 12/1997 | Zabara |
| 5,707,400 A | 1/1998 | Terry, Jr. et al. |
| 5,715,837 A | 2/1998 | Chen |
| 5,725,471 A | 3/1998 | Davey et al. |
| 5,725,563 A | 3/1998 | Klotz |
| 5,727,558 A | 3/1998 | Hakki et al. |
| 5,741,316 A | 4/1998 | Chen et al. |
| 5,766,236 A | 6/1998 | Detty et al. |
| 5,800,464 A | 9/1998 | Kieval |
| 5,807,258 A | 9/1998 | Cimochowski et al. |
| 5,814,079 A | 9/1998 | Kieval |
| 5,824,021 A | 10/1998 | Rise |
| 5,861,015 A | 1/1999 | Benja-Athon |
| 5,876,422 A | 3/1999 | van Groeningen |
| 5,891,181 A | 4/1999 | Zhu |
| 5,893,881 A | 4/1999 | Elsberry et al. |
| 5,913,876 A | 6/1999 | Taylor et al. |
| 5,916,239 A | 6/1999 | Geddes et al. |
| 5,919,220 A | 7/1999 | Stieglitz et al. |
| 5,928,272 A | 7/1999 | Adkins et al. |
| 5,967,986 A | 10/1999 | Cimochowski et al. |
| 5,967,989 A | 10/1999 | Cimochowski et al. |
| 5,987,352 A | 11/1999 | Klein et al. |
| 5,989,230 A | 11/1999 | Frassica |
| 6,004,269 A | 12/1999 | Crowley et al. |
| 6,006,134 A | 12/1999 | Hill et al. |
| 6,016,449 A | 1/2000 | Fischell et al. |
| 6,023,642 A | 2/2000 | Shealy et al. |
| 6,050,952 A | 4/2000 | Hakki et al. |
| 6,052,623 A | 4/2000 | Fenner et al. |
| 6,058,331 A | 5/2000 | King |
| 6,061,596 A | 5/2000 | Richmond et al. |
| 6,073,048 A | 6/2000 | Kieval et al. |
| 6,077,227 A | 6/2000 | Miesel et al. |
| 6,077,298 A | 6/2000 | Tu et al. |
| 6,128,526 A | 10/2000 | Stadler et al. |
| 6,141,588 A | 10/2000 | Cox et al. |
| 6,161,029 A | 12/2000 | Spreigl et al. |
| 6,178,349 B1 | 1/2001 | Kieval |
| 6,185,463 B1 | 2/2001 | Baudino |
| 6,206,914 B1 | 3/2001 | Soykan et al. |
| 6,208,894 B1 | 3/2001 | Schulman et al. |
| 6,231,516 B1 | 5/2001 | Keilman et al. |
| 6,292,695 B1 | 9/2001 | Webster, Jr. et al. |
| 6,292,703 B1 | 9/2001 | Meier et al. |
| 6,328,699 B1 | 12/2001 | Eigler et al. |
| 6,397,109 B1 | 5/2002 | Cammilli et al. |
| 6,438,428 B1 | 8/2002 | Axelgaard et al. |
| 6,442,413 B1 | 8/2002 | Silver |
| 6,445,953 B1 | 9/2002 | Bulkes et al. |
| 6,473,644 B1 | 10/2002 | Terry, Jr. et al. |
| 6,522,926 B1 | 2/2003 | Kieval et al. |
| 6,529,779 B1 | 3/2003 | Sutton |
| 6,564,101 B1 | 5/2003 | Zikria |
| 6,622,041 B2 | 9/2003 | Terry et al. |
| 6,821,258 B2 | 11/2004 | Reed et al. |
| 6,850,801 B2 | 2/2005 | Kieval et al. |
| 6,985,774 B2 | 1/2006 | Kieval et al. |
| 7,155,284 B1 | 12/2006 | Whitehurst et al. |
| 7,158,832 B2 | 1/2007 | Kieval et al. |
| 7,236,821 B2 | 6/2007 | Cates et al. |
| 7,480,532 B2 | 1/2009 | Kieval et al. |
| 7,499,742 B2 | 3/2009 | Bolea et al. |
| 7,502,650 B2 | 3/2009 | Kieval |
| 7,616,997 B2 | 11/2009 | Kieval et al. |
| 7,620,451 B2 | 11/2009 | Demarais et al. |
| 7,623,926 B2 | 11/2009 | Rossing et al. |
| 7,813,812 B2 | 10/2010 | Kieval et al. |
| 7,840,271 B2 | 11/2010 | Kieval et al. |
| 7,949,400 B2 | 5/2011 | Kieval et al. |

(56) References Cited

U.S. PATENT DOCUMENTS

| | | | |
|---|---|---|---|
| 8,060,206 | B2 | 11/2011 | Kieval et al. |
| 8,086,314 | B1 | 12/2011 | Kieval |
| 8,224,437 | B2 | 7/2012 | Kieval et al. |
| 8,478,414 | B2 | 7/2013 | Kieval et al. |
| 8,560,076 | B2 | 10/2013 | Kieval et al. |
| 2001/0020177 | A1 | 9/2001 | Gruzdowich et al. |
| 2002/0010461 | A1 | 1/2002 | KenKnight |
| 2002/0103516 | A1 | 8/2002 | Patwardhan et al. |
| 2002/0151051 | A1 | 10/2002 | Li |
| 2002/0151949 | A1 | 10/2002 | Dahl et al. |
| 2003/0040785 | A1 | 2/2003 | Maschino et al. |
| 2003/0060858 | A1 | 3/2003 | Kieval et al. |
| 2003/0078623 | A1 | 4/2003 | Weinberg et al. |
| 2003/0144709 | A1 | 7/2003 | Zabara et al. |
| 2004/0010303 | A1 | 1/2004 | Bolea et al. |
| 2004/0015193 | A1* | 1/2004 | Lamson et al. ............ 607/9 |
| 2004/0019364 | A1 | 1/2004 | Kieval et al. |
| 2004/0199210 | A1 | 10/2004 | Shelchuk |
| 2004/0254616 | A1 | 12/2004 | Rossing et al. |
| 2005/0154418 | A1 | 7/2005 | Kieval et al. |
| 2006/0085046 | A1 | 4/2006 | Rezai et al. |
| 2007/0203549 | A1 | 8/2007 | Demarais et al. |
| 2008/0033491 | A1 | 2/2008 | Zappala et al. |
| 2008/0132966 | A1 | 6/2008 | Levin et al. |
| 2008/0167699 | A1 | 7/2008 | Kieval et al. |
| 2008/0172104 | A1 | 7/2008 | Kieval et al. |
| 2008/0183264 | A1 | 7/2008 | Bly et al. |
| 2008/0208286 | A1 | 8/2008 | Kieval et al. |
| 2009/0030262 | A1 | 1/2009 | Kieval et al. |
| 2009/0234418 | A1 | 9/2009 | Kieval et al. |
| 2009/0275956 | A1 | 11/2009 | Burnes et al. |
| 2009/0275996 | A1 | 11/2009 | Burnes et al. |
| 2009/0276022 | A1 | 11/2009 | Burnes et al. |
| 2009/0276023 | A1 | 11/2009 | Burnes et al. |
| 2009/0276025 | A1 | 11/2009 | Burnes et al. |
| 2010/0174347 | A1 | 7/2010 | Kieval et al. |
| 2010/0179614 | A1 | 7/2010 | Kieval et al. |
| 2011/0137374 | A1 | 6/2011 | Kieval et al. |

FOREIGN PATENT DOCUMENTS

| | | | |
|---|---|---|---|
| WO | WO99/42039 | A1 | 8/1999 |
| WO | WO99/42176 | A1 | 8/1999 |
| WO | WO01/00273 | A1 | 1/2001 |
| WO | WO02/026314 | A1 | 4/2002 |
| WO | WO02/070039 | A2 | 9/2002 |
| WO | WO03/076008 | A1 | 9/2003 |
| WO | WO2008/092246 | A1 | 8/2008 |

OTHER PUBLICATIONS

Application and File History for U.S. Appl. No. 11/933,294, filed Oct. 31, 2007. Inventors: Kieval et al.

Application and File History for U.S. Appl. No. 12/112,899, filed Apr. 30, 2008. Inventors: Kieval et al.

Application and File History for U.S. Appl. No. 12/245,636, filed Oct. 3, 2008. Inventors: Kieval et al.

Application and File History for U.S. Appl. No. 12/940,798, filed Nov. 5, 2010. Inventors: Kieval et al.

Bilgutay et al., "Baropacing a New Concept in the Treatment of Hypertension," from Baroreceptors and Hypertension Proceedings of an International Symposium, pp. 425-437 (Nov. 1965).

Bilgutay et al., "Surgical Treatment of Hypertension with Reference to Baropacing," The Amer. Jour. of Cardiology, vol. 17, pp. 663-667 (May 1966).

Bock et al., "Fine Structure of Baroreceptor Terminals in the Carotid Sinus of Guinea Pigs & Mice," Cell & Tissue Research, vol. 170, pp. 95-112 (1976).

Brattstrom, Influence of Continuous and Intermittent (R-Wave Triggered) Electrical Stimulation of the Carotid Sinus Nerve on the Static Characteristic of the Circularoty Regulator, Experientia 28, pp. 414-416 (1972).

Coleridge et al., "Impulse in Slowly Conducting Vagal Fibers from Afferent Endings in the Veins Atria and Arteries of Dogs and Cats," Circ. Res., vol. 33, pp. 87-97 (Jul. 1973).

Correspondence, The New England Journal of Medicine, vol. 281, No. 2, p. 103 (Jul. 3, 1969).

Ebert et al., "Fentanyl-diazepam anesthesia with or without N20 does not attenuate cardiopulmonary baroreflex-mediated vasoconstrictor responses to controlled hypovolemia in humans," Anesth Analg, vol. 67, No. 6, pp. 548-554 (1988).

Eckberg et al., "Baroreflex Anatomy," In: Monographs of the Physiological Society (43): Human Baroreflexes in Health & Disease, Oxford, UK: Clarendon Press, pp. 19-30, (1992).

Goldberger et al., "New Technique for Vagal Nerve Stimulation," Journal of Neuroscience Methods, vol. 91, pp. 109-114 (1999).

Hainsworth, "Cardiovascular Reflexes From Ventricular & Coronary Receptors," Adv. Exp. Med. Biol., 381:157-74. (61:157-174) (1995).

Harrison, "Carotid Sinus Stimulation for the Treatment of Angina Pectoris," Official Journal of the Calif. Medical Assoc., vol. 112, No. 3, pp. 78-79 (Mar. 1970).

Itoh, "Studies on the Carotid Body & the Carotid Sinus Effects on the Heart by Electrical Stimulation of the Carotid Sinus Wall," Jap. Heart J., vol. 13, No. 2, pp. 136-149 (Mar. 1972).

Kostreva et al., "Hepatic Vein Hapatic Parenchrmal and Inferior Vena Caval Mechanoreceptors with Phrenic Afferents," Am. J. Physiol., vol. 265, pp. G15-G20 (1993).

Krauhs, "Structure of Rat Aortic Baroreceptors & Their Relationship to Connective Tissue," Journal of Neurocytology, pp. 401-414 (1979).

Lindblad et al., "Circulatory Effects of Carotid Sinus Stimulation & Changes in Blood Volume Distribution in Hypertensive Man," Acta. Physiol. Scand., 111:299-306, (Mar. 1981).

McMahon et al., "Reflex responses from the main pulmonary artery and bifurcation in anesthetized dogs" Experimental Physiology, 85, 4 pp. 411-419 (2000).

Mifflin et al. "Rapid Resetting of Low Pressure Vagal Receptors in the Superior Vena Cava of the Rat" Circ. Res vol. 51, pp. 241-249 (1982).

Neufeld, "Stimulation of the Carotid Baroreceptors Using a Radio-Frequency Method," Israel J. Med. Sci., vol. 1, No. 4, pp. 630-632 (Jul. 1965).

Peters et al., "The Principle of Electrical Carotid Sinus Nerve Stimulation: A Nerve Pacemaker System for Angina Pectoris and Hypertension Therapy," Annals of Biomedical Engineering, 8:445-458 (1980).

Peters et al., "Cardiovascular response to time delays of electrocardiogram-coupled electrical stimulation of carotid sinus nerves in dogs," Journal of the Autonomic Nervous Systems, 25:173-180, (1988).

Rau et al., "Psychophysiology of Arterial Baroreceptors and the Etiology of Hypertension," Biol. Psychol., vol. 57, pp. 179-201 (2001).

Reich, "Implantation of a Carotid Sinus Nerve Stimulator," AORN Journal, pp. 53-56, (Dec. 1969).

Richter et al., The Course of Inhibition of Sympathetic Activity during Various Patterns of Carotid Sinus Nerve Stimulation, Pflugers Arch. 317:110-123 (1970).

Schauerte et al., "Transvenous Parasympathetic Nerve Stimulation in the Inferior Vena Cava and Atrioventricular Conduction." J. Cardiovasc. Electrophysiol., 11(1):64-69 (Jan. 2000).

Sedin Gunnar, Responses of the Cardiovascular System to Carotid Sinus Nerve Stimulation, Upsala J Med Sci, 81:1-17 (1976).

Silber, "The Treatment of Heart Disease", Heart Disease, 2nd Edition, MacMillan Publishing Co., p. 1642 (1987).

Solti, "Baropacing of the Carotid Sinus Nerve for Treatment of Intractable Hypertension," Zeitschrift Fur Kardiologie, band 64 Heft 4 pp. 368-374 (1975).

Solti, "The Haemodynamic Basis of Anginal Relief Produced by Stimulation of the Carotid Sinus Nerve," Acta Medica Academiae Scientiarum Hungaricae, vol. 30 (1-2) pp. 61-65 (1973).

Stefanadis et al., "Non-Invasive Heat-Delivery to Arterial Stented Segments In Vivo: Effect of Heat on Intimal Hyperplasia" J Am Coll Cardiol, 1041-89, p. 14A (Feb. 2000).

(56) References Cited

OTHER PUBLICATIONS

Tarver et al., "Clinical Experience with a Helical Bipolar Stimulating Lead," PACE, vol. 15 Part II, pp. 1545-1556 (Oct. 1992).

Tsakiris, "Changes in Left Ventricular End Diastolic Volume Pressure Relationship After Acute Cardiac Denervation," Abstracts of the 40th Scientific Sessions, Supplement II to Circulation, vols. XXXV & XXXVI, II-253, 1 sheet (Oct. 1967).

Warzel et al., "Effects of Carotis Sinus Nerve Stimulation at Different Times in the Respiratory and Cardiac Cycles on Variability of Heart Rate and Blood Pressure of Normotensive and Renal Hypertensive Dogs," Journal of the Autonomic Nervous System, vol. 26, pp. 121-127 (1989).

Warzel et. al., "The Effect of Time of Electrical Stimulation of the Carotid Sinus on the Amount of Reduction in Arterial Pressure," Pflugers Arch., 337:39-44 (1972).

Yatteau, "Laryngospasm Induced by a Carotid-Sinus-Nerve Stimulator" The New England Journ. of Med., 284 No. 13 pp. 709-710 (1971).

* cited by examiner

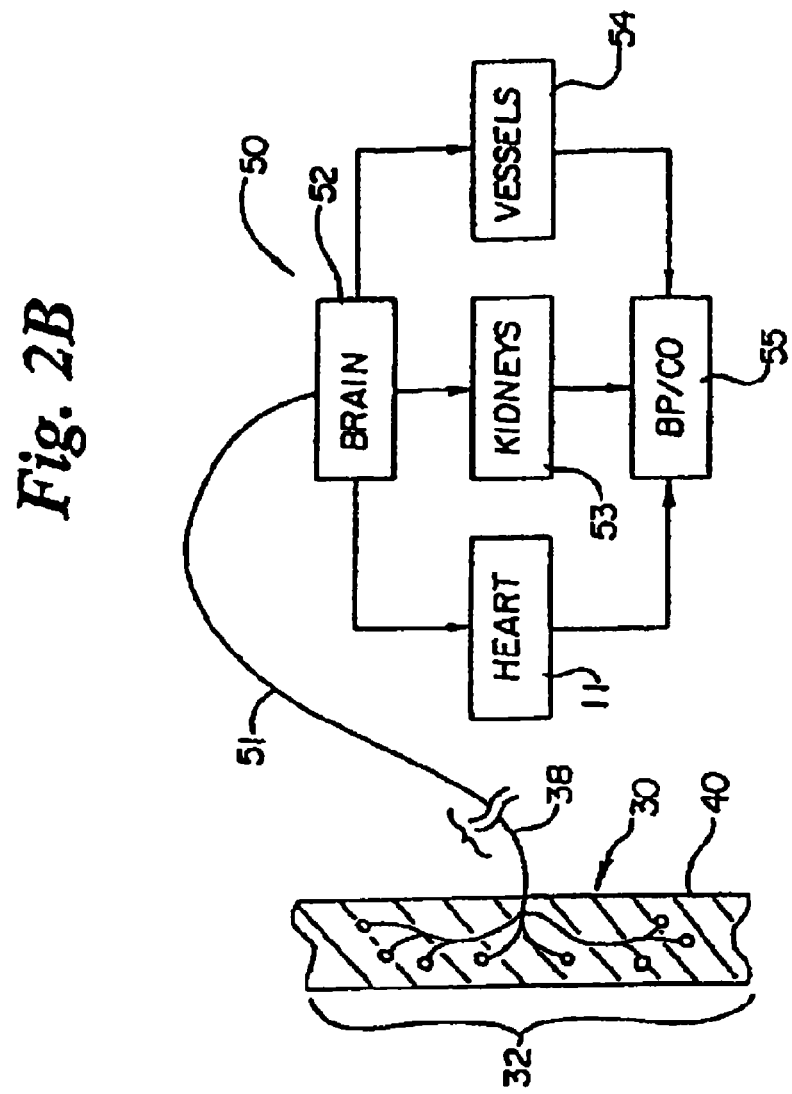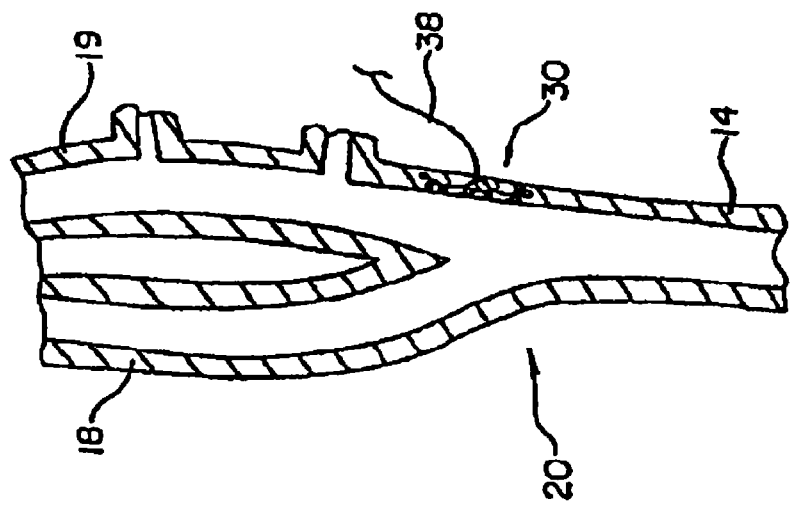

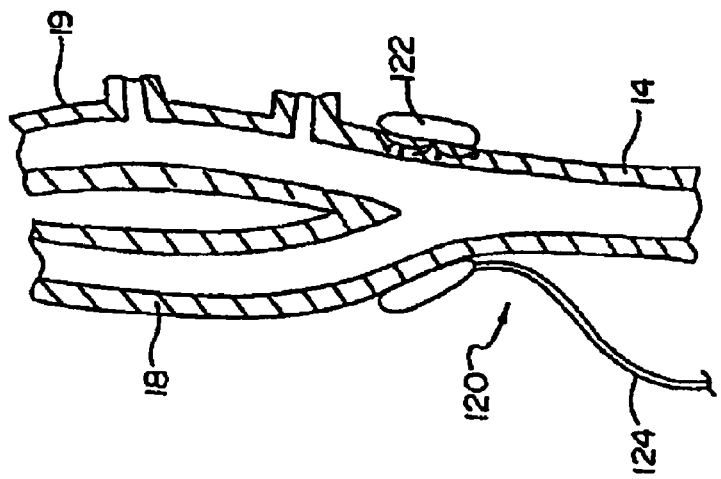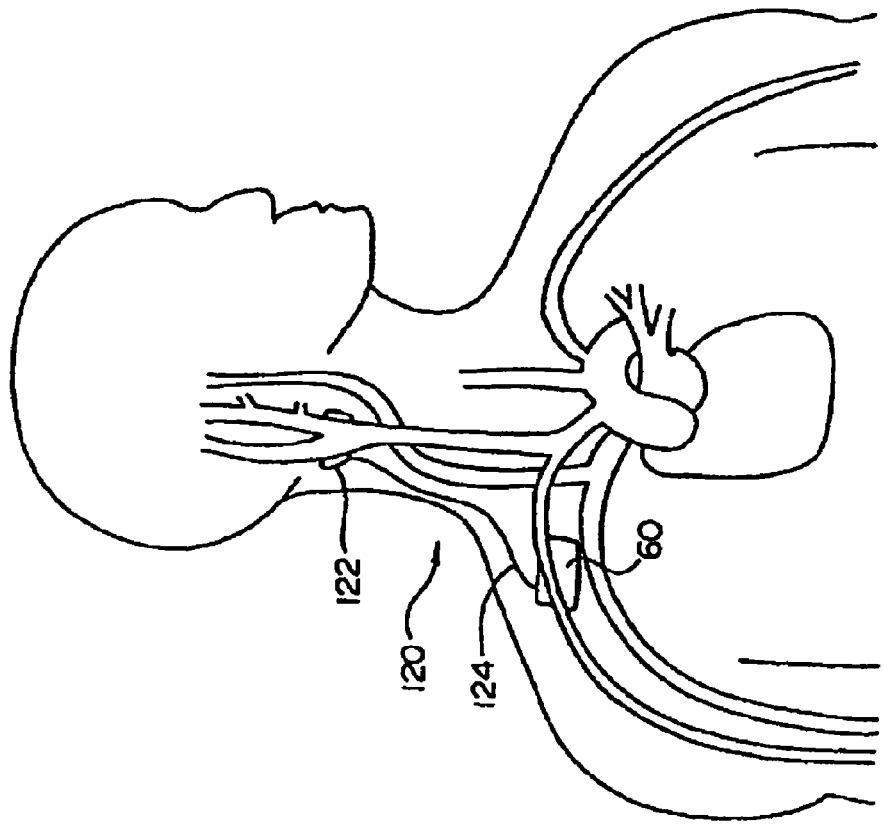

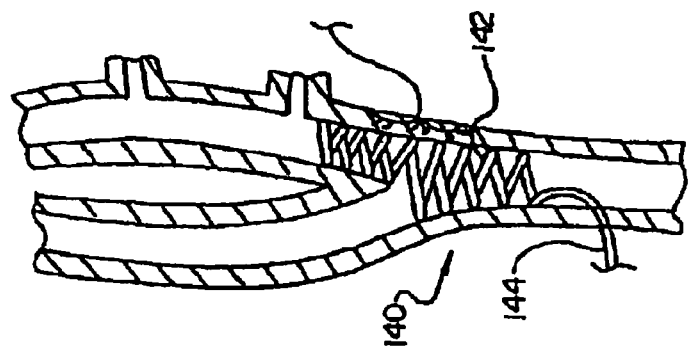
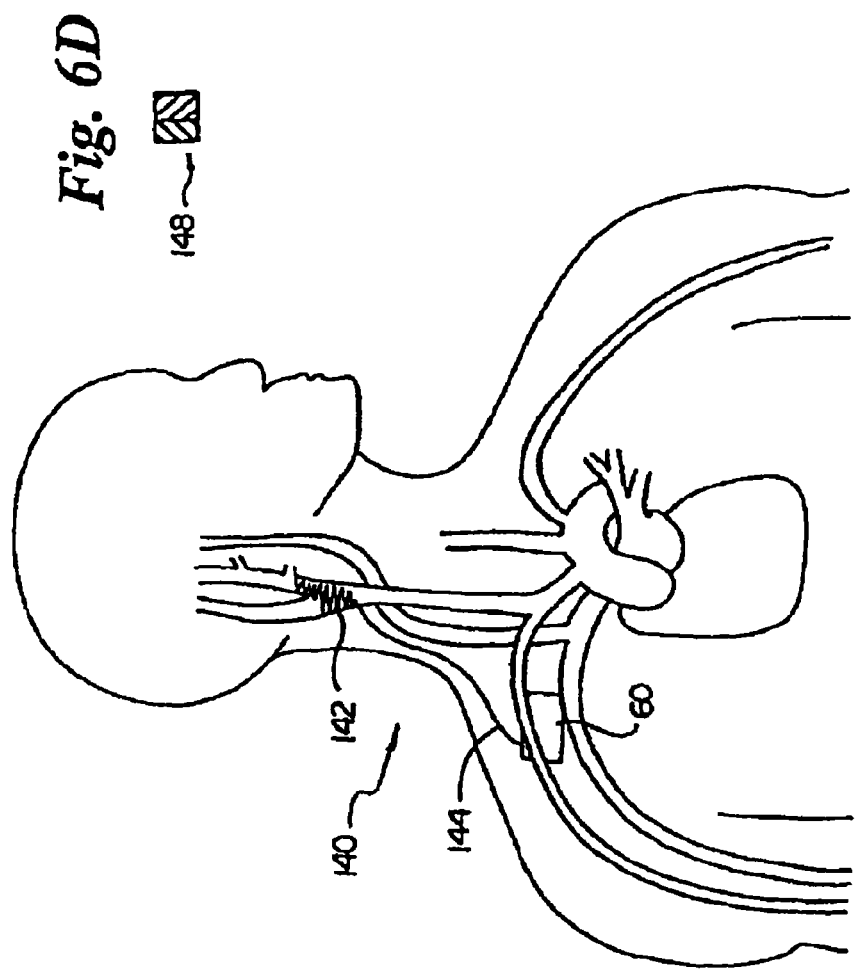

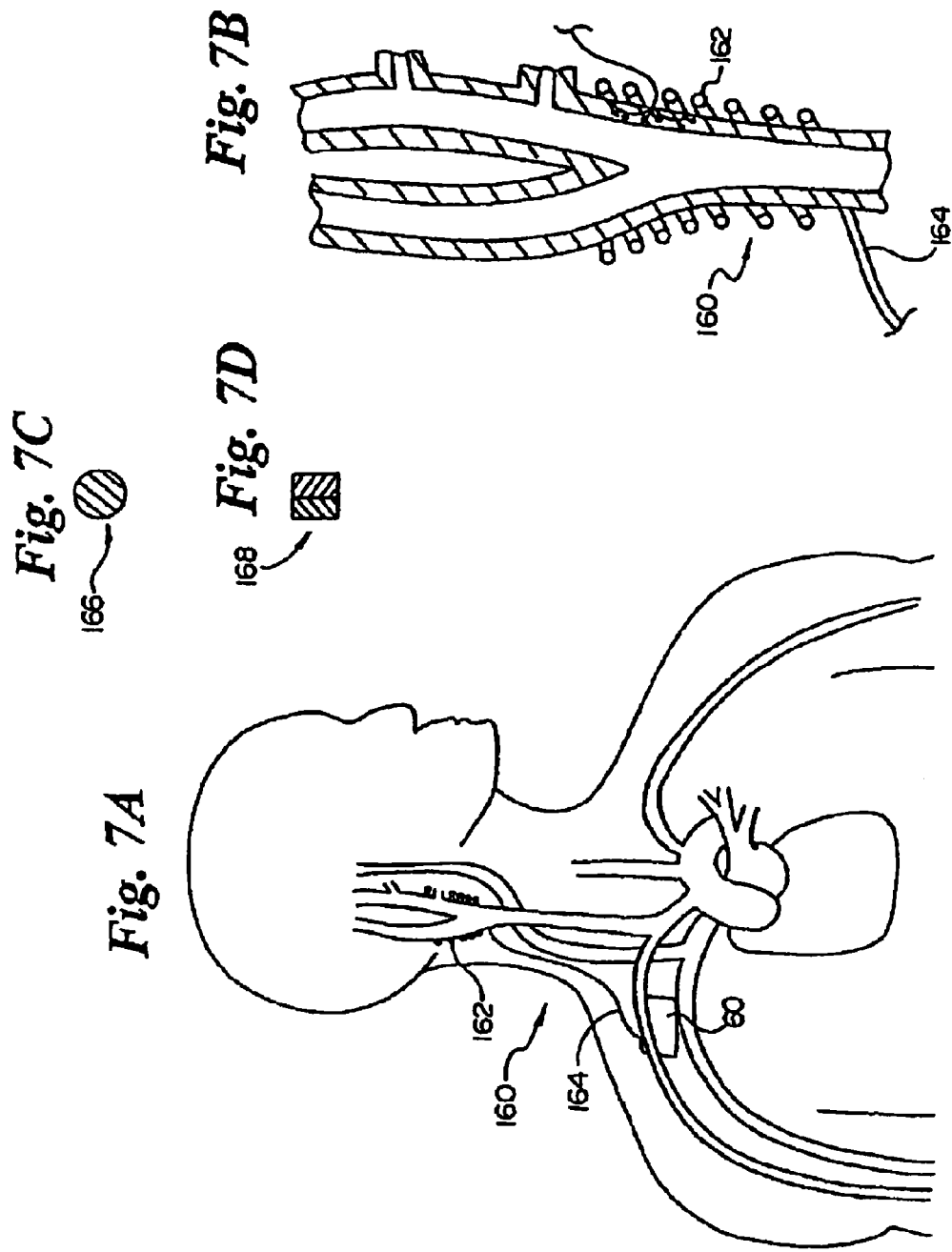

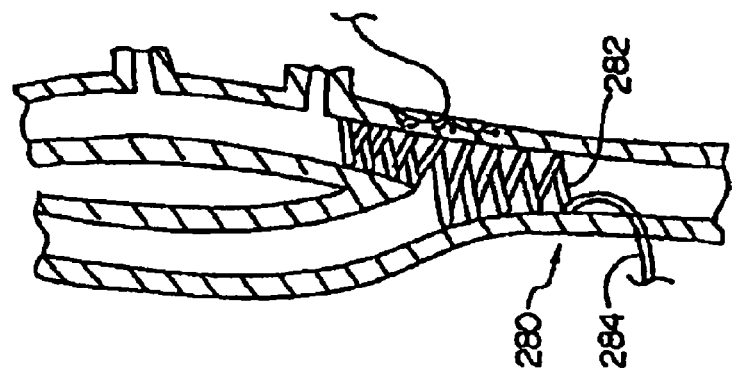
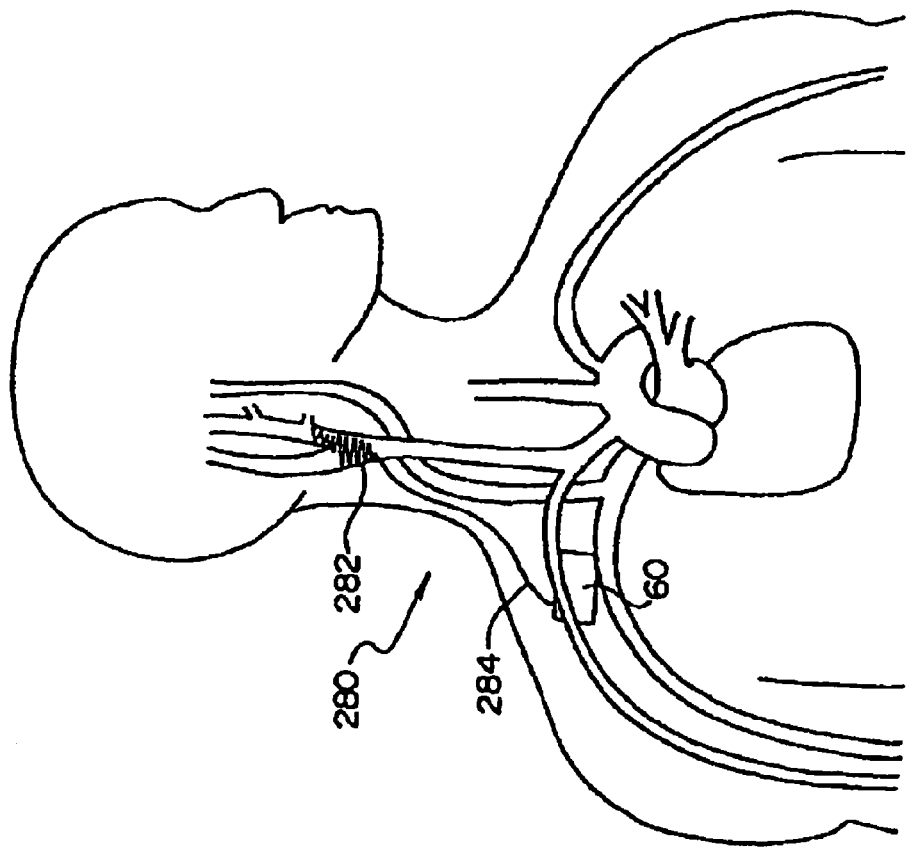

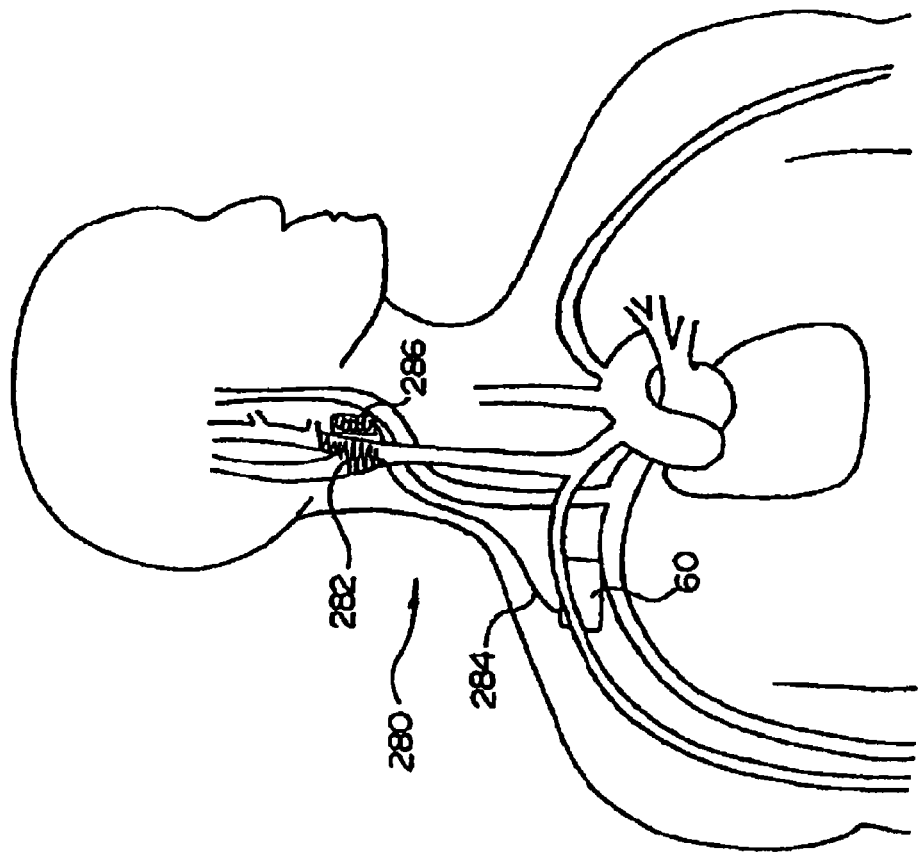
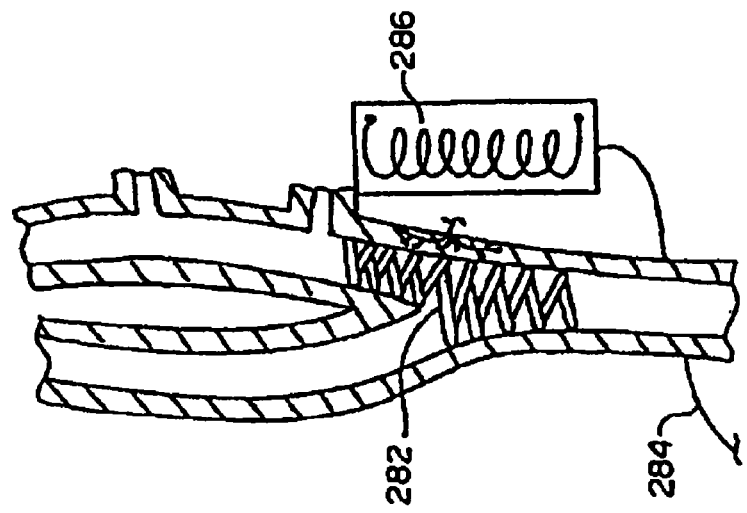
Fig. 14A
Fig. 14B

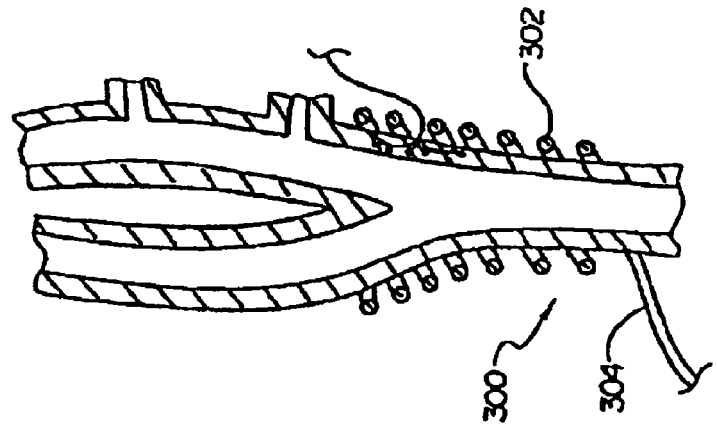
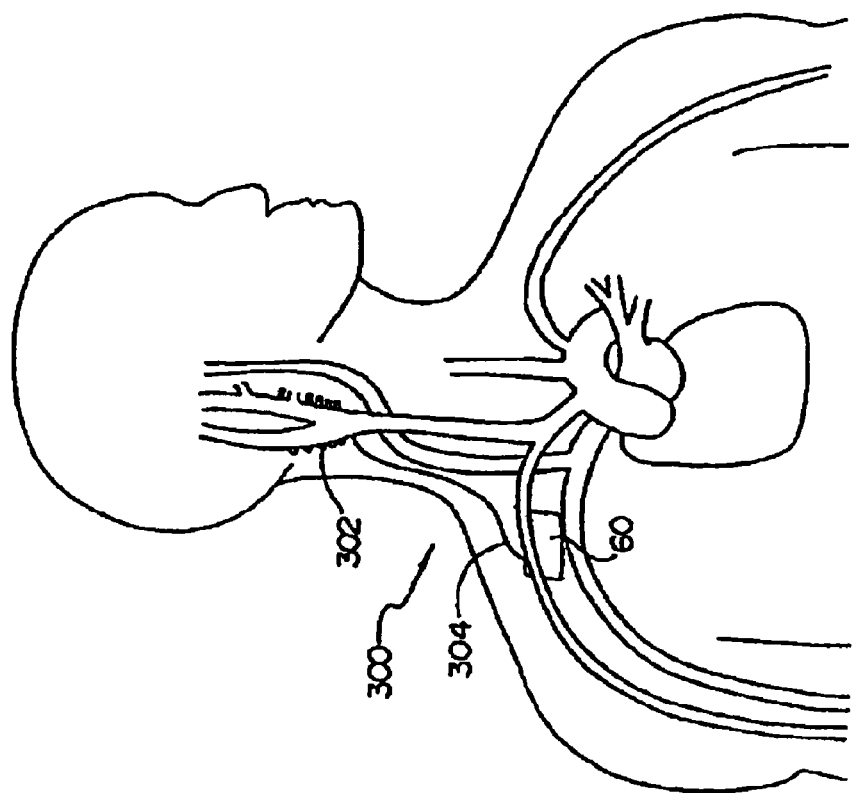
Fig. 17B
Fig. 17A

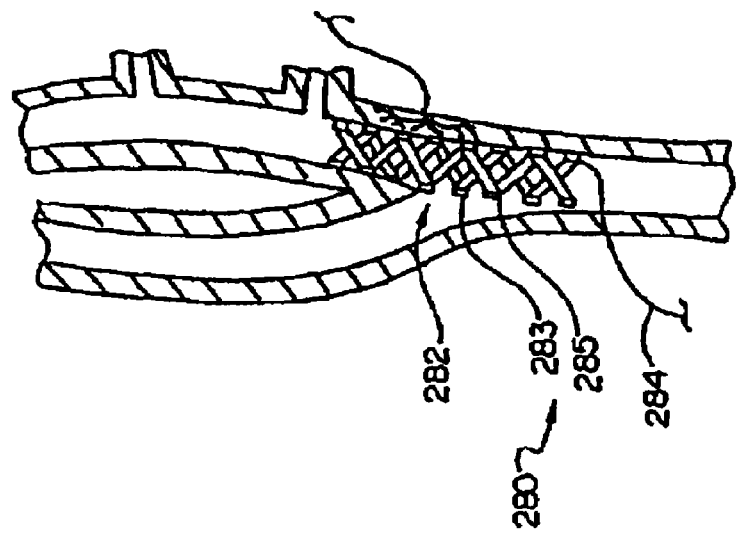
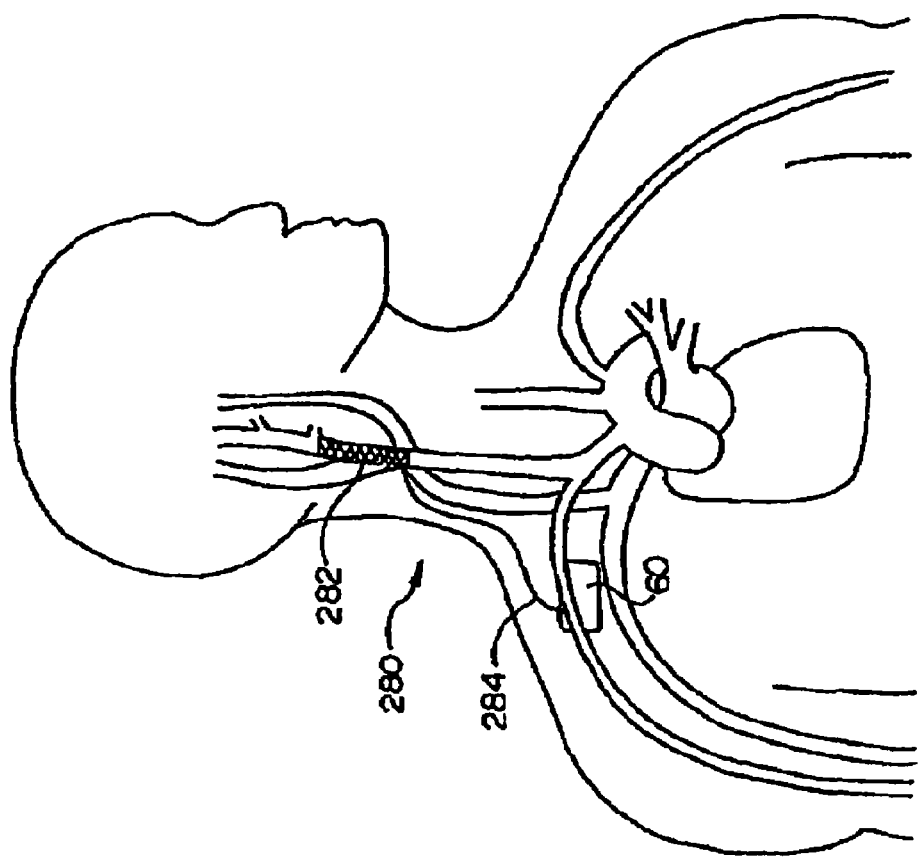

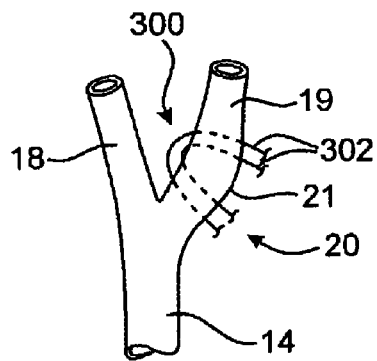
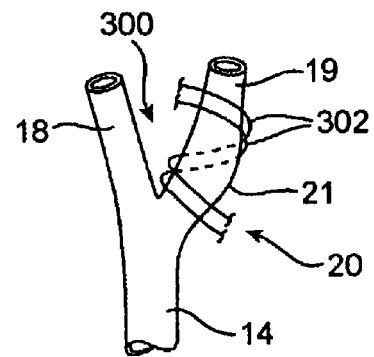
Fig. 22A     Fig. 22B
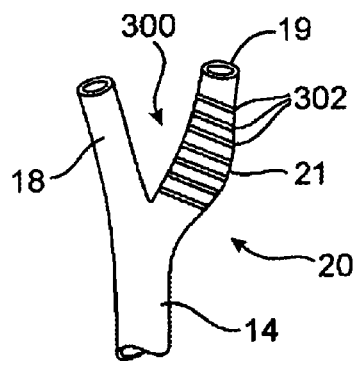
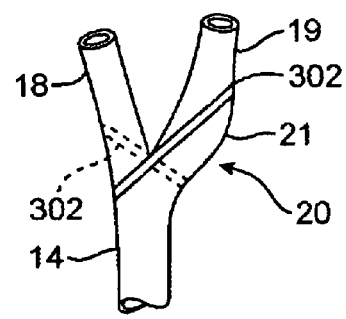
Fig. 22C     Fig. 22D

DEVICES AND METHODS FOR ELECTRODE IMPLANTATION

CROSS-REFERENCES TO RELATED APPLICATIONS

This application is a continuation of application Ser. No. 12/940,798, filed Nov. 5, 2010, which is a continuation of application Ser. No. 12/112,899, filed Apr. 30, 2008, which itself is a continuation of application Ser. No. 10/970,829, filed on Oct. 20, 2004 and now issued as U.S. Pat. No. 7,480,532, which claims the benefit of U.S. Provisional Patent Application No. 60/513,642, filed on Oct. 22, 2003, the disclosures of all of which are incorporated by reference herein. This application is related to but does not claim the benefit of: U.S. Pat. Nos. 6,522,926, 6,850,801, 6,985,774, 7,158,832, 7,499,742, 7,616,997, and 8,086,314, the disclosures of which are incorporated herein by reference.

BACKGROUND OF THE INVENTION

1. Field of the Invention

The present invention relates generally to medical devices and methods. More specifically, the invention relates to devices and methods for activating the baroreflex system to treat or reduce pain control and/or to cause or enhance sedation or sleep.

Pain is one of the oldest and least understood medical mysteries. Pain is defined by the Merriman-Webster Dictionary as: (1) localized physical suffering associated with bodily disorder, such as a disease or injury; or (2) a basic bodily sensation induced by a noxious stimulus, received by naked nerve endings, characterized by physical discomfort (as pricking, throbbing, or aching), and typically leading to evasive action. As these definitions suggest, ordinary pain is typically beneficial, in that it serves as a warning mechanism to indicate potential tissue damage. There are times, however, when it is desirable to alleviate acute pain, such as during a surgical procedure or after a trauma. Additionally, a variety of chronic pain conditions have been discovered, in which a stimulus and the pain response are not related; i.e., the pain does not serve a physiologically protective purpose and may be out of proportion with the stimulus.

It has been estimated that 10-20% of the adult population suffers from chronic pain. Chronic pathologic lesions, neurodegenerative processes, or prolonged dysfunction of parts of the peripheral or central nervous system can cause chronic pain. Chronic pain may be described as pain which persists beyond the normal healing time for a disease or injury, pain related to chronic degenerative disease or a persistent neurologic condition, pain that emerges or persists without an identifiable cause, or pain associated with cancer.

Treatment of chronic pain typically begins with prescription of non-opioid analgesics and progresses from moderate to potent opiate analgesics. If medications fail to treat the pain, more invasive techniques such as nerve stimulation, nerve ablation or even surgery are often prescribed. Although some currently available methods and devices may help to alleviate chronic pain, they often do so only partially and/or temporarily, and many treatments are burdened with significant side effects. Nonsteroidal anti-inflammatory drugs (NSAIDs), for example, may produce gastrointestinal disturbances, ulceration, renal damage, and hypersensitivity reactions. Opiate side effects include sedation, cognitive impairment, myoclonus, addiction, tolerance, respiratory depression, nausea, constipation, confusion, respiratory depression, and dependence. Nerve ablation permanently damages one or more nerves and may cause unwanted nerve damage. Surgical procedures, especially on nervous system structures such as the spinal cord, obviously have inherent risks.

In addition, current treatments are simply unable to relieve pain in many clinically severe chronic pain disorders, such as diabetic neuropathy, cervical radiculopathy, neuralgic amyotrophy, HIV neuropathy, neuralgic amyotrophy, fibromyalgia syndrome, or post herpetic neuralgia. Other chronic conditions intractable to current medical strategies are associated with both peripheral and/or central pain such as, post spinal cord injury, muscular dystrophy, trigeminal neuralgia, phantom limb pain, and diabetic and alcoholic polyneuropathies.

In treating either chronic or acute pain, it is often desirable to provide sedation and/or to help improve or induce sleep along with pain management. Although sedation and/or sleep may often play an important part in treating or at least reducing pain, it can be difficult to balance medications and other therapies to treat pain and also provide sedation or induce sleep simultaneously. Of course, it is often desirable to cause or enhance sedation or sleep outside the context of pain control, such as to provide an anti-anxiety effect, to help treat insomnia, and the like.

Rau et al., in Biological Psychology 57 (2001)179-201, reviewed several animal and human studies showing that baroreceptor activation may decrease pain perception. That article also cites early studies that have shown baroreceptor activation to cause sedation. Traditional experimental devices and methods for activating baroreceptors, however, are impractical for therapeutic use, especially long-term use. Such devices and methods include using cumbersome externally applied devices, such as a pressurized neck cuff or lateral neck suction devices, injection of pharmacological agents, and respiration techniques to affect blood pressure, such as the Valsalva maneuver. In general, these and other currently available methods and devices would not be practical for long-term or even short-term pain control, sedation or sleep enhancement in a patient.

Therefore, it would be desirable to provide improved devices and methods for treating, reducing and/or controlling pain and/or for causing or enhancing sedation or sleep. Ideally, such devices and methods would be minimally invasive and would be adaptable for treating either chronic or acute pain, with few if any significant side effects. It would also be ideal for such devices and methods to provide or enhance sedation or sleep, either along with or independent of treating pain. At least some of these objectives will be met by the present invention.

2. Description of the Background Art

Rau et al. (2001) Biological Psychology 57:179-201 describes animal and human experiments involving baroreceptor stimulation. U.S. Pat. Nos. 6,073,048 and 6,178,349, each having a common inventor with the present application, describe the stimulation of nerves to regulate the heart, vasculature, and other body systems. U.S. Pat. No. 6,522,926, assigned to the assignee of the present application, describes activation of baroreceptors by multiple modalities. Nerve stimulation for other purposes is described in, for example, U.S. Pat. Nos. 6,292,695 B1 and 5,700,282. Publications which describe the existence of baroreceptors and/or related receptors in the venous vasculature and atria include Goldberger et al. (1999) J. Neuro. Meth. 91:109-114; Kostreva and Pontus (1993) Am. J. Physiol. 265:G15-G20; Coleridge et al. (1973) Circ. Res. 23:87-97; Mifflin and Kunze (1982) Circ. Res. 51:241-249; and Schaurte et al. (2000) J. Cardiovasc Electrophysiol. 11:64-69. The full texts and disclosures of all the references listed above are hereby incorporated fully by reference.

BRIEF SUMMARY OF THE INVENTION

The present invention provides devices, systems and methods for activating the baroreflex system to treat or reduce pain and/or to improve or cause sedation or sleep. In one aspect of the present invention, a method for effecting a change in a baroreflex system of a patient to treat or reduce pain involves activating the baroreflex system of the patient with at least one baroreflex activation device. Optionally, the method may further involve implanting the baroreflex activation device in the patient. For example, in some embodiments, the device is implanted in an intravascular, extravascular and or intramural (within a vessel wall) location. In such embodiments, the method may also involve advancing the at least one baroreflex activation device through vasculature of the patient to a location for implantation. In one embodiment, for example, the device is advanced through venous vasculature of the patient. Optionally, in one embodiment, the device is advanced through a wall of the venous vasculature and is then implanted extravascularly on a wall of an artery. In various embodiments, any other suitable implantation locations and techniques may be employed.

In some embodiments, activating the baroreflex system involves activating a baroreceptor, one or more nerves coupled with a baroreceptor, a carotid sinus nerve, or some combination thereof. For example, in one embodiment, one or more baroreceptors are activated. Such baroreceptors, for example, may be located in the carotid sinus, aortic arch, heart, common carotid artery, subclavian artery, pulmonary artery, femoral artery, brachiocephalic artery and/or the like. In an alternative embodiment, such baroreceptors may be located in the inferior vena cava, superior vena cava, portal vein, jugular vein, subclavian vein, iliac vein, azygous vein, pulmonary vein, femoral vein and/or the like.

Activating the baroreflex may involve electrical activation, mechanical activation, thermal activation, chemical activation, some combination thereof, or any other suitable type of activation. In various embodiments, activation may be either continuous, pulsed or periodic. In one embodiment, activating the baroreflex system not only treats or reduces pain but also causes sedation of the patient.

Optionally, the method may also include sensing a patient condition indicative of pain with one or more sensor devices and initiating or modifying baroreflex activation in response to the sensed patient condition. For example, sensing the patient condition may involve sensing physiological activity, neurological activity or both. Alternatively, in some embodiments, activating the baroreflex is controlled by the patient.

In another aspect of the present invention, a method for effecting a change in a baroreflex system of a patient to cause or enhance sedation or sleep involves activating the baroreflex system of the patient with at least one baroreflex activation device. Any of the various features of the methods described above may also be applied to this aspect of the invention. Additionally, in some embodiments, baroreflex activation is tailored to match the sleep/wake patterns of the patient. For example, in various embodiments, activation may start at a specified time each day, end at a specified time each day and/or have a duration lasting for a specified amount of time each day.

In some embodiments, especially when directed at improving sleep, the method may include sensing a patient condition with one or more sensor devices and initiating or modifying baroreflex activation in response to the sensed patient condition. For example, sensing the patient condition may involve sensing a physiological activity and/or body position indicative of sleep or pre-sleep behavior of the patient. For example, a sensor may detect that a patient has been lying down for a certain amount of time and may help induce sleep based on that body position. In some embodiments, the method involves sensing via a remote sensor separated from the patient, while alternative embodiments involve sensing with one or more sensors in a bed. Any of a number of other methods for sensing may be used. In another embodiment, sensing the patient condition involves sensing a physiological activity and/or body position indicative of awakening or pre-awakening behavior of the patient. Alternatively, sensing the patient condition may involve learning a behavior pattern of the patient, such that initiating or modifying the baroreflex activation occurs before the patient goes to sleep each day. In another embodiment, the initiation or modification of baroreflex activation is based at least in part on the time of day. In these or other embodiments, baroreflex activation may additionally or alternatively be controllable by the patient.

In another aspect of the present invention, a system for effecting a change in a baroreflex system of a patient to treat or reduce pain and/or cause or enhance sedation or sleep includes at least one baroreflex activation device, at least one sensor for sensing physiological activity of the patient, and a processor coupled with the at least one baroreflex activation device and the at least one sensor for processing sensed data received from the sensor and for activating the baroreflex activation device. In some embodiments, the system is fully implantable within the patient. For example, the system may be implantable in an intravascular, extravascular or intramural location.

In some embodiments, the baroreflex activation device is adapted to activate a baroreceptor, one or more nerves coupled with a baroreceptor and/or a carotid sinus nerve. The baroreflex activation device may adapt to provide electrical activation, mechanical activation, thermal activation, chemical activation and/or the like. In various embodiments, the baroreflex activation device is adapted to provide continuous activation, pulsed activation, periodic activation, or some combination thereof. In some embodiments, the system is adapted to activate the baroreflex system at a specified time each day. The system may optionally be further adapted to activate the baroreflex system for a specified duration of time each day.

In various embodiments, the sensor(s) are adapted to sense physiological activity and/or body position indicative of sleep or pre-sleep behavior of the patient. Alternatively, or additionally, the sensor(s) may be adapted to sense physiological activity and/or neurological activity indicative of pain. In some embodiments, the processor is adapted to learn a behavior pattern of the patient, such that initiating or modifying the baroreflex activation occurs before the patient goes to sleep each day. Alternatively, or additionally, the processor may be adapted to accept input from the patient to allow the patient to activate the baroreflex activation.

These and other aspects and embodiments of the present invention will be described in further detail below, with reference to the attached drawing figures.

BRIEF DESCRIPTION OF THE DRAWINGS

FIG. 2A is a cross sectional schematic illustration of the carotid sinus and baroreceptors within the vascular wall;

FIG. 2B is a schematic illustration of baroreceptors within the vascular wall and the baroreflex system;

FIGS. 5A and 5B are schematic illustrations of a baroreflex activation device in the form of an external pressure cuff which mechanically induces a baroreceptor signal in accordance with an embodiment of the present invention;

FIGS. 6A and 6B are schematic illustrations of a baroreflex activation device in the form of an internal deform able coil structure which mechanically induces a baroreceptor signal in accordance with an embodiment of the present invention;

FIGS. 6C and 6D are cross sectional views of alternative embodiments of the coil member illustrated in FIGS. 6A and 6B;

FIGS. 7A and 7B are schematic illustrations of a baroreflex activation device in the form of an external deformable coil structure which mechanically induces a baroreceptor signal in accordance with an embodiment of the present invention;

FIGS. 7C and 7D are cross sectional views of alternative embodiments of the coil member illustrated in FIGS. 7A and 7B;

FIGS. 13A and 13B are schematic illustrations of a baroreflex activation device in the form of an internal conductive structure which electrically or thermally induces a baroreceptor signal in accordance with an embodiment of the present invention;

FIGS. 14A and 14B are schematic illustrations of a baroreflex activation device in the form of an internal conductive structure, activated by an internal inductor, which electrically or thermally induces a baroreceptor signal in accordance with an embodiment of the present invention;

FIGS. 17A and 17B are schematic illustrations of a baroreflex activation device in the form of an external conductive structure which electrically or thermally induces a baroreceptor signal in accordance with an embodiment of the present invention;

FIGS. 18A and 18B are schematic illustrations of a baroreflex activation device in the form of an internal bipolar conductive structure which electrically or thermally induces a baroreceptor signal in accordance with an embodiment of the present invention;

FIGS. 22A-22F are schematic illustrations of various possible arrangements of electrodes around the carotid sinus for extravascular electrical activation embodiments;

DETAILED DESCRIPTION OF THE INVENTION

Figure 1:
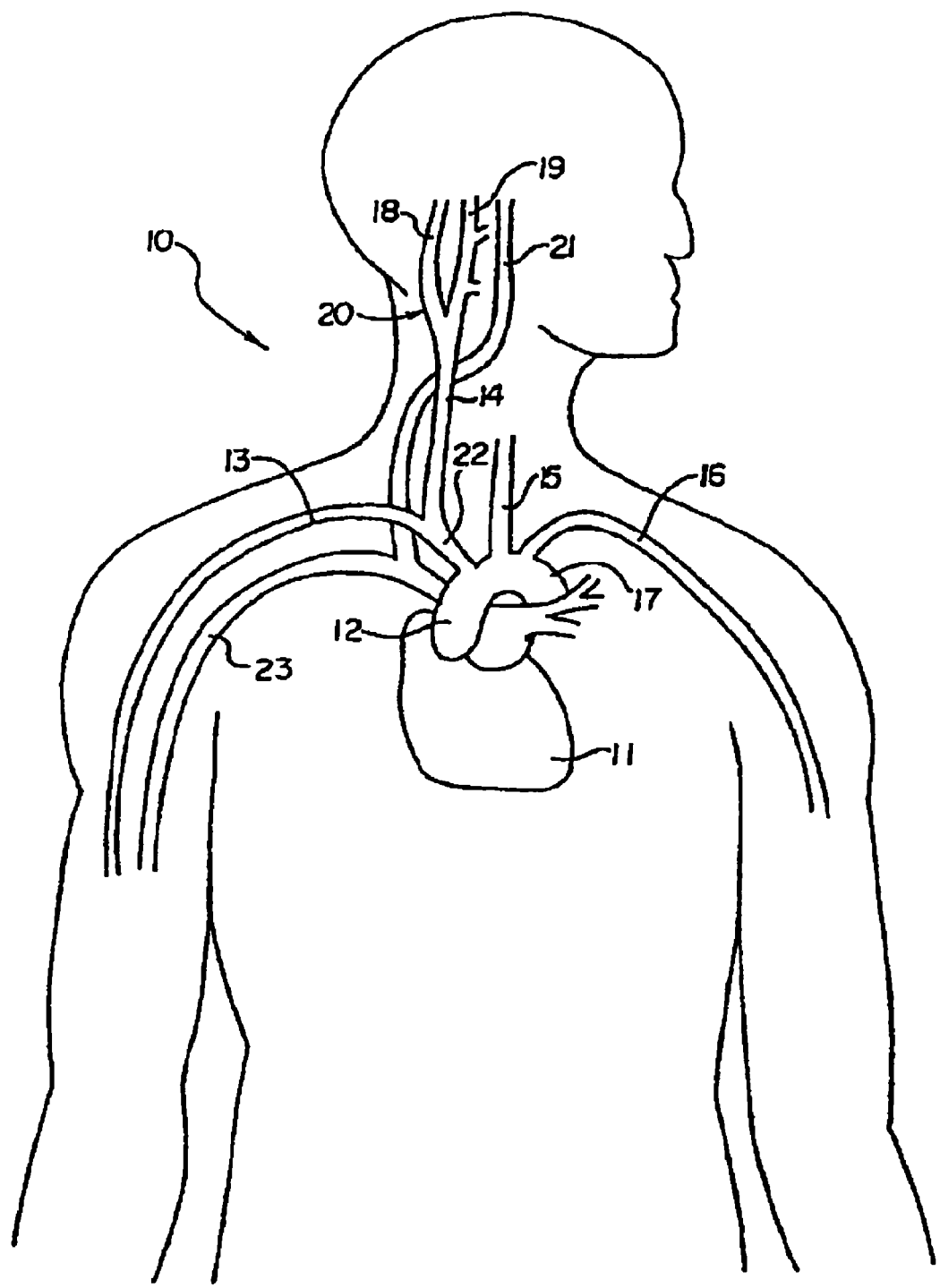
FIG. 1 is a schematic illustration of the upper torso of a human body showing the major arteries and veins and associated anatomy.

Referring now to FIG. 1, within the arterial walls of the aortic arch 12, common carotid arteries 14/15 (near the right carotid sinus 20 and left carotid sinus), subclavian arteries 13/16 and brachiocephalic artery 22 there are baroreceptors

30. For example, as best seen in FIG. 2A, baroreceptors 30 reside within the vascular walls of the carotid sinus 20. Baroreceptors 30 are a type of stretch receptor used by the body to sense blood pressure. An increase in blood pressure causes the arterial wall to stretch, and a decrease in blood pressure causes the arterial wall to return to its original size. Such a cycle is repeated with each beat of the heart. The baroreceptors 30 located in the right carotid sinus 20, the left carotid sinus and the aortic arch 12 play the most significant role in sensing blood pressure that affects the baroreflex system 50, which is described in more detail with reference to FIG. 2B.

Refer now to FIG. 2B, which shows a schematic illustration of baroreceptors 30 disposed in a generic vascular wall 40 and a schematic flow chart of the baroreflex system 50. Baroreceptors 30 are profusely distributed within the arterial walls 40 of the major arteries discussed previously, and generally form an arbor 32. The baroreceptor arbor 32 comprises a plurality of baroreceptors 30, each of which transmits baroreceptor signals to the brain 52 via nerve 38. The baroreceptors 30 are so profusely distributed and arborized within the vascular wall 40 that discrete baroreceptor arbors 32 are not readily discernable. To this end, the baroreceptors 30 shown in FIG. 2B are primarily schematic for purposes of illustration and discussion.

Baroreceptor signals are used to activate a number of body systems which collectively may be referred to as the baroreflex system 50. Baroreceptors 30 are connected to the brain 52 via the nervous system 51, which then activates a number of body systems, including the heart 11, kidneys 53, vessels 54, and other organs/tissues via neurohormonal activity. Although such activation of the baroreflex system 50 has been the subject of other patent applications by the inventors of the present invention, the focus of the present invention is the effect of baroreceptor activation on the brain 52 to treat, control or reduce chronic or acute pain and/or to provide sedation.

Figure 3:
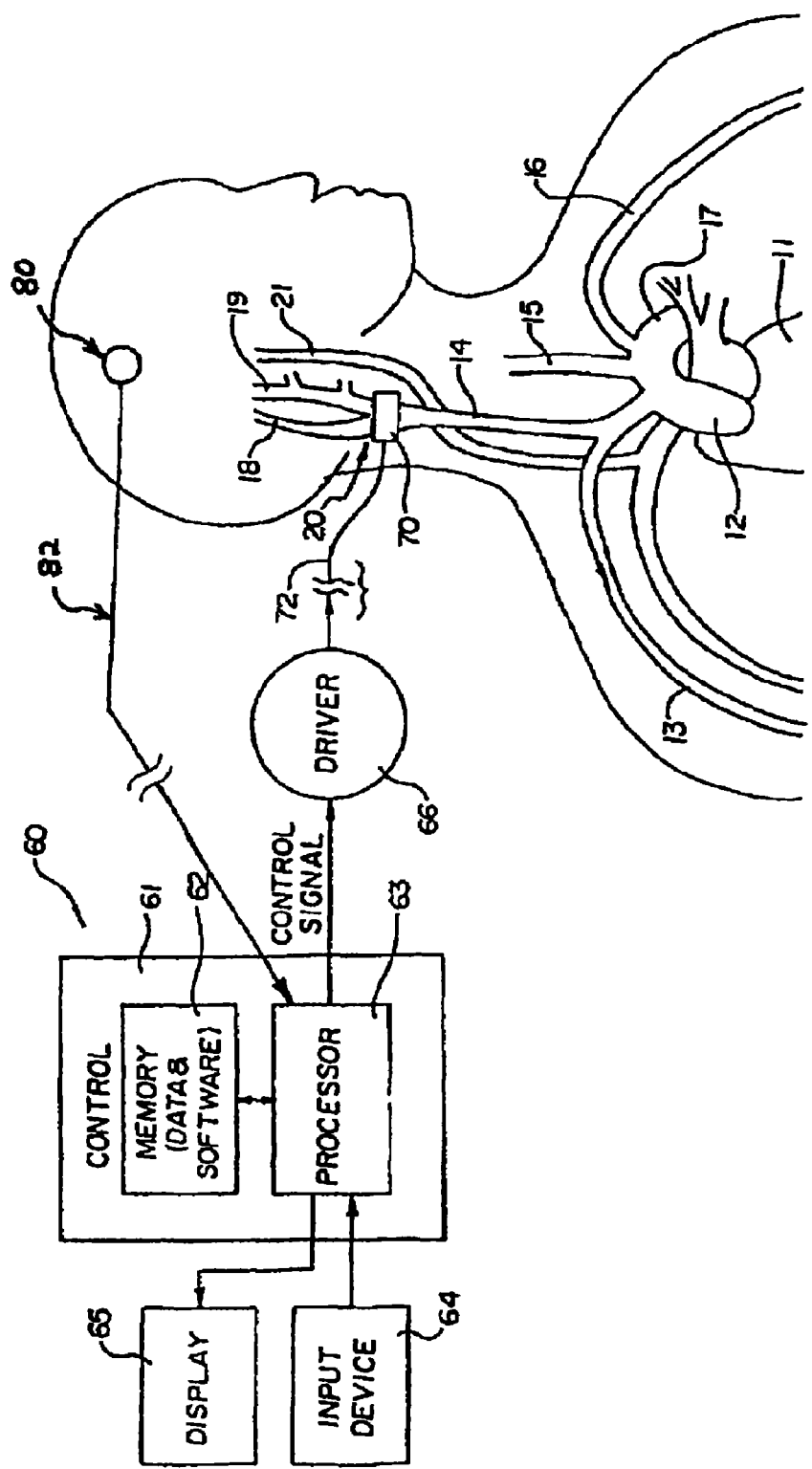
FIG. 3 is a schematic illustration of a baroreflex activation system in accordance with the present invention.

With reference to FIG. 3, the present invention generally provides a system including a control system 60, a baroreflex activation device 70, and a sensor 80 (optional), which generally operate in the following manner. The sensor 80 senses and/or monitors a parameter (e.g., pain sensation) indicative of the need to modify the central nervous system and generates a signal indicative of the parameter. The control system 60 generates a control signal as a function of the received sensor signal. The control signal activates, deactivates or otherwise modulates the baroreflex activation device 70. Typically, activation of the device 70 results in activation of the baroreceptors 30. Alternatively, deactivation or modulation of the baroreflex activation device 70 may cause or modify activation of the baroreceptors 30. The baroreflex activation device 70 may comprise a wide variety of devices which utilize mechanical, electrical, thermal, chemical, biological, or other means to activate baroreceptors 30. Thus, when the sensor 80 detects a parameter indicative of the need to modify central nervous system activity (e.g., excessive neurological activity), the control system 60 generates a control signal to activate the baroreflex activation device 70 thereby inducing a baroreceptor 30 signal. When the sensor 80 detects a parameter indicative of normal body function (e.g., normal neurological activity), the control system 60 generates a control signal to modulate (e.g., deactivate) the baroreflex activation device 70.

As mentioned previously, the baroreflex activation device 70 may comprise a wide variety of devices which utilize mechanical, electrical, thermal, chemical, biological or other means to activate the baroreceptors 30. Specific embodiments of the generic baroreflex activation device 70 are discussed with reference to FIGS. 4-21. In most instances, particularly the mechanical activation embodiments, the baroreflex activation device 70 indirectly activates one or more baroreceptors 30 by stretching or otherwise deforming the vascular wall 40 surrounding the baroreceptors 30. In some other instances, particularly the non-mechanical activation embodiments, the baroreflex activation device 70 may directly activate one or more baroreceptors 30 by changing the electrical, thermal or chemical environment or potential across the baroreceptors 30. It is also possible that changing the electrical, thermal or chemical potential across the tissue surrounding the baroreceptors 30 may cause the surrounding tissue to stretch or otherwise deform, thus mechanically activating the baroreceptors 30. In other instances, particularly the biological activation embodiments, a change in the function or sensitivity of the baroreceptors 30 may be induced by changing the biological activity in the baroreceptors 30 and altering their intracellular makeup and function.

All of the specific embodiments of the baroreflex activation device 70 are suitable for implantation, and are preferably implanted using a minimally invasive percutaneous translumenal approach and/or a minimally invasive surgical approach, depending on whether the device 70 is disposed intravascularly, extravascularly or within the vascular wall 40. The baroreflex activation device 70 may be positioned anywhere baroreceptors 30 affecting the baroreflex system 50 are numerous, such as in the heart 11, in the aortic arch 12, in the common carotid arteries 18/19 near the carotid sinus 20, in the subclavian arteries 13/16, or in the brachiocephalic artery 22. The baroreflex activation device 70 may be implanted such that the device 70 is positioned immediately adjacent the baroreceptors 30. Alternatively, the baroreflex activation device 70 may be positioned in the low-pressure side of the heart or vasculature, near a baroreceptor, as described in U.S. patent application Ser. No. 10/284,063, previously incorporated by reference. In fact, the baroreflex activation device 70 may even be positioned outside the body such that the device 70 is positioned a short distance from but proximate to the baroreceptors 30. In one embodiment, the baroreflex activation device 70 is implanted near the right carotid sinus 20 and/or the left carotid sinus (near the bifurcation of the common carotid artery) and/or the aortic arch 12, where baroreceptors 30 have a significant impact on the baroreflex system 50. For purposes of illustration only, the present invention is described with reference to baroreflex activation device 70 positioned near the carotid sinus 20.

The optional sensor 80 is operably coupled to the control system 60 by electric sensor cable or lead 82. The sensor 80 may comprise any suitable device that measures or monitors a parameter indicative of the need to modify the activity of the central nervous system. For example, the sensor 80 may comprise a physiologic transducer or gauge that measures neurological activity, similar to an electroencephalogram (EEG). Alternatively, the sensor 80 may measure nervous system activity by any other technique. Examples of suitable transducers or gauges for the sensor 80 include EEG electrodes and the like. Although only one sensor 80 is shown, multiple sensors 80 of the same or different type at the same or different locations may be utilized.

The sensor 80 is preferably positioned on or near the patient's head, near the spinal cord or one or more nerves, or in another suitable location to measure neurological activity such as pain sensation or neurological activity indicative of pain. The sensor 80 may be disposed inside the body such as in or on the brain or a nerve (e.g., the vagus nerve), or disposed outside the body, depending on the type of transducer or gauge utilized. The sensor 80 may be separate from the baroreflex activation device 70 or combined therewith. For purposes of illustration only, the sensor 80 is shown positioned on the head of the patient.

By way of example, the control system 60 includes a control block 61 comprising a processor 63 and a memory 62. Control system 60 is connected to the sensor 80 by way of sensor cable 82. Control system 60 is also connected to the baroreflex activation device 70 by way of electric control cable 72. Thus, the control system 60 receives a sensor signal from the sensor 80 by way of sensor cable 82, and transmits a control signal to the baroreflex activation device 70 by way of control cable 72.

The memory 62 may contain data related to the sensor signal, the control signal, and/or values and commands provided by the input device 64. The memory 62 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value or when the sensor signal indicates a specific physiologic event.

As mentioned previously, the baroreflex activation device 70 may activate baroreceptors 30 mechanically, electrically, thermally, chemically, biologically or otherwise. In some instances, the control system 60 includes a driver 66 to provide the desired power mode for the baroreflex activation device 70. For example if the baroreflex activation device 70 utilizes pneumatic or hydraulic actuation, the driver 66 may comprise a pressure/vacuum source and the cable 72 may comprise fluid line(s). If the baroreflex activation device 70 utilizes electrical or thermal actuation, the driver 66 may comprise a power amplifier or the like and the cable 72 may comprise electrical lead(s). If the baroreflex activation device 70 utilizes chemical or biological actuation, the driver 66 may comprise a fluid reservoir and a pressure/vacuum source, and the cable 72 may comprise fluid line(s). In other instances, the driver 66 may not be necessary, particularly if the processor 63 generates a sufficiently strong electrical signal for low level electrical or thermal actuation of the baroreflex activation device 70.

The control system 60 may operate as a closed loop utilizing feedback from the sensor 80, or as an open loop utilizing commands received by input device 64. The open loop operation of the control system 60 preferably utilizes some feedback from the transducer 80, but may also operate without feedback. Commands received by the input device 64 may directly influence the control signal or may alter the software and related algorithms contained in memory 62. The patient and/or treating physician may provide commands to input device 64. Display 65 may be used to view the sensor signal, control signal and/or the software/data contained in memory 62.

The control signal generated by the control system 60 may be continuous, periodic, episodic or a combination thereof, as dictated by an algorithm contained in memory 62. The algorithm contained in memory 62 defines a stimulus regimen which dictates the characteristics of the control signal as a function of time, and thus dictates the stimulation of baroreceptors as a function of time. Continuous control signals include a pulse, a train of pulses, a triggered pulse and a triggered train of pulses, all of which are generated continuously. Examples of periodic control signals include each of the continuous control signals described above which have a designated start time (e.g., beginning of each minute, hour or day) and a designated duration (e.g., 1 second, 1 minute, 1 hour). Examples of episodic control signals include each of the continuous control signals described above which are triggered by an episode (e.g., activation by the patient/physician, an increase in blood pressure above a certain threshold, etc.).

The stimulus regimen governed by the control system 60 may be selected to promote long term efficacy. It is theorized that uninterrupted or otherwise unchanging activation of the baroreceptors 30 may result in the baroreceptors and/or the baroreflex system becoming less responsive over time, thereby diminishing the long-term effectiveness of the therapy. Therefore, the stimulus regimen may be selected to activate, deactivate or otherwise modulate the baroreflex activation device 70 in such a way that therapeutic efficacy is maintained long term.

In addition to maintaining therapeutic efficacy over time, the stimulus regimens of the present invention may be selected reduce power requirement/consumption of the system 60. As will be described in more detail hereinafter, the stimulus regimen may dictate that the baroreflex activation device 70 be initially activated at a relatively higher energy and/or power level, and subsequently activated at a relatively lower energy and/or power level. The first level attains the desired initial therapeutic effect, and the second (lower) level sustains the desired therapeutic effect long term. By reducing the energy and/or power level after the desired therapeutic effect is initially attained, the power required or consumed by the activation device 70 is also reduced long term. This may correlate into systems having greater longevity and/or reduced size (due to reductions in the size of the power supply and associated components).

Such stimulus regimens may be applied to all baroreceptor activation embodiments described herein. In addition to baroreflex activation devices 70, such stimulus regimens may be applied to the stimulation of the carotid sinus nerves or other nerves. In particular, the stimulus regimens described herein may be applied to baropacing (i.e., electrical stimulation of the carotid sinus nerve), as in the baropacing system disclosed in U.S. Pat. No. 6,073,048 to Kieval et al., the entire disclosure of which is incorporated herein by reference.

The stimulus regimen may be described in terms of the control signal and/or the output signal from the baroreflex activation device 70. Generally speaking, changes in the control signal result in corresponding changes in the output of the baroreflex activation device 70 which affect corresponding changes in the baroreceptors 30. The correlation between changes in the control signal and changes in the baroreflex activation device 70 may be proportional or disproportional, direct or indirect (inverse), or any other known or predictable mathematical relationship. For purposes of illustration only, the stimulus regimen may be described herein in such a way that assumes the output of the baroreflex activation device 70 is directly proportional to the control signal.

A first general approach for a stimulus regimen which promotes long term efficacy and reduces power requirements/consumption involves generating a control signal to cause the baroreflex activation device 70 to have a first output level of relatively higher energy and/or power, and subsequently changing the control signal to cause the baroreflex activation device 70 to have a second output level of relatively lower energy and/or power. The first output level may be selected and maintained for sufficient time to attain the desired initial effect (e.g., reduced pain and/or increased sedation), after which the output level may be reduced to the second level for sufficient time to sustain the desired effect for the desired period of time.

For example, if the first output level has a power and/or energy value of X1, the second output level may have a power and/or energy value of X2, wherein X2 is less than X1. In some instances, X2 may be equal to zero, such that the first level is "on" and the second level is "off". It is recognized that power and energy refer to two different parameters, but may, at least in some contexts, be used interchangeably. Generally speaking, power is a time derivative of energy. Thus, in some cases, a change in one of the parameters (power or energy) may not correlate to the same or similar change in the other parameter. In the present invention, it is contemplated that a change in one or both of the parameters may be suitable to obtain the desired result of promoting long term efficacy.

It is also contemplated that more than two levels may be used. Each further level may increase the output energy or power to attain the desired effect, or decrease the output energy or power to retain the desired effect. For example, in some instances, it may be desirable to have further reductions in the output level if the desired effect may be sustained at lower power or energy levels. In other instances, particularly when the desired effect is diminishing or is otherwise not sustained, it may be desirable to increase the output level until the desired effect is reestablished, and subsequently decrease the output level to sustain the effect.

The transition from each level may be a step function (e.g., a single step or a series of steps), a gradual transition over a period of time, or a combination thereof. In addition, the signal levels may be continuous, periodic or episodic as discussed previously.

The output (power or energy) level of the baroreflex activation device 70 may be changed in a number of different ways depending on the mode of activation utilized. For example, in the mechanical activation embodiments described herein, the output level of the baroreflex activation device 70 may be changed by changing the output force/pressure, tissue displacement distance, and/or rate of tissue displacement. In the thermal activation embodiments described herein, the output level of the baroreflex activation device 70 may be changed by changing the temperature, the rate of temperature increase, or the rate of temperature decrease (dissipation rate). In the chemical and biological activation embodiments described herein, the output level of the baroreflex activation device 70 may be changed by changing the volume/concentration of the delivered dose and/or the dose delivery rate.

In electrical activation embodiments using a non-modulated signal, the output (power or energy) level of the baroreflex activation device 70 may be changed by changing the voltage, current and/or signal duration. The output signal of the baroreflex activation device 70 may be, for example, constant current or constant voltage. In electrical activation embodiments using a modulated signal, wherein the output signal comprises, for example, a series of pulses, several pulse characteristics may be changed individually or in combination to change the power or energy level of the output signal. Such pulse characteristics include, but are not limited to: pulse amplitude (PA), pulse frequency (PF), pulse width or duration (PW), pulse waveform (square, triangular, sinusoidal, etc.), pulse polarity (for bipolar electrodes) and pulse phase (monophasic, biphasic).

In electrical activation embodiments wherein the output signal comprises a pulse train, several other signal characteristics may be changed in addition to the pulse characteristics described above. For example, the control or output signal may comprise a pulse train which generally includes a series of pulses occurring in bursts. Pulse train characteristics which may be changed include, but are not limited to: burst amplitude (equal to pulse amplitude if constant within burst packet), burst waveform (i.e., pulse amplitude variation within burst packet), burst frequency (BF), and burst width or duration (BW). The signal or a portion thereof (e.g., burst within the pulse train) may be triggered by any of the events discussed previously, by an EEG signal or a particular portion of an EEG signal, by another physiologic timing indicator, or the like. If the signal or a portion thereof is triggered, the triggering event may be changed and/or the delay from the triggering event may be changed.

A second general approach for a stimulus regimen which promotes long term efficacy and reduces power requirements/consumption involves the use of one baroreflex activation device 70 having multiple output means (e.g., electrodes) or the use of multiple baroreflex activation devices 70 each having a single or multiple output means. Basically, the stimulus regimen according to this approach calls for alternating activation of two or more devices 70 or output means, which are positioned at different anatomical locations. Alternating activation may be accomplished by alternating the control signal between the devices or output means. As used in this context, switching or alternating activation includes switching between individual output means, switching between sets of output means and individual output means, and switching between different sets of output means. By alternating activation between two or more different anatomical locations, the exposure of any single anatomical location to an output signal is reduced.

More specifically, a first device 70 or output means may be connected to a first baroreceptor location, and a second device 70 or output means may be connected to a second baroreceptor location, wherein the first location is different from the second location, and the control signal alternates activation of the first and second devices or output means. Although described with reference to two (first and second) devices 70 or output means, more than two may be utilized. By way of example, not limitation, a first device 70 or output means may be connected to the right carotid sinus, and a second device 70 or output means may be connected to the left carotid sinus. Alternatively, a first device 70 or output means may be connected to the left internal carotid artery, and a second device 70 or output means may be connected to the right internal carotid artery. As yet another alternative, first and second devices 70 or output means may be disposed next to each other but separated by a small distance (e.g., electrodes with multiple contact points). In each instance, the control signal alternates activation of the first and second devices or output means to reduce the signal exposure for each anatomical location. There are many possible anatomical combinations within the scope of this approach which are not specifically mentioned herein for sake of simplicity only.

A third general approach for a stimulus regimen which promotes long term efficacy and reduces power requirements/consumption involves changing the time domain characteristics and/or the triggering event characteristics of the therapy. For example, a periodic control signal which has a designated start time (e.g., beginning of each minute, hour or day; specific time of day) and a designated duration (e.g., 1 second, 1 minute, 1 hour) may have a change in the designated start time and/or duration. Alternatively, an episodic control signal which is triggered by an episode (e.g., activation by the patient/physician, a particular part of an EEG signal, or the like) may have a change in the delay from the triggering event or a change in the triggering event itself. For this latter alternative, the triggering event may be provided by feedback control utilizing sensor 80. As a further alternative, the control signal may be asynchronous, wherein the start time, duration or delay from a base line event is asynchronous (e.g., random).

Any of the foregoing approaches may be utilized alone or in combination. The use of a combination of approaches may further promote long term efficacy and may further reduce power requirements/consumption.

The control system 60 may be implanted in whole or in part. For example, the entire control system 60 may be carried externally by the patient utilizing transdermal connections to the sensor lead 82 and the control lead 72. Alternatively, the control block 61 and driver 66 may be implanted with the input device 64 and display 65 carried externally by the patient utilizing transdermal connections therebetween. As a further alternative, the transdermal connections may be replaced by cooperating transmitters/receivers to remotely communicate between components of the control system 60 and/or the sensor 80 and baroreflex activation device 70.

With general reference to FIGS. 4-21, schematic illustrations of specific embodiments of the baroreflex activation device 70 are shown. The design, function and use of these specific embodiments, in addition to the control system 60 and sensor 80 (not shown), are the same as described with reference to FIG. 3, unless otherwise noted or apparent from the description. In addition, the anatomical features illustrated in FIGS. 4-20 are the same as discussed with reference to FIGS. 1, 2A and 213, unless otherwise noted. In each embodiment, the connections between the components 60/70/80 may be physical (e.g., wires, tubes, cables, etc.) or remote (e.g., transmitter/receiver, inductive, magnetic, etc.). For physical connections, the connection may travel intraarterially, intravenously, subcutaneously, or through other natural tissue paths.

Figure 4B:
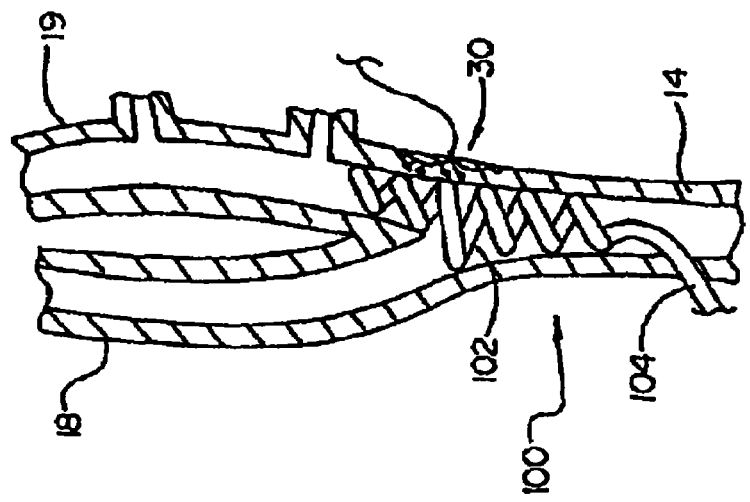
FIGS. 4A and 4B are schematic illustrations of a baroreflex activation device in the form of an internal inflatable balloon which mechanically induces a baroreceptor signal in accordance with an embodiment of the present invention.
Figure 4A:
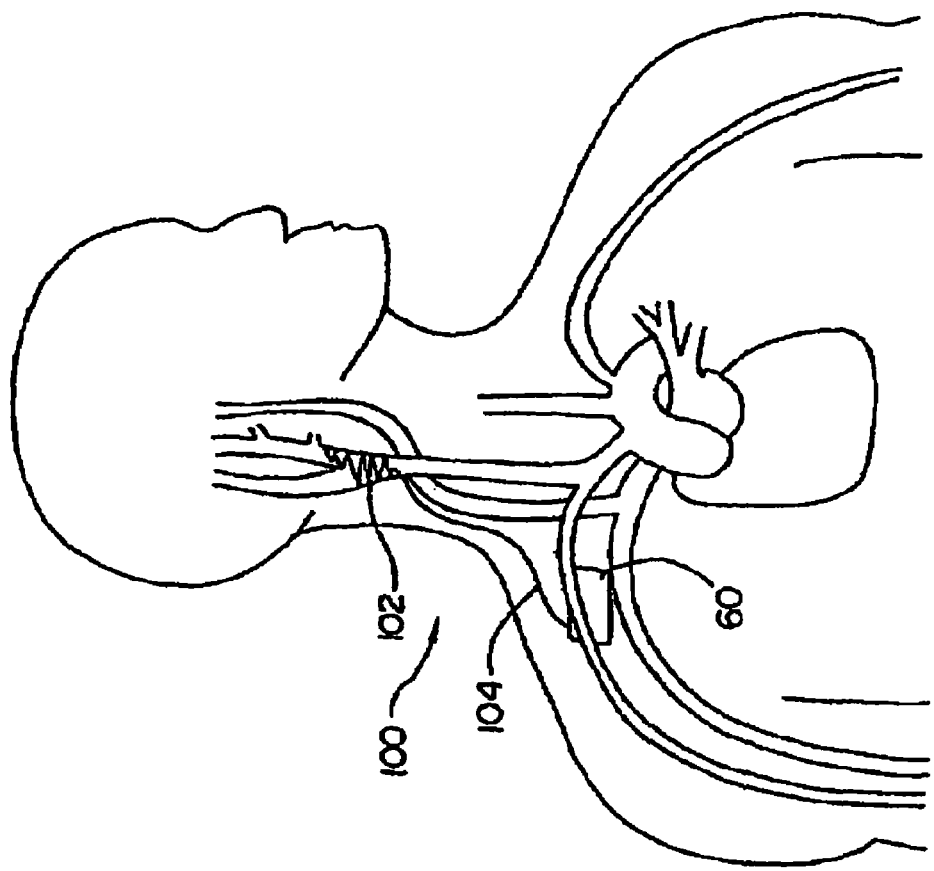

Refer now to FIGS. 4A and 4B which show schematic illustrations of a baroreflex activation device 100 in the form of an intravascular inflatable balloon. The inflatable balloon device 100 includes a helical balloon 102 which is connected to a fluid line 104. An example of a similar helical balloon is disclosed in U.S. Pat. No. 5,181,911 to Shturman, the entire disclosure of which is hereby incorporated by reference. The balloon 102 preferably has a helical geometry or any other geometry which allows blood perfusion therethrough. The fluid line 104 is connected to the driver 66 of the control system 60. In this embodiment, the driver 66 comprises a pressure/vacuum source (i.e., an inflation device) which selectively inflates and deflates the helical balloon 102. Upon inflation, the helical balloon 102 expands, preferably increasing in outside diameter only, to mechanically activate baroreceptors 30 by stretching or otherwise deforming them and/or the vascular wall 40. Upon deflation, the helical balloon 102 returns to its relaxed geometry such that the vascular wall 40 returns to its nominal state. Thus, by selectively inflating the helical balloon 102, the baroreceptors 30 adjacent thereto may be selectively activated.

As an alternative to pneumatic or hydraulic expansion utilizing a balloon, a mechanical expansion device (not shown) may be used to expand or dilate the vascular wall 40 and thereby mechanically activate the baroreceptors 30. For example, the mechanical expansion device may comprise a tubular wire braid structure that diametrically expands when longitudinally compressed as disclosed in U.S. Pat. No. 5,222,971 to Willard et al., the entire disclosure of which is hereby incorporated by reference. The tubular braid may be disposed intravascularly and permits blood perfusion through the wire mesh. In this embodiment, the driver 66 may comprise a linear actuator connected by actuation cables to opposite ends of the braid. When the opposite ends of the tubular braid are brought closer together by actuation of the cables, the diameter of the braid increases to expand the vascular wall 40 and activate the baroreceptors 30.

Refer now to FIGS. 5A and 5B which show schematic illustrations of a baroreflex activation device 120 in the form of an extravascular pressure cuff. The pressure cuff device 120 includes an inflatable cuff 122 which is connected to a fluid line 124. Examples of a similar cuffs 122 are disclosed in U.S. Pat. No. 4,256,094 to Kapp et al. and U.S. Pat. No. 4,881,939 to Newman, the entire disclosures of which are hereby incorporated by reference. The fluid line 124 is connected to the driver 66 of the control system 60. In this embodiment, the driver 66 comprises a pressure/vacuum source (i.e., an inflation device) which selectively inflates and deflates the cuff 122. Upon inflation, the cuff 122 expands, preferably increasing in inside diameter only, to mechanically activate baroreceptors 30 by stretching or otherwise deforming them and/or the vascular wall 40. Upon deflation, the cuff 122 returns to its relaxed geometry such that the vascular wall 40 returns to its nominal state. Thus, by selectively inflating the inflatable cuff 122, the baroreceptors 30 adjacent thereto may be selectively activated.

The driver 66 may be automatically actuated by the control system 60 as discussed above, or may be manually actuated. An example of an externally manually actuated pressure/vacuum source is disclosed in U.S. Pat. No. 4,709,690 to Haber, the entire disclosure of which is hereby incorporated by reference. Examples of transdermally manually actuated pressure/vacuum sources are disclosed in U.S. Pat. No. 4,586, 501 to Claracq, U.S. Pat. No. 4,828,544 to Lane et al., and U.S. Pat. No. 5,634,878 to Grundei et al., the entire disclosures of which are hereby incorporated by reference.

Other external compression devices may be used in place of the inflatable cuff device 120. For example, a piston actuated by a solenoid may apply compression to the vascular wall. An example of a solenoid actuated piston device is disclosed in U.S. Pat. No. 4,014,318 to Dokum et al, and an example of a hydraulically or pneumatically actuated piston device is disclosed in U.S. Pat. No. 4,586,501 to Claracq, the entire disclosures of which are hereby incorporated by reference. Other examples include a rotary ring compression device as disclosed in U.S. Pat. No. 4,551,862 to Haber, and an electromagnetically actuated compression ring device as disclosed in U.S. Pat. No. 5,509,888 to Miller, the entire disclosures of which are hereby incorporated by reference.

Refer now to FIGS. 6A and 6B which show schematic illustrations of a baroreflex activation device 140 in the form of an intravascular deformable structure. The deform able structure device 140 includes a coil, braid or other stent like structure 142 disposed in the vascular lumen. The deformable structure 142 includes one or more individual structural members connected to an electrical lead 144. Each of the structural members forming deformable structure 142 may comprise a shape memory material 146 (e.g., nickel titanium alloy) as illustrated in FIG. 6C, or a bimetallic material 148 as illustrated in FIG. 6D. The electrical lead 144 is connected to the driver 66 of the control system 60. In this embodiment, the driver 66 comprises an electric power generator or amplifier which selectively delivers electric current to the structure 142 which resistively heats the structural members 146/148. The structure 142 may be unipolar as shown using the surrounding tissue as ground, or bipolar or multipolar using leads connected to either end of the structure 142. Electrical power may also be delivered to the structure 142 inductively as described hereinafter with reference to FIGS. 14-16.

Upon application of electrical current to the shape memory material 146, it is resistively heated causing a phase change and a corresponding change in shape. Upon application of electrical current to the bimetallic material 148, it is resistively heated causing a differential in thermal expansion and a corresponding change in shape. In either case, the material 146/148 is designed such that the change in shape causes expansion of the structure 142 to mechanically activate baroreceptors 30 by stretching or otherwise deforming them and/or the vascular wall 40. Upon removal of the electrical current, the material 146/148 cools and the structure 142 returns to its relaxed geometry such that the baroreceptors 30 and/or the vascular wall 40 return to their nominal state. Thus, by selectively expanding the structure 142, the baroreceptors 30 adjacent thereto may be selectively activated.

Refer now to FIGS. 7A and 7B which show schematic illustrations of a baroreflex activation device 160 in the form of an extravascular deformable structure. The extravascular deformable structure device 160 is substantially the same as the intravascular deformable structure device 140 described with reference to FIGS. 6A and 613, except that the extravascular device 160 is disposed about the vascular wall, and therefore compresses, rather than expands, the vascular wall 40. The deformable structure device 160 includes a coil, braid or other stent like structure 162 comprising one or more individual structural members connected to an electrical lead 164. Each of the structural members may comprise a shape memory material 166 (e.g., nickel titanium alloy) as illustrated in FIG. 7C, or a bimetallic material 168 as illustrated in FIG. 7D. The structure 162 may be unipolar as shown using the surrounding tissue as ground, or bipolar or multipolar using leads connected to either end of the structure 162. Electrical power may also be delivered to the structure 162 inductively as described hereinafter with reference to FIGS. 14-16.

Upon application of electrical current to the shape memory material 166, it is resistively heated causing a phase change and a corresponding change in shape. Upon application of electrical current to the bimetallic material 168, it is resistively heated causing a differential in thermal expansion and a corresponding change in shape. In either case, the material 166/168 is designed such that the change in shape causes constriction of the structure 162 to mechanically activate baroreceptors 30 by compressing or otherwise deforming the baroreceptors 30 and/or the vascular wall 40.

Upon removal of the electrical current, the material 166/168 cools and the structure 162 returns to its relaxed geometry such that the baroreceptors 30 and/or the vascular wall 40 return to their nominal state. Thus, by selectively compressing the structure 162, the baroreceptors 30 adjacent thereto may be selectively activated.

Figure 8B:
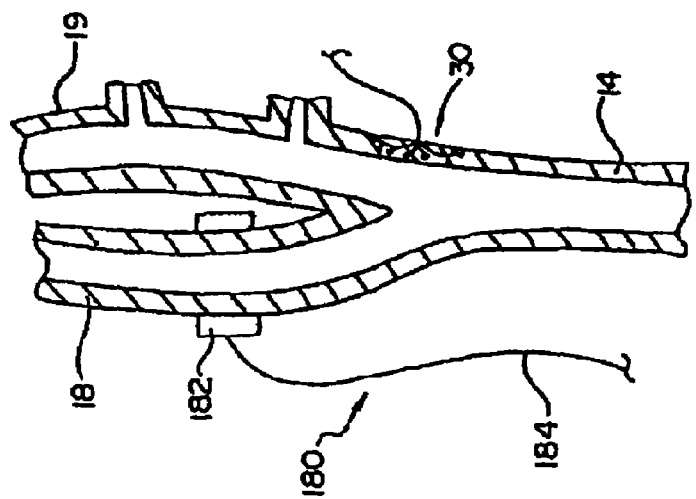
FIGS. 8A and 8B are schematic illustrations of a baroreflex activation device in the form of an external flow regulator which artificially creates back pressure to induce a baroreceptor signal in accordance with an embodiment of the present invention.
Figure 8A:
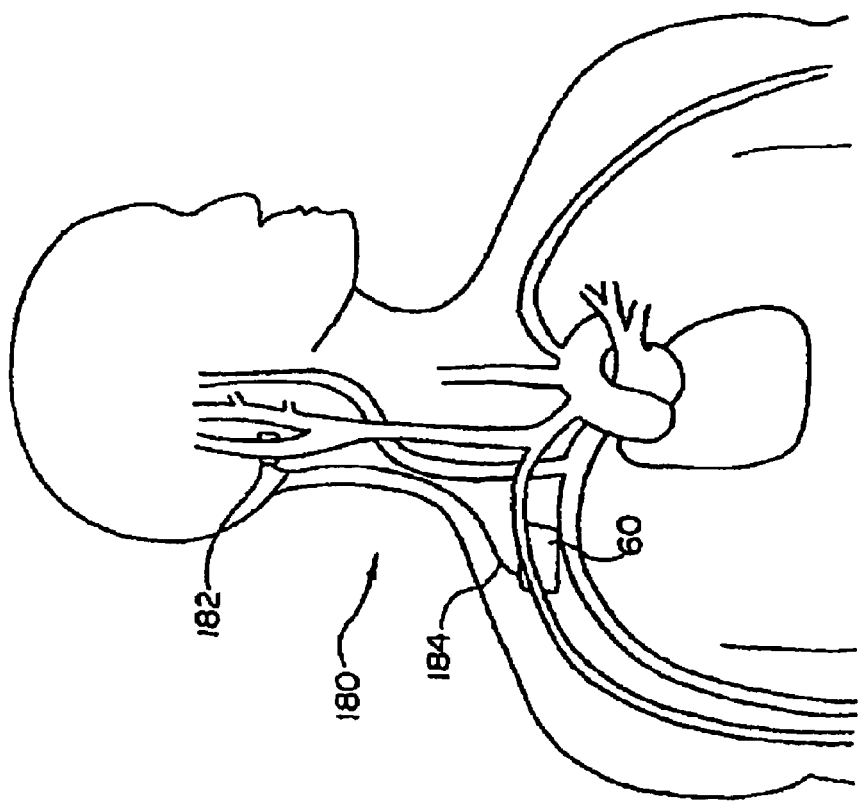

Refer now to FIGS. 8A and 8B which show schematic illustrations of a baroreflex activation device 180 in the form of an extravascular flow regulator which artificially creates back pressure adjacent the baroreceptors 30. The flow regulator device 180 includes an external compression device 182, which may comprise any of the external compression devices described with reference to FIGS. 5A and 5B. The external compression device 182 is operably connected to the driver 66 of the control system 60 by way of cable 184, which may comprise a fluid line or electrical lead, depending on the type of external compression device 182 utilized. The external compression device 182 is disposed about the vascular wall distal of the baroreceptors 30. For example, the external compression device 182 may be located in the distal portions of the external or internal carotid arteries 18/19 to create back pressure adjacent to the baroreceptors 30 in the carotid sinus region 20. Alternatively, the external compression device 182 may be located in the right subclavian artery 13, the right common carotid artery 14, the left common carotid artery 15, the left subclavian artery 16, or the brachiocephalic artery 22 to create back pressure adjacent the baroreceptors 30 in the aortic arch 12.

Upon actuation of the external compression device 182, the vascular wall is constricted thereby reducing the size of the vascular lumen therein. By reducing the size of the vascular lumen, pressure proximal of the external compression device 182 is increased thereby expanding the vascular wall. Thus, by selectively activating the external compression device 182 to constrict the vascular lumen and create back pressure, the baroreceptors 30 may be selectively activated.

Figure 9B:
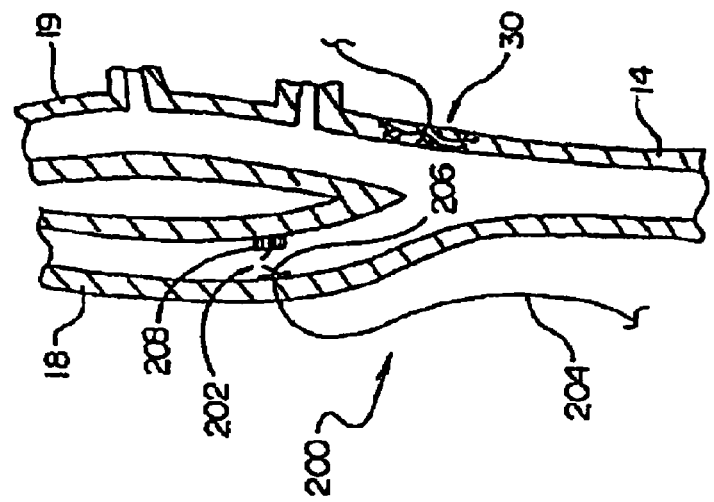
FIGS. 9A and 9B are schematic illustrations of a baroreflex activation device in the form of an internal flow regulator which artificially creates back pressure to induce a baroreceptor signal in accordance with an embodiment of the present invention.
Figure 9A:
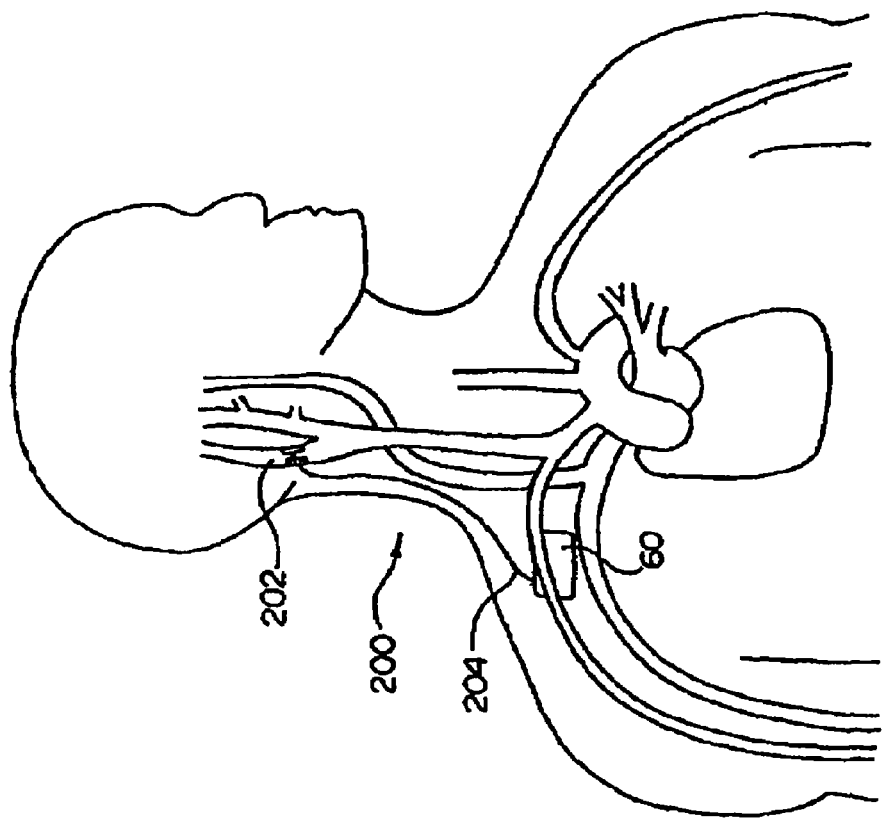

Refer now to FIGS. 9A and 9B which show schematic illustrations of a baroreflex activation device 200 in the form of an intravascular flow regular which artificially creates back pressure adjacent the baroreceptors 30. The intravascular flow regulator device 200 is substantially similar in function and use as extravascular flow regulator 180 described with reference to FIGS. 8A and 8B, except that the intravascular flow regulator device 200 is disposed in the vascular lumen.

Intravascular flow regulator 200 includes an internal valve 202 to at least partially close the vascular lumen distal of the baroreceptors 30. By at least partially closing the vascular lumen distal of the baroreceptors 30, back pressure is created proximal of the internal valve 202 such that the vascular wall expands to activate the baroreceptors 30. The internal valve 202 may be positioned at any of the locations described with reference to the external compression device 182, except that the internal valve 202 is placed within the vascular lumen. Specifically, the internal compression device 202 may be located in the distal portions of the external or internal carotid arteries 18/19 to create back pressure adjacent to the baroreceptors 30 in the carotid sinus region 20. Alternatively, the internal compression device 202 may be located in the right subclavian artery 13, the right common carotid artery 14, the left common carotid artery 15, the left subclavian artery 16, or the brachiocephalic artery 22 to create back pressure adjacent the baroreceptors 30 in the aortic arch 12.

The internal valve 202 is operably coupled to the driver 66 of the control system 60 by way of electrical lead 204. The control system 60 may selectively open, close or change the flow resistance of the valve 202 as described in more detail hereinafter. The internal valve 202 may include valve leaflets 206 (bi-leaflet or trileaflet) which rotate inside housing 208 about an axis between an open position and a closed position. The closed position may be completely closed or partially closed, depending on the desired amount of back pressure to be created. The opening and closing of the internal valve 202 may be selectively controlled by altering the resistance of leaflet 206 rotation or by altering the opening force of the leaflets 206. The resistance of rotation of the leaflets 206 may be altered utilizing electromagnetically actuated metallic bearings carried by the housing 208. The opening force of the leaflets 206 may be altered by utilizing electromagnetic coils in each of the leaflets to selectively magnetize the leaflets such that they either repel or attract each other, thereby facilitating valve opening and closing, respectively.

A wide variety of intravascular flow regulators may be used in place of internal valve 202. For example, internal inflatable balloon devices as disclosed in U.S. Pat. No. 4,682,583 to Burton et al. and U.S. Pat. No. 5,634,878 to Grundei et al., the entire disclosures of which are hereby incorporated by reference, may be adapted for use in place of valve 202. Such inflatable balloon devices may be operated in a similar manner as the inflatable cuff 122 described with reference to FIG.

5. Specifically, in this embodiment, the driver 66 would comprise a pressure/vacuum source (i.e., an inflation device) which selectively inflates and deflates the internal balloon. Upon inflation, the balloon expands to partially occlude blood flow and create back pressure to mechanically activate baroreceptors 30 by stretching or otherwise deforming them and/or the vascular wall 40. Upon deflation, the internal balloon returns to its normal profile such that flow is not hindered and back pressure is eliminated. Thus, by selectively inflating the internal balloon, the baroreceptors 30 proximal thereof may be selectively activated by creating back pressure.

Figure 10B:
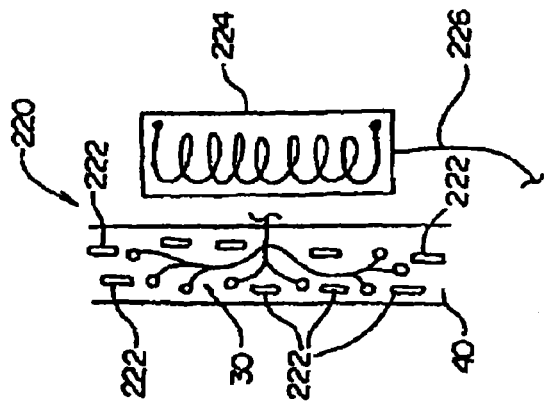
FIGS. 10A and 10B are schematic illustrations of a baroreflex activation device in the form of a magnetic device which mechanically induces a baroreceptor signal in accordance with an embodiment of the present invention.
Figure 10A:
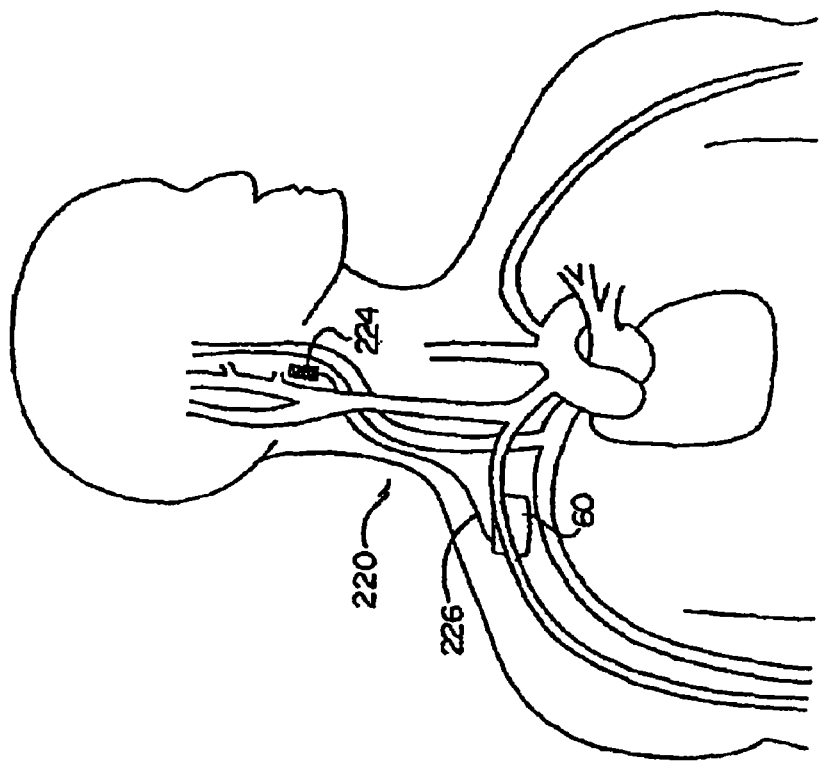

Refer now to FIGS. 10A and 10B which show schematic illustrations of a baroreflex activation device 220 in the form of magnetic particles 222 disposed in the vascular wall 40. The magnetic particles 222 may comprise magnetically responsive materials (i.e., ferrous based materials) and may be magnetically neutral or magnetically active. Preferably, the magnetic particles 222 comprise permanent magnets having an elongate cylinder shape with north and south poles to strongly respond to magnetic fields. The magnetic particles 222 are actuated by an electromagnetic coil 224 which is operably coupled to the driver 66 of the control system 60 by way of an electrical cable 226. The electromagnetic coil 224 may be implanted as shown, or located outside the body, in which case the driver 66 and the remainder of the control system 60 would also be located outside the body. By selectively activating the electromagnetic coil 224 to create a magnetic field, the magnetic particles 222 may be repelled, attracted or rotated. Alternatively, the magnetic field created by the electromagnetic coil 224 may be alternated such that the magnetic particles 222 vibrate within the vascular wall 40. When the magnetic particles are repelled, attracted, rotated, vibrated or otherwise moved by the magnetic field created by the electromagnetic coil 224, the baroreceptors 30 are mechanically activated.

The electromagnetic coil 224 is preferably placed as close as possible to the magnetic particles 222 in the vascular wall 40, and may be placed intravascularly, extravascularly, or in any of the alternative locations discussed with reference to inductor shown in FIGS. 14-16. The magnetic particles 222 may be implanted in the vascular wall 40 by injecting a ferro-fluid or a ferro-particle suspension into the vascular wall adjacent to the baroreceptors 30. To increase biocompatibility, the particles 222 may be coated with a ceramic, polymeric or other inert material. Injection of the fluid carrying the magnetic particles 222 is preferably performed percutaneously.

Figure 11B:
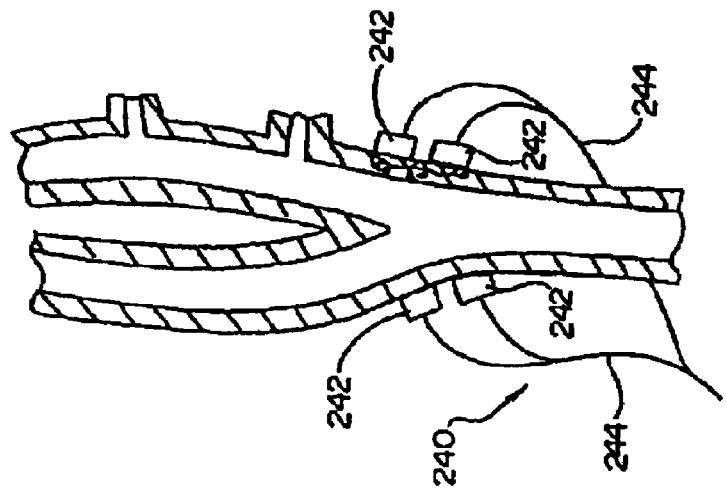
FIGS. 11A and 11B are schematic illustrations of a baroreflex activation device in the form of a transducer which mechanically induces a baroreceptor signal in accordance with an embodiment of the present invention.
Figure 11A:
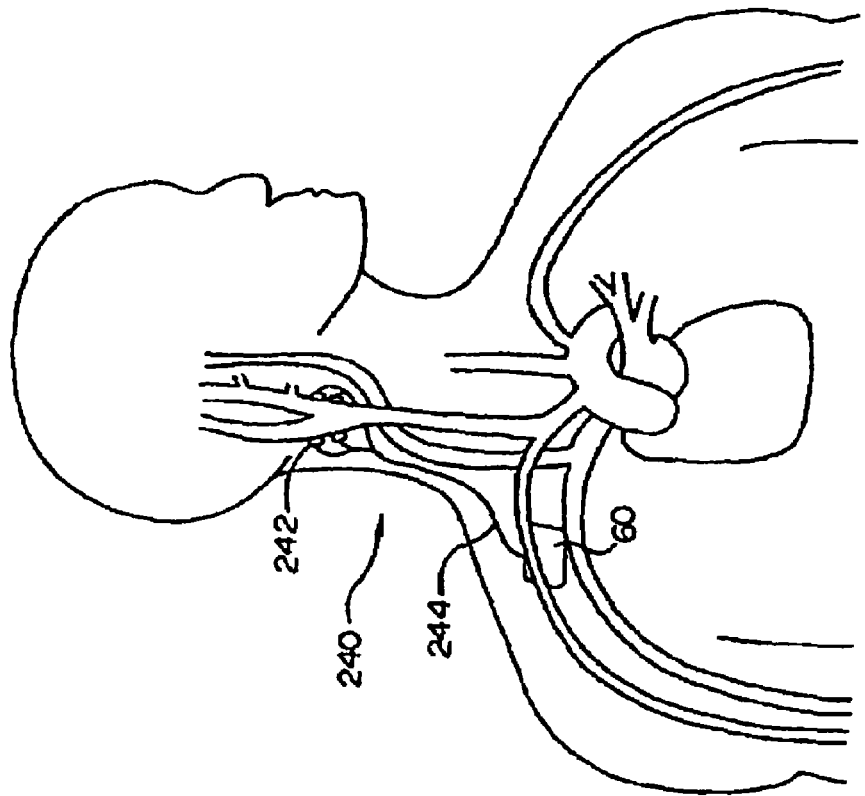

Refer now to FIGS. 11A and 11B which show schematic illustrations of a baroreflex activation device 240 in the form of one or more transducers 242. Preferably, the transducers 242 comprise an array surrounding the vascular wall. The transducers 242 may be intravascularly or extravascularly positioned adjacent to the baroreceptors 30. In this embodiment, the transducers 242 comprise devices which convert electrical signals into some physical phenomena, such as mechanical vibration or acoustic waves. The electrical signals are provided to the transducers 242 by way of electrical cables 244 which are connected to the driver 66 of the control system 60. By selectively activating the transducers 242 to create a physical phenomena, the baroreceptors 30 may be mechanically activated.

The transducers 242 may comprise an acoustic transmitter which transmits sonic or ultrasonic sound waves into the vascular wall 40 to activate the baroreceptors 30. Alternatively, the transducers 242 may comprise a piezoelectric material which vibrates the vascular wall to activate the baroreceptors 30. As a further alternative, the transducers 242 may comprise an artificial muscle which deflects upon application of an electrical signal. An example of an artificial muscle transducer comprises plastic impregnated with a lithium-perchlorate electrolyte disposed between sheets of polypyrrole, a conductive polymer. Such plastic muscles may be electrically activated to cause deflection in different directions depending on the polarity of the applied current.

Figure 12A:
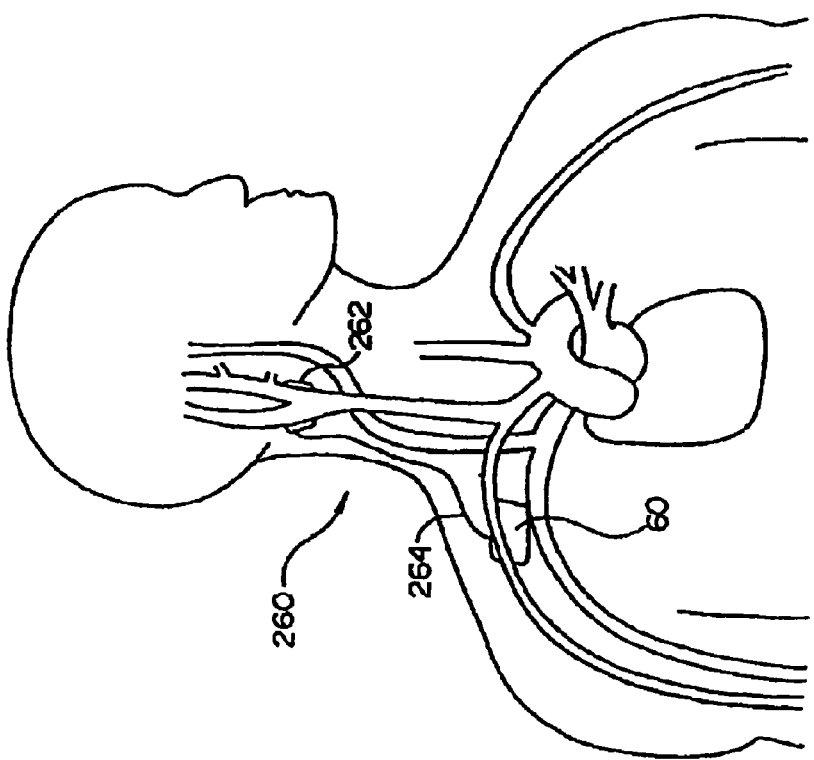
FIGS. 12A and 12B are schematic illustrations of a baroreflex activation device in the form of a fluid delivery device which may be used to deliver an agent which chemically or biologically induces a baroreceptor signal in accordance with an embodiment of the present invention.
Figure 12B:
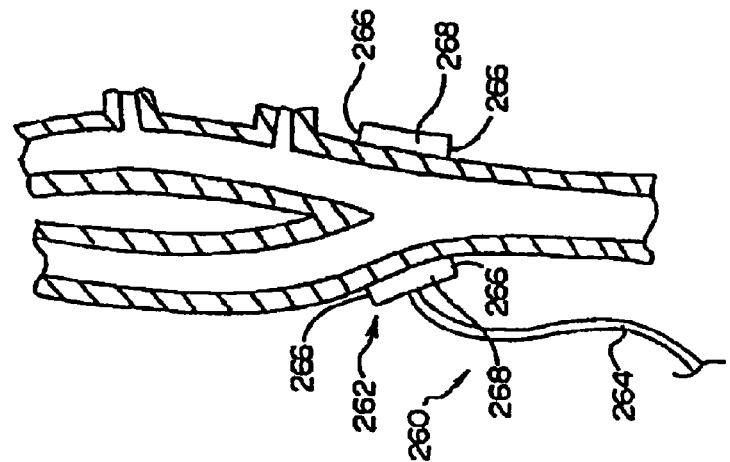

Refer now to FIGS. 12A and 12B which show schematic illustrations of a baroreflex activation device 260 in the form of a local fluid delivery device 262 suitable for delivering a chemical or biological fluid agent to the vascular wall adjacent the baroreceptors 30. The local fluid delivery device 262 may be located intravascularly, extravascularly, or intramurally. For purposes of illustration only, the local fluid delivery device 262 is positioned extravascularly.

The local fluid delivery device 262 may include proximal and distal seals 266 which retain the fluid agent disposed in the lumen or cavity 268 adjacent to vascular wall. Preferably, the local fluid delivery device 262 completely surrounds the vascular wall 40 to maintain an effective seal. Those skilled in the art will recognize that the local fluid delivery device 262 may comprise a wide variety of implantable drug delivery devices or pumps known in the art.

The local fluid delivery device 260 is connected to a fluid line 264 which is connected to the driver 66 of the control system 60. In this embodiment, the driver 66 comprises a pressure/vacuum source and fluid reservoir containing the desired chemical or biological fluid agent. The chemical or biological fluid agent may comprise a wide variety of stimulatory substances. Examples include veratridine, bradykinin, prostaglandins, and related substances. Such stimulatory substances activate the baroreceptors 30 directly or enhance their sensitivity to other stimuli and therefore may be used in combination with the other baroreflex activation devices described herein. Other examples include growth factors and other agents that modify the function of the baroreceptors 30 or the cells of the vascular tissue surrounding the baroreceptors 30 causing the baroreceptors 30 to be activated or causing alteration of their responsiveness or activation pattern to other stimuli. It is also contemplated that injectable stimulators that are induced remotely, as described in U.S. Pat. No. 6,061,596 which is incorporated herein by reference, may be used with the present invention.

As an alternative, the fluid delivery device 260 may be used to deliver a photochemical that is essentially inert until activated by light to have a stimulatory effect as described above. In this embodiment, the fluid delivery device 260 would include a light source such as a light emitting diode (LED), and the driver 66 of the control system 60 would include a pulse generator for the LED combined with a pressure/vacuum source and fluid reservoir described previously. The photochemical would be delivered with the fluid delivery device 260 as described above, and the photochemical would be activated, deactivated or modulated by activating, deactivating or modulating the LED.

As a further alternative, the fluid delivery device 260 may be used to deliver a warm or hot fluid (e.g. saline) to thermally activate the baroreceptors 30. In this embodiment, the driver 66 of the control system 60 would include a heat generator for heating the fluid, combined with a pressure/vacuum source and fluid reservoir described previously. The hot or warm fluid would be delivered and preferably circulated with the fluid delivery device 260 as described above, and the temperature of the fluid would be controlled by the driver 66.

Refer now to FIGS. 13A and 13B which show schematic illustrations of a baroreflex activation device 280 in the form of an intravascular electrically conductive structure or electrode 282. The electrode structure 282 may comprise a self-expanding or balloon expandable coil, braid or other stent-like structure disposed in the vascular lumen. The electrode structure 282 may serve the dual purpose of maintaining lumen patency while also delivering electrical stimuli. To this end, the electrode structure 282 may be implanted utilizing conventional intravascular stent and filter delivery techniques. Preferably, the electrode structure 282 comprises a geometry which allows blood perfusion therethrough.

The electrode structure 282 comprises electrically conductive material which may be selectively insulated to establish contact with the inside surface of the vascular wall 40 at desired locations, and limit extraneous electrical contact with blood flowing through the vessel and other tissues.

The electrode structure 282 is connected to electric lead 284 which is connected to the driver 66 of the control system 60. The driver 66, in this embodiment, may comprise a power amplifier, pulse generator or the like to selectively deliver electrical control signals to structure 282. As mentioned previously, the electrical control signal generated by the driver 66 may be continuous, periodic, episodic or a combination thereof, as dictated by an algorithm contained in memory 62 of the control system 60. Continuous control signals include a constant pulse, a constant train of pulses, a triggered pulse and a triggered train of pulses. Periodic control signals include each of the continuous control signals described above which have a designated start time and a designated duration. Episodic control signals include each of the continuous control signals described above which are triggered by an episode.

By selectively activating, deactivating or otherwise modulating the electrical control signal transmitted to the electrode structure 282, electrical energy may be delivered to the vascular wall to activate the baroreceptors 30. As discussed previously, activation of the baroreceptors 30 may occur directly or indirectly. In particular, the electrical signal delivered to the vascular wall 40 by the electrode structure 282 may cause the vascular wall to stretch or otherwise deform thereby indirectly activating the baroreceptors 30 disposed therein. Alternatively, the electrical signals delivered to the vascular wall by the electrode structure 282 may directly activate the baroreceptors 30 by changing the electrical potential across the baroreceptors 30. In either case, the electrical signal is delivered to the vascular wall 40 immediately adjacent to the baroreceptors 30. It is also contemplated that the electrode structure 282 may delivery thermal energy by utilizing a semi-conductive material having a higher resistance such that the electrode structure 282 resistively generates heat upon application of electrical energy.

Various alternative embodiments are contemplated for the electrode structure 282, including its design, implanted location, and method of electrical activation. For example, the electrode structure 282 may be unipolar as shown in FIGS. 13A and 13B using the surrounding tissue as ground, or bipolar using leads connected to either end of the structure 282 as shown in FIGS. 18A and 18B. In the embodiment of FIGS. 18A and 1813, the electrode structure 282 includes two or more individual electrically conductive members 283/285 which are electrically isolated at their respective cross-over points utilizing insulative materials. Each of the members 283/285 is connected to a separate conductor contained within the electrical lead 284. Alternatively, an array of bipoles may be used as described in more detail with reference to FIG. 21. As a further alternative, a multipolar arrangement may be used wherein three or more electrically conductive members are included in the structure 282. For example, a tripolar arrangement may be provided by one electrically conductive member having a polarity disposed between two electrically conductive members having the opposite polarity.

Figure 21B:
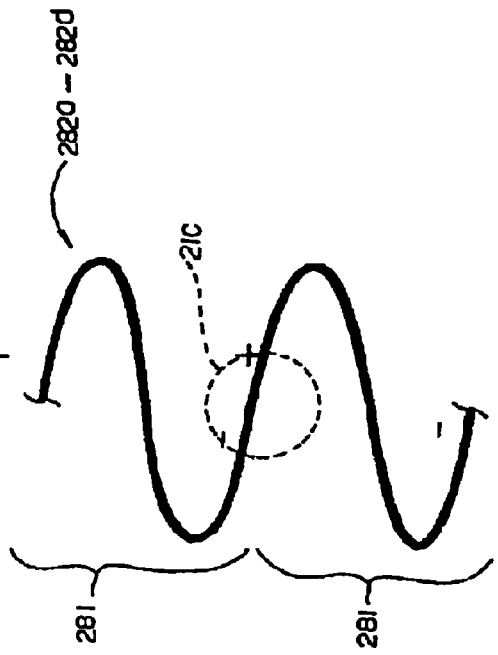
FIGS. 21A-21C are schematic illustrations of a preferred embodiment of an inductively activated electrically conductive structure.
Figure 21C:
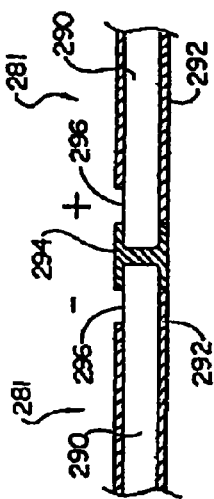
Figure 21A:
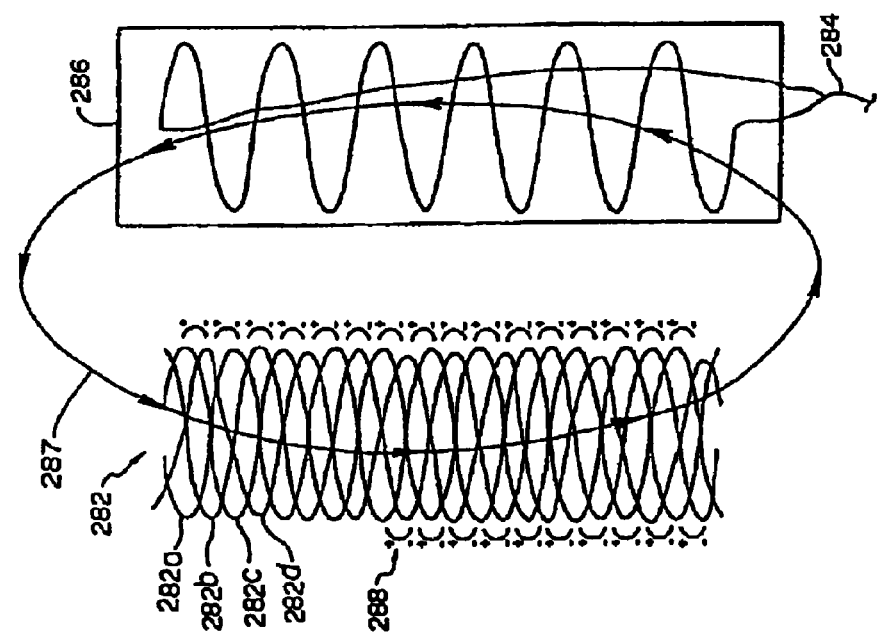

In terms of electrical activation, the electrical signals may be directly delivered to the electrode structure 282 as described with reference to FIGS. 13A and 13B, or indirectly delivered utilizing an inductor as illustrated in FIGS. 14-16 and 21. The embodiments of FIGS. 14-16 and 21 utilize an inductor 286 which is operably connected to the driver 66 of the control system 60 by way of electrical lead 284. The inductor 286 comprises an electrical winding which creates a magnetic field 287 (as seen in FIG. 21) around the electrode structure 282. The magnetic field 287 may be alternated by alternating the direction of current flow through the inductor 286. Accordingly, the inductor 286 may be utilized to create current flow in the electrode structure 282 to thereby deliver electrical signals to the vascular wall 40 to directly or indirectly activate the baroreceptors 30. In all embodiments, the inductor 286 may be covered with an electrically insulative material to eliminate direct electrical stimulation of tissues surrounding the inductor 286. A preferred embodiment of an inductively activated electrode structure 282 is described in more detail with reference to FIGS. 21A-21C.

The embodiments of FIGS. 13-16 may be modified to form a cathode/anode arrangement. Specifically, the electrical inductor 286 would be connected to the driver 66 as shown in FIGS. 14-16 and the electrode structure 282 would be connected to the driver 66 as shown in FIG. 13. With this arrangement, the electrode structure 282 and the inductor 286 may be any suitable geometry and need not be coiled for purposes of induction. The electrode structure 282 and the inductor 286 would comprise a cathode/anode or anode/cathode pair. For example, when activated, the cathode 282 may generate a primary stream of electrons which travel through the inter-electrode space (i.e., vascular tissue and baroreceptors 30) to the anode 286. The cathode is preferably cold, as opposed to thermionic, during electron emission. The electrons may be used to electrically or thermally activate the baroreceptors 30 as discussed previously.

Figure 15B:
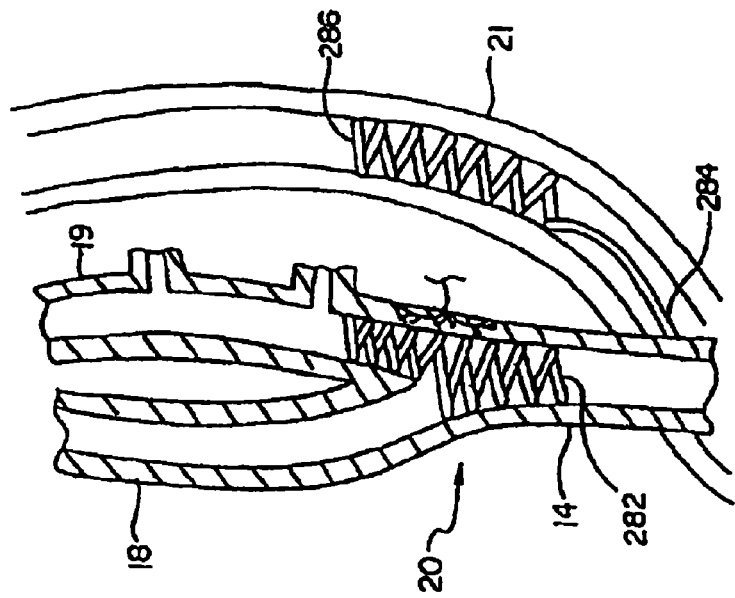
FIGS. 15A and 15B are schematic illustrations of a baroreflex activation device in the form of an internal conductive structure, activated by an internal inductor located in an adjacent vessel, which electrically or thermally induces a baroreceptor signal in accordance with an embodiment of the present invention.
Figure 15A:
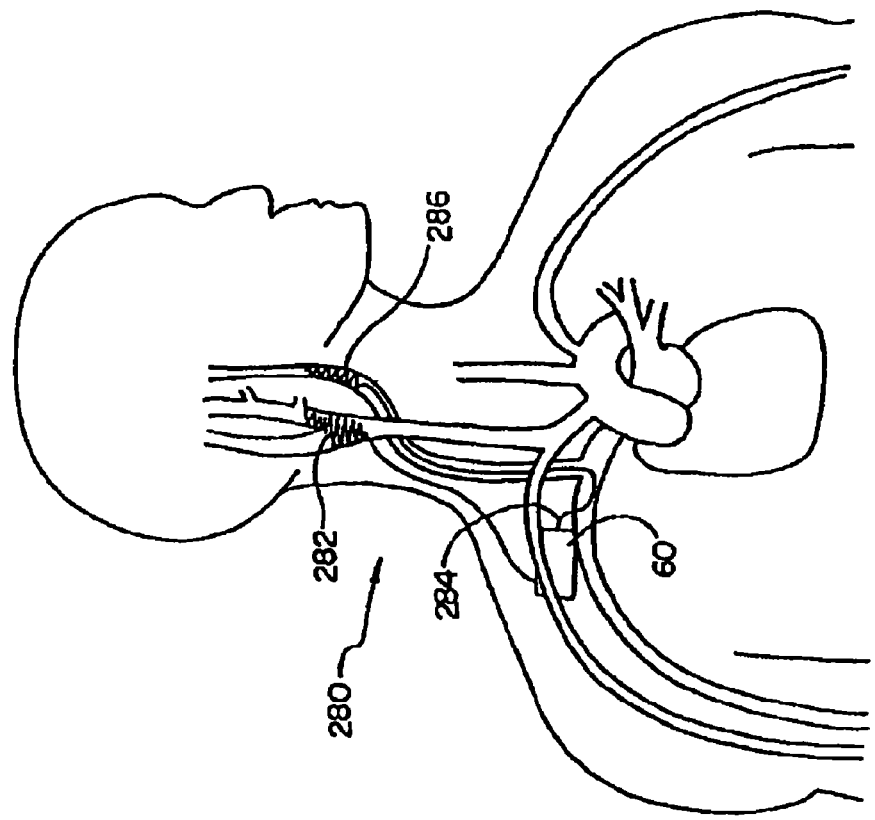
Figure 16B:
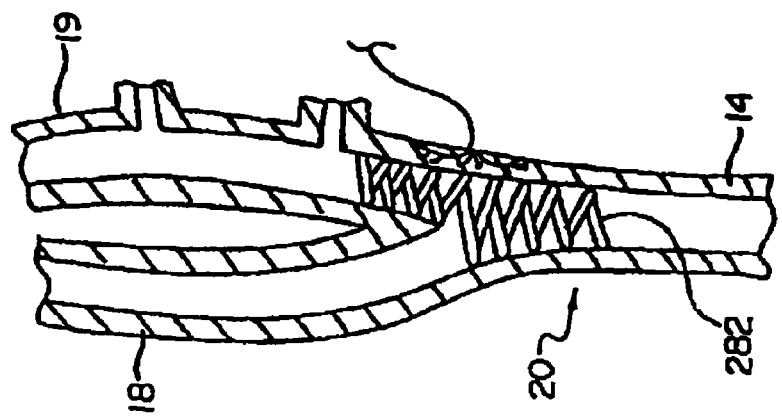
FIGS. 16A and 16B are schematic illustrations of a baroreflex activation device in the form of an internal conductive structure, activated by an external inductor, which electrically or thermally induces a baroreceptor signal in accordance with an embodiment of the present invention.
Figure 16A:
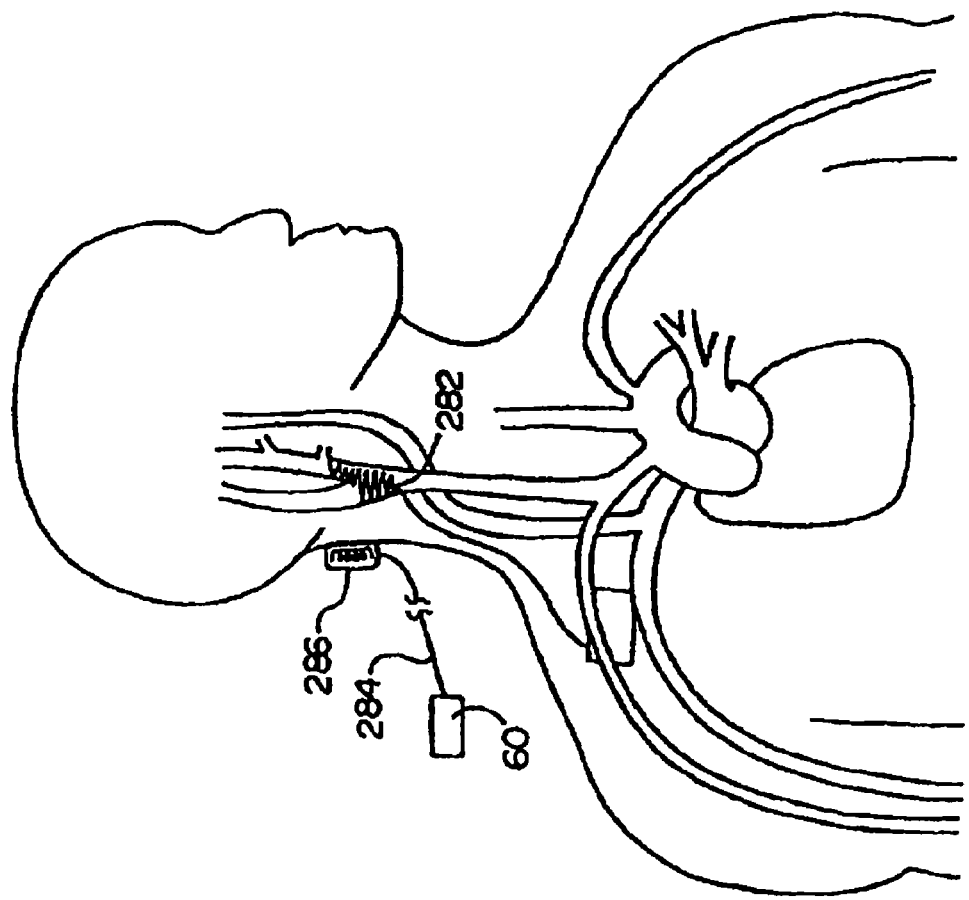

The electrical inductor 286 is preferably disposed as close as possible to the electrode structure 282. For example, the electrical inductor 286 may be disposed adjacent the vascular wall as illustrated in FIGS. 14A and 14B. Alternatively, the inductor 286 may be disposed in an adjacent vessel as illustrated in FIGS. 15A and 15B. If the electrode structure 282 is disposed in the carotid sinus 20, for example, the inductor 286 may be disposed in the internal jugular vein 21 as illustrated in FIGS. 15A and 15B. In the embodiment of FIGS. 15A and 1513, the electrical inductor 286 may comprise a similar structure as the electrode structure 282. As a further alternative, the electrical inductor 286 may be disposed outside the patient's body, but as close as possible to the electrode structure 282. If the electrode structure 282 is disposed in the carotid sinus 20, for example, the electrical inductor 286 may be disposed on the right or left side of the neck of the patient as illustrated in FIGS. 16A and 16B. In the embodiment of FIGS. 16A and 16B, wherein the electrical inductor 286 is disposed outside the patient's body, the control system 60 may also be disposed outside the patient's body.

In terms of implant location, the electrode structure 282 may be intravascularly disposed as described with reference to FIGS. 13A and 13B, or extravascularly disposed as described with reference to FIGS. 17A and 17B, which show schematic illustrations of a baroreflex activation device 300 in the form of an extravascular electrically conductive structure or electrode 302. Except as described herein, the extravascular electrode structure 302 is the same in design, function, and use as the intravascular electrode structure 282. The electrode structure 302 may comprise a coil, braid or other structure capable of surrounding the vascular wall. Alternatively, the electrode structure 302 may comprise one or more electrode patches distributed around the outside surface of the vascular wall. Because the electrode structure 302 is disposed on the outside surface of the vascular wall, intravascular delivery techniques may not be practical, but minimally invasive surgical techniques will suffice. The extravascular electrode structure 302 may receive electrical signals directly from the driver 66 of the control system 60 by way of electrical lead 304, or indirectly by utilizing an inductor (not shown) as described with reference to FIGS. 14-16.

Figure 19B:
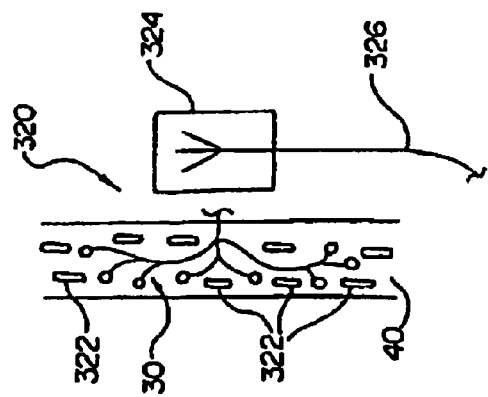
FIGS. 19A and 19B are schematic illustrations of a baroreflex activation device in the form of an electromagnetic field responsive device which electrically or thermally induces a baroreceptor signal in accordance with an embodiment of the present invention.
Figure 19A:
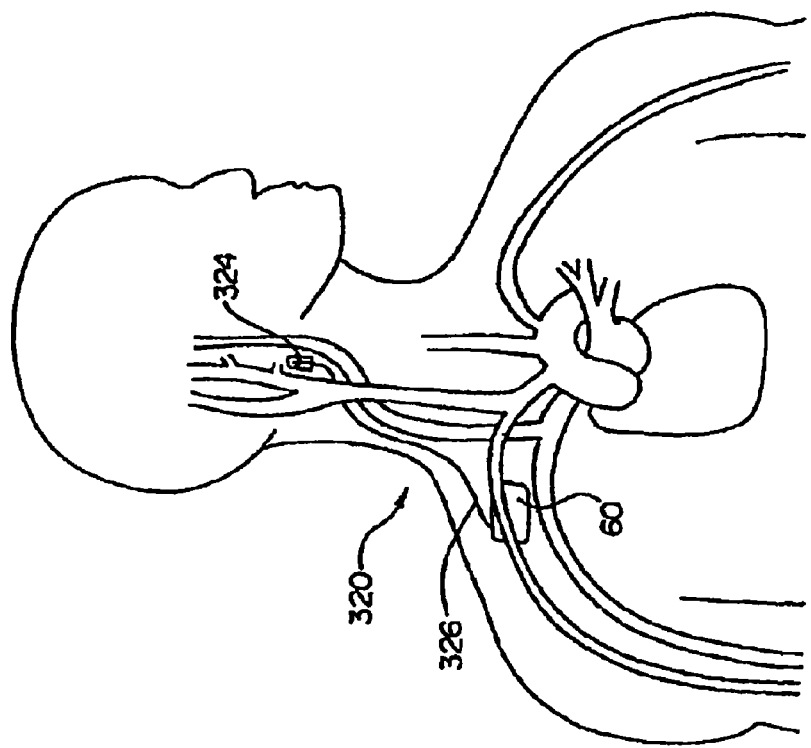

Refer now to FIGS. 19A and 19B which show schematic illustrations of a baroreflex activation device 320 in the form of electrically conductive particles 322 disposed in the vascular wall. This embodiment is substantially the same as the embodiments described with reference to FIGS. 13-18, except that the electrically conductive particles 322 are disposed within the vascular wall, as opposed to the electrically conductive structures 282/302 which are disposed on either side of the vascular wall. In addition, this embodiment is similar to the embodiment described with reference to FIG. 10, except that the electrically conductive particles 322 are not necessarily magnetic as with magnetic particles 222, and the electrically conductive particles 322 are driven by an electromagnetic field rather than by a magnetic field.

In this embodiment, the driver 66 of the control system 60 comprises an electromagnetic transmitter such as an radiofrequency or microwave transmitter. Electromagnetic radiation is created by the transmitter 66 which is operably coupled to an antenna 324 by way of electrical lead 326. Electromagnetic waves are emitted by the antenna 324 and received by the electrically conductive particles 322 disposed in the vascular wall 40. Electromagnetic energy creates oscillating current flow within the electrically conductive particles 322, and depending on the intensity of the electromagnetic radiation and the resistivity of the conductive particles 322, may cause the electrical particles 322 to generate heat. The electrical or thermal energy generated by the electrically conductive particles 322 may directly activate the baroreceptors 30, or indirectly activate the baroreceptors 30 by way of the surrounding vascular wall tissue.

The electromagnetic radiation transmitter 66 and antenna 324 may be disposed in the patient's body, with the antenna 324 disposed adjacent to the conductive particles in the vascular wall 40 as illustrated in FIGS. 19A and 19B. Alternatively, the antenna 324 may be disposed in any of the positions described with reference to the electrical inductor shown in FIGS. 14-16. It is also contemplated that the electromagnetic radiation transmitter 66 and antenna 324 may be utilized in combination with the intravascular and extravascular electrically conductive structures 282/302 described with reference to FIGS. 13-18 to generate thermal energy on either side of the vascular wall.

As an alternative, the electromagnetic radiation transmitter 66 and antenna 324 may be used without the electrically conductive particles 322. Specifically, the electromagnetic radiation transmitter 66 and antenna 324 may be used to deliver electromagnetic radiation (e.g., RF, microwave) directly to the baroreceptors 30 or the tissue adjacent thereto to cause localized heating, thereby thermally inducing a baroreceptor 30 signal.

Figure 20B:
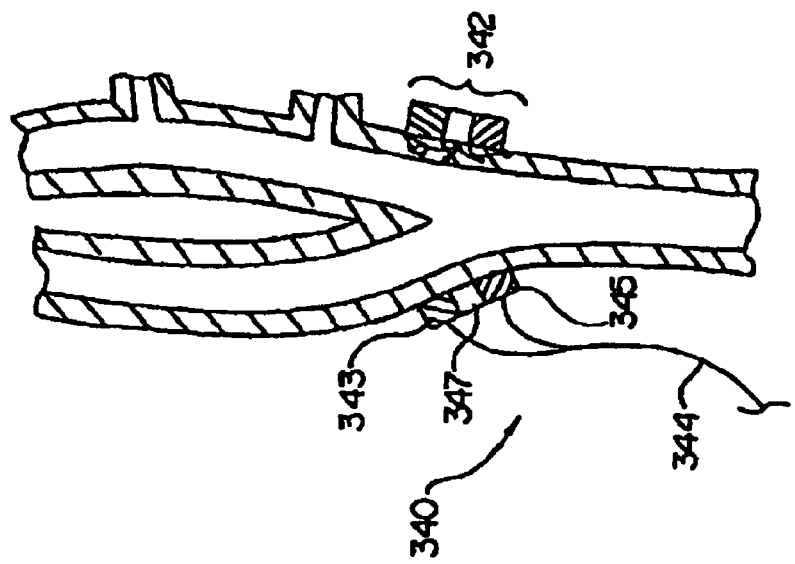
FIGS. 20A and 20B are schematic illustrations of a baroreflex activation device in the form of an external Peltier device which thermally induces a baroreceptor signal in accordance with an embodiment of the present invention.
Figure 20A:
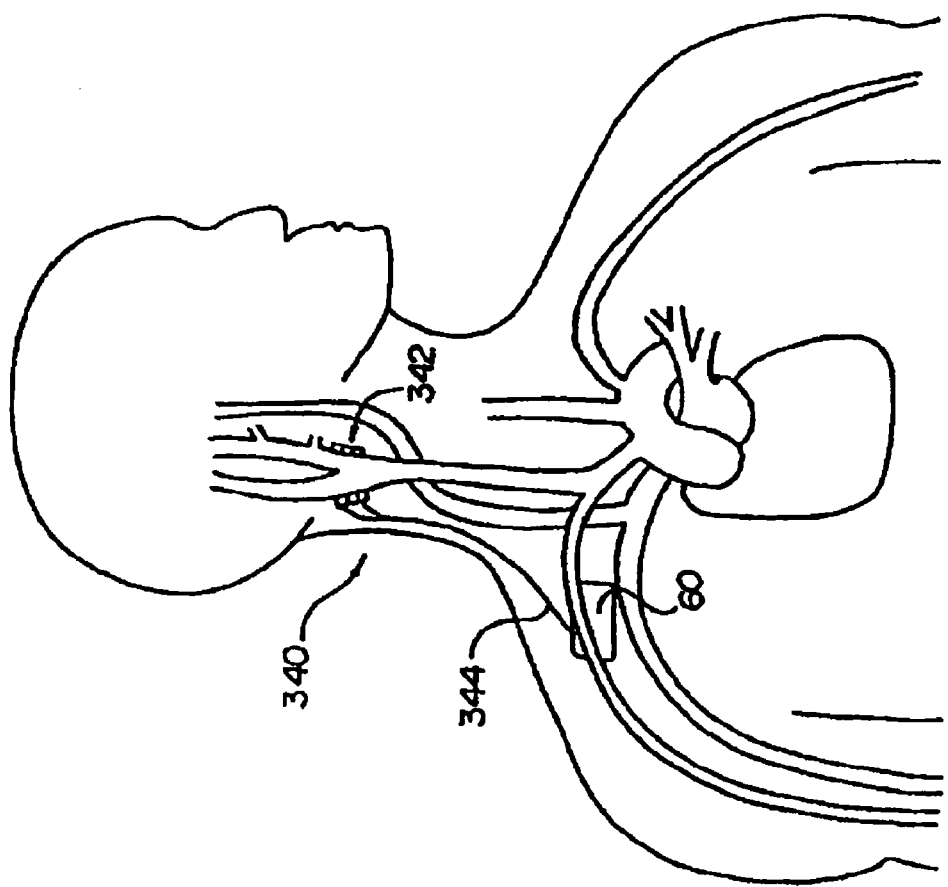

Refer now to FIGS. 20A and 20B which show schematic illustrations of a baroreflex activation device 340 in the form of a Peltier effect device 342. The Peltier effect device 342 may be extravascularly positioned as illustrated, or may be intravascularly positioned similar to an intravascular stent or filter. The Peltier effect device 342 is operably connected to the driver 66 of the control system 60 by way of electrical lead 344. The Peltier effect device 342 includes two dissimilar metals or semiconductors 343/345 separated by a thermal transfer junction 347. In this particular embodiment, the driver 66 comprises a power source which delivers electrical energy to the dissimilar metals or semiconductors 343/345 to create current flow across the thermal junction 347.

When current is delivered in an appropriate direction, a cooling effect is created at the thermal junction 347. There is also a heating effect created at the junction between the individual leads 344 connected to the dissimilar metals or semiconductors 343/345. This heating effect, which is proportional to the cooling effect, may be utilized to activate the baroreceptors 30 by positioning the junction between the electrical leads 344 and the dissimilar metals or semiconductors 343/345 adjacent to the vascular wall 40.

Refer now to FIGS. 21A-21C which show schematic illustrations of a preferred embodiment of an inductively activated electrode structure 282 for use with the embodiments described with reference to FIGS. 14-16. In this embodiment, current flow in the electrode structure 282 is induced by a magnetic field 287 created by an inductor 286 which is operably coupled to the driver 66 of the control system 60 by way of electrical cable 284. The electrode structure 282 preferably comprises a multi-filer self-expanding braid structure including a plurality of individual members 282a, 282b, 282c and 282d. However, the electrode structure 282 may simply comprise a single coil for purposes of this embodiment.

Each of the individual coil members 282a-282d comprising the electrode structure 282 consists of a plurality of individual coil turns 281 connected end to end as illustrated in FIGS. 21B and 21C. FIG. 21C is a detailed view of the connection between adjacent coil turns 281 as shown in FIG. 21B. Each coil turn 281 comprises electrically isolated wires or receivers in which a current flow is established when a changing magnetic field 287 is created by the inductor 286. The inductor 286 is preferably covered with an electrically insulative material to eliminate direct electrical stimulation of tissues surrounding the inductor 286. Current flow through each coil turn 281 results in a potential drop 288 between each end of the coil turn 281. With a potential drop defined at each junction between adjacent coil turns 281, a localized current flow cell is created in the vessel wall adjacent each junction.

Thus an array or plurality of bipoles are created by the electrode structure 282 and uniformly distributed around the vessel wall. Each coil turn 281 comprises an electrically conductive wire material 290 surrounded by an electrically insulative material 292. The ends of each coil turn 281 are connected by an electrically insulated material 294 such that each coil turn 281 remains electrically isolated. The insulative material 294 mechanically joins but electrically isolates adjacent coil turns 281 such that each turn 281 responds with a similar potential drop 288 when current flow is induced by the changing magnetic field 287 of the inductor 286. An exposed portion 296 is provided at each end of each coil turn 281 to facilitate contact with the vascular wall tissue. Each exposed portion 296 comprises an isolated electrode in contact with the vessel wall. The changing magnetic field 287 of the inductor 286 causes a potential drop in each coil turn 281 thereby creating small current flow cells in the vessel wall corresponding to adjacent exposed regions 296. The creation of multiple small current cells along the inner wall of the blood vessel serves to create a cylindrical zone of relatively high current density such that the baroreceptors 30 are activated. However, the cylindrical current density field quickly reduces to a negligible current density near the outer wall of the vascular wall, which serves to limit extraneous current leakage to minimize or eliminate unwanted activation of extravascular tissues and structures such as nerves or muscles.

Refer now to FIGS. 22A-22F which show schematic illustrations of various possible arrangements of electrodes around the carotid sinus 20 for extravascular electrical activation embodiments, such as baroreflex activation device 300 described with reference to FIGS. 17A and 17B. The electrode designs illustrated and described hereinafter may be particularly suitable for connection to the carotid arteries at or near the carotid sinus, and may be designed to minimize extraneous tissue stimulation.

In FIGS. 22A-22F, the carotid arteries are shown, including the common 14, the external 18 and the internal 19 carotid arteries. The location of the carotid sinus 20 may be identified by a landmark bulge 21, which is typically located on the internal carotid artery 19 just distal of the bifurcation, or extends across the bifurcation from the common carotid artery 14 to the internal carotid artery 19.

The carotid sinus 20, and in particular the bulge 21 of the carotid sinus, may contain a relatively high density of baroreceptors 30 (not shown) in the vascular wall. For this reason, it may be desirable to position the electrodes 302 of the activation device 300 on and/or around the sinus bulge 21 to maximize baroreceptor responsiveness and to minimize extraneous tissue stimulation.

It should be understood that the device 300 and electrodes 302 are merely schematic, and only a portion of which may be shown, for purposes of illustrating various positions of the electrodes 302 on and/or around the carotid sinus 20 and the sinus bulge 21. In each of the embodiments described herein, the electrodes 302 may be monopolar (electrodes are cathodes, surrounding tissue is anode or ground), bipolar (cathode-anode pairs), or tripolar (anode-cathode-anode sets). Specific extravascular electrode designs are described in more detail hereinafter.

In FIG. 22A, the electrodes 302 of the extravascular electrical activation device 300 extend around a portion or the entire circumference of the sinus 20 in a circular fashion. In FIG. 2213, the electrodes 302 of the extravascular electrical activation device 300 extend around a portion or the entire circumference of the sinus 20 in a helical fashion. In the helical arrangement shown in FIG. 2213, the electrodes 302 may wrap around the sinus 20 any number of times to establish the desired electrode 302 contact and coverage. In the circular arrangement shown in FIG. 22A, a single pair of electrodes 302 may wrap around the sinus 20, or a plurality of electrode pairs 302 may be wrapped around the sinus 20 as shown in FIG. 22C to establish more electrode 302 contact and coverage.

The plurality of electrode pairs 302 may extend from a point proximal of the sinus 20 or bulge 21, to a point distal of the sinus 20 or bulge 21 to ensure activation of baroreceptors 30 throughout the sinus 20 region. The electrodes 302 may be connected to a single channel or multiple channels as discussed in more detail hereinafter. The plurality of electrode pairs 302 may be selectively activated for purposes of targeting a specific area of the sinus 20 to increase baroreceptor responsiveness, or for purposes of reducing the exposure of tissue areas to activation to maintain baroreceptor responsiveness long term.

Figure 22E:
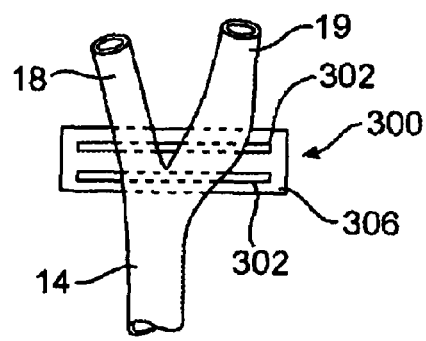
Figure 22F:
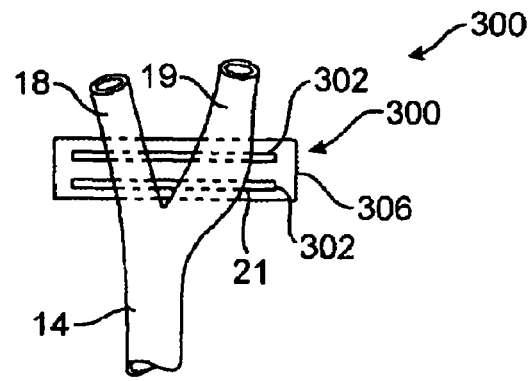

In FIG. 22D, the electrodes 302 extend around the entire circumference of the sinus 20 in a criss-cross fashion. The criss-cross arrangement of the electrodes 302 establishes contact with both the internal 19 and external 18 carotid arteries around the carotid sinus 20. Similarly, in FIG. 22E, the electrodes 302 extend around all or a portion of the circumference of the sinus 20, including the internal 19 and external 18 carotid arteries at the bifurcation, and in some instances the common carotid artery 14. In FIG. 22F, the electrodes 302 extend around all or a portion of the circumference of the sinus 20, including the internal 19 and external 18 carotid arteries distal of the bifurcation. In FIGS. 22E and 22F, the extravascular electrical activation devices 300 are shown to include a substrate or base structure 306 which may encapsulate and insulate the electrodes 302 and may provide a means for attachment to the sinus 20 as described in more detail hereinafter.

From the foregoing discussion with reference to FIGS. 22A-22F, it should be apparent that there are a number of suitable arrangements for the electrodes 302 of the activation device 300, relative to the carotid sinus 20 and associated anatomy. In each of the examples given above, the electrodes 302 are wrapped around a portion of the carotid structure, which may require deformation of the electrodes 302 from their relaxed geometry (e.g., straight). To reduce or eliminate such deformation, the electrodes 302 and/or the base structure 306 may have a relaxed geometry that substantially conforms to the shape of the carotid anatomy at the point of attachment. In other words, the electrodes 302 and the base structure 306 may be pre-shaped to conform to the carotid anatomy in a substantially relaxed state. Alternatively, the electrodes 302 may have a geometry and/or orientation that reduces the amount of electrode 302 strain.

Figure 23:
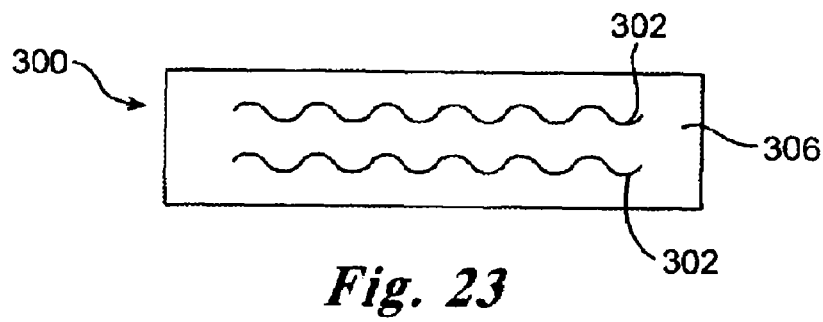
FIG. 23 is a schematic illustration of a serpentine shaped electrode for extravascular electrical activation embodiments.
Figure 24:
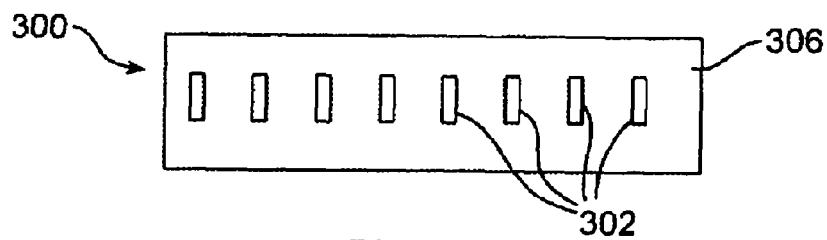
FIG. 24 is a schematic illustration of a plurality of electrodes aligned orthogonal to the direction of wrapping around the carotid sinus for extravascular electrical activation embodiments.

For example, in FIG. 23, the electrodes 302 are shown to have a serpentine or wavy shape. The serpentine shape of the electrodes 302 reduces the amount of strain seen by the electrode material when wrapped around a carotid structure. In addition, the serpentine shape of the electrodes increases the contact surface area of the electrode 302 with the carotid tissue. As an alternative, the electrodes 302 may be arranged to be substantially orthogonal to the wrap direction (i.e., substantially parallel to the axis of the carotid arteries) as shown in FIG. 24. In this alternative, the electrodes 302 each have a length and a width or diameter, wherein the length is substantially greater than the width or diameter. The electrodes 302 each have a longitudinal axis parallel to the length thereof, wherein the longitudinal axis is orthogonal to the wrap direction and substantially parallel to the longitudinal axis of the carotid artery about which the device 300 is wrapped. As with the multiple electrode embodiments described previously, the electrodes 302 may be connected to a single channel or multiple channels as discussed in more detail hereinafter.

Figure 25:
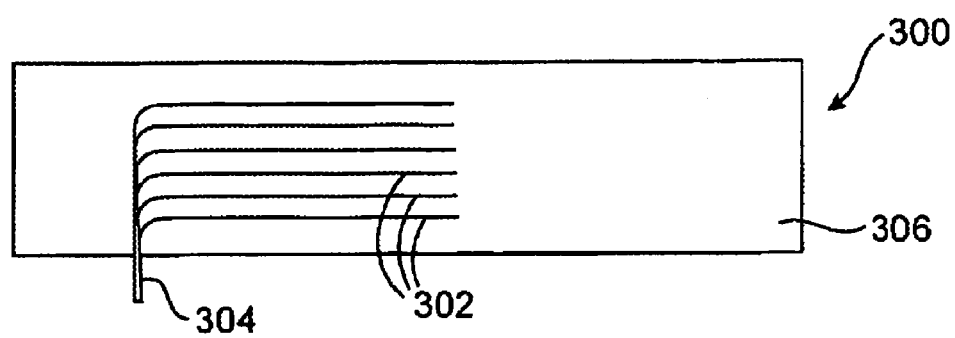
FIGS. 25-28 are schematic illustrations of various multi channel electrodes for extravascular electrical activation embodiments.

Refer now to FIGS. 25-28 which schematically illustrate various multichannel electrodes for the extravascular electrical activation device 300. FIG. 25 illustrates a six (6) channel electrode assembly including six (6) separate elongate electrodes 302 extending adjacent to and parallel with each other. The electrodes 302 are each connected to multi-channel cable 304. Some of the electrodes 302 may be common, thereby reducing the number of channels necessary in the cable 304.

Base structure or substrate 306 may comprise a flexible and electrically insulative material suitable for implantation, such as silicone, perhaps reinforced with a flexible material such as polyester fabric. The base 306 may have a length suitable to wrap around all (360.degree.) or a portion (i.e., less than 360.degree.) of the circumference of one or more of the carotid arteries adjacent the carotid sinus 20. The electrodes 302 may extend around a portion (i.e., less than 360.degree. such as 270.degree., 180.degree. or 90.degree.) of the circumference of one or more of the carotid arteries adjacent the carotid sinus 20. To this end, the electrodes 302 may have a length that is less than (e.g., 75%, 50% or 25%) the length of the base 206. The electrodes 302 may be parallel, orthogonal or oblique to the length of the base 306, which is generally orthogonal to the axis of the carotid artery to which it is disposed about.

The electrodes 302 may comprise round wire, rectangular ribbon or foil formed of an electrically conductive and radio-paque material such as platinum. The base structure 306 substantially encapsulates the electrodes 302, leaving only an exposed area for electrical connection to extravascular carotid sinus tissue. For example, each electrode 302 may be partially recessed in the base 206 and may have one side exposed along all or a portion of its length for electrical connection to carotid tissue. Electrical paths through the carotid tissues may be defined by one or more pairs of the elongate electrodes 302.

In all embodiments described with reference to FIGS. 25-28, the multichannel electrodes 302 may be selectively activated for purposes of mapping and targeting a specific area of the carotid sinus 20 to determine the best combination of electrodes 302 (e.g., individual pair, or groups of pairs) to activate for maximum baroreceptor responsiveness, as described elsewhere herein. In addition, the multichannel electrodes 302 may be selectively activated for purposes of reducing the exposure of tissue areas to activation to maintain long term efficacy as described, as described elsewhere herein. For these purposes, it may be useful to utilize more than two (2) electrode channels. Alternatively, the electrodes 302 may be connected to a single channel whereby baroreceptors are uniformly activated throughout the sinus 20 region.

Various embodiments of the inventive devices may be entirely intravascular, entirely extravascular, or partially intravascular and partially extravascular. Furthermore, devices may reside wholly in or on arterial vasculature, wholly in or on venous vasculature, or in or on some combination of both. In some embodiments, for example, implantable devices may positioned within an artery or vein, while in other embodiments devices may be placed extravascularly, on the outside of an artery or vein. In introducing and placing devices of the present invention, any suitable technique and access route may be employed. For example, in some embodiments an open surgical procedure may be used to place an implantable device. Alternatively, an implantable device may be placed within an artery or vein via a transvascular, intravenous approach. In still other embodiments, an implantable device may be introduced into vasculature via minimally invasive means, advanced to a treatment position through the vasculature, and then advanced outside the vasculature for placement on the outside of an artery or vein. For example, an implantable may be introduced into and advanced through the venous vasculature, made to exit the wall of a vein, and placed at an extravascular site on an artery.

Figure 26:
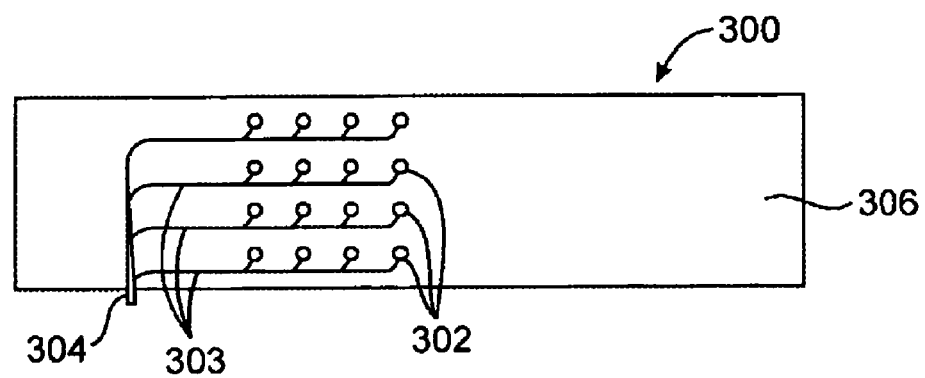

An alternative multi-channel electrode design is illustrated in FIG. 26. In this embodiment, the device 300 includes sixteen (16) individual electrode pads 302 connected to 16-channel cable 304 via 4-channel connectors 303. In this embodiment, the circular electrode pads 302 are partially encapsulated by the base structure 306 to leave one face of each button electrode 302 exposed for electrical connection to carotid tissues. With this arrangement, electrical paths through the carotid tissues may be defined by one or more pairs (bipolar) or groups (tripolar) of electrode pads 302.

Figure 27:
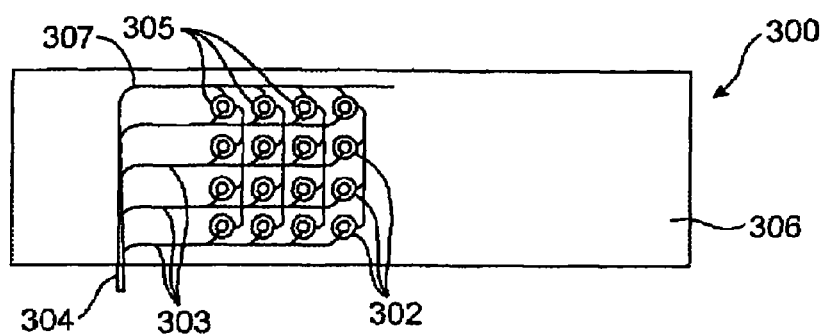

A variation of the multi-channel pad-type electrode design is illustrated in FIG. 27. In this embodiment, the device 300 includes sixteen (16) individual circular pad electrodes 302 surrounded by sixteen (16) rings 305, which collectively may be referred to as concentric electrode pads 302/305. Pad electrodes 302 are connected to 17-channel cable 304 via 4-channel connectors 303, and rings 305 are commonly connected to 17-channel cable 304 via a single channel connector 307. In this embodiment, the circular shaped electrodes 302 and the rings 305 are partially encapsulated by the base structure 306 to leave one face of each pad electrode 302 and one side of each ring 305 exposed for electrical connection to carotid tissues. As an alternative, two rings 305 may surround each electrode 302, with the rings 305 being commonly connected. With these arrangements, electrical paths through the carotid tissues may be defined between one or more pad electrode 302/ring 305 sets to create localized electrical paths.

Figure 28:
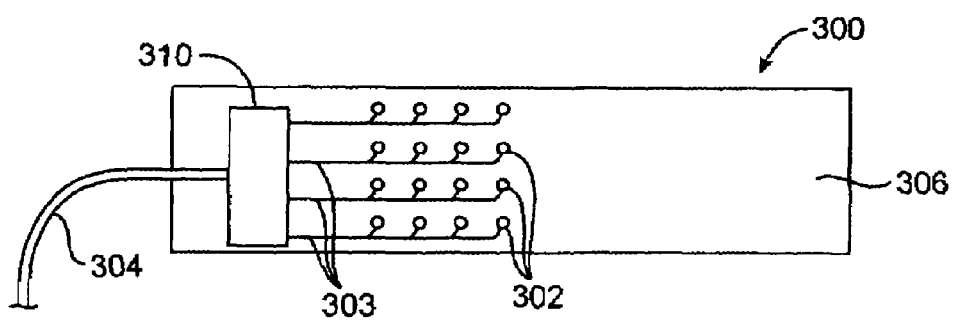

Another variation of the multi-channel pad electrode design is illustrated in FIG. 28. In this embodiment, the device 300 includes a control IC chip 310 connected to 3-channel cable 304. The control chip 310 is also connected to sixteen (16) individual pad electrodes 302 via 4-channel connectors 303. The control chip 310 permits the number of channels in cable 304 to be reduced by utilizing a coding system. The control system 60 sends a coded control signal which is received by chip 310. The chip 310 converts the code and enables or disables selected electrode 302 pairs in accordance with the code.

For example, the control signal may comprise a pulse wave form, wherein each pulse includes a different code. The code for each pulse causes the chip 310 to enable one or more pairs of electrodes, and to disable the remaining electrodes. Thus, the pulse is only transmitted to the enabled electrode pair(s) corresponding to the code sent with that pulse. Each subsequent pulse would have a different code than the preceding pulse, such that the chip 310 enables and disables a different set of electrodes 302 corresponding to the different code. Thus, virtually any number of electrode pairs may be selectively activated using control chip 310, without the need for a separate channel in cable 304 for each electrode 302. By reducing the number of channels in cable 304, the size and cost thereof may be reduced.

Optionally, the IC chip 310 may be connected to feedback sensor 80, taking advantage of the same functions as described with reference to FIG. 3. In addition, one or more of the electrodes 302 may be used as feedback sensors when not enabled for activation. For example, such a feedback sensor electrode may be used to measure or monitor electrical conduction in the vascular wall to provide data analogous to an ECG. Alternatively, such a feedback sensor electrode may be used to sense a change in impedance due to changes in blood volume during a pulse pressure to provide data indicative of heart rate, blood pressure, or other physiologic parameter.

Figure 29:
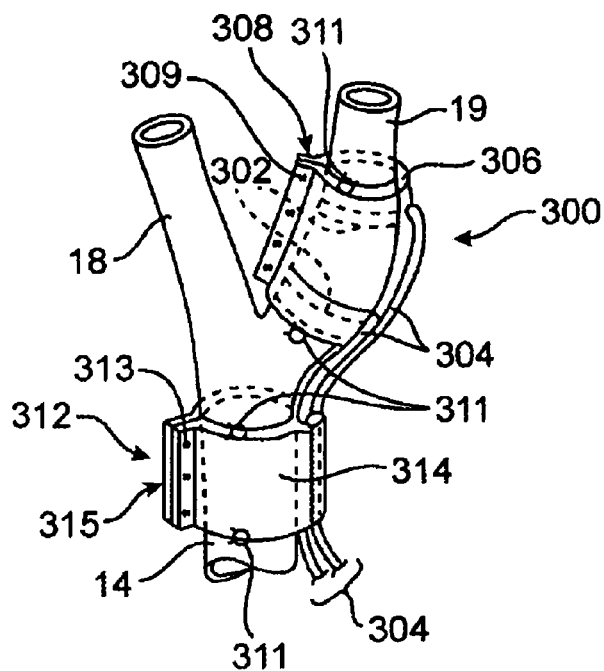
FIG. 29 is a schematic illustration of an extravascular electrical activation device including a tether and an anchor disposed about the carotid sinus and common carotid artery.

Refer now to FIG. 29 which schematically illustrates an extravascular electrical activation device 300 including a support collar or anchor 312. In this embodiment, the activation device 300 is wrapped around the internal carotid artery 19 at the carotid sinus 20, and the support collar 312 is wrapped around the common carotid artery 14. The activation device 300 is connected to the support collar 312 by cables 304, which act as a loose tether. With this arrangement, the collar 312 isolates the activation device from movements and forces transmitted by the cables 304 proximal of the support collar, such as may be encountered by movement of the control system 60 and/or driver 66. As an alternative to support collar 312, a strain relief (not shown) may be connected to the base structure 306 of the activation device 300 at the juncture between the cables 304 and the base 306. With either approach, the position of the device 300 relative to the carotid anatomy may be better maintained despite movements of other parts of the system.

In this embodiment, the base structure 306 of the activation device 300 may comprise molded tube, a tubular extrusion, or a sheet of material wrapped into a tube shape utilizing a suture flap 308 with sutures 309 as shown. The base structure 306 may be formed of a flexible and biocompatible material such as silicone, which may be reinforced with a flexible material such as polyester fabric available under the trade name DACRON to form a composite structure. The inside diameter of the base structure 306 may correspond to the outside diameter of the carotid artery at the location of implantation, for example 6-8 mm. The wall thickness of the base structure 306 may be very thin to maintain flexibility and a low profile, for example less than 1 mm. If the device 300 is to be disposed about a sinus bulge 21, a correspondingly shaped bulge may be formed into the base structure for added support and assistance in positioning.

The electrodes 302 (shown in phantom) may comprise round wire, rectangular ribbon or foil, formed of an electrically conductive and radiopaque material such as platinum or platinum-iridium. The electrodes may be molded into the base structure 306 or adhesively connected to the inside diameter thereof, leaving a portion of the electrode exposed for electrical connection to carotid tissues. The electrodes 302 may encompass less than the entire inside circumference (e.g., 300.degree.) of the base structure 306 to avoid shorting. The electrodes 302 may have any of the shapes and arrangements described previously. For example, as shown in FIG. 29, two rectangular ribbon electrodes 302 may be used, each having a width of 1 mm spaced 1.5 mm apart.

The support collar 312 may be formed similarly to base structure 306. For example, the support collar may comprise molded tube, a tubular extrusion, or a sheet of material wrapped into a tube shape utilizing a suture flap 315 with sutures 313 as shown. The support collar 312 may be formed of a flexible and biocompatible material such as silicone, which may be reinforced to form a composite structure. The cables 304 are secured to the support collar 312, leaving slack in the cables 304 between the support collar 312 and the activation device 300.

In all extravascular embodiments described herein, including electrical activation embodiments, it may be desirable to secure the activation device to the vascular wall using sutures or other fixation means. For example, sutures 311 may be used to maintain the position of the electrical activation device 300 relative to the carotid anatomy (or other vascular site containing baroreceptors). Such sutures 311 may be connected to base structure 306, and pass through all or a portion of the vascular wall. For example, the sutures 311 may be threaded through the base structure 306, through the adventitia of the vascular wall, and tied. If the base structure 306 comprises a patch or otherwise partially surrounds the carotid anatomy, the corners and/or ends of the base structure may be sutured, with additional sutures evenly distributed therebetween. In order to minimize the propagation of a hole or a tear through the base structure 306, a reinforcement material such as polyester fabric may be embedded in the silicone material. In addition to sutures, other fixation means may be employed such as staples or a biocompatible adhesive, for example.

Various embodiments of the inventive devices may be entirely intravascular, entirely extravascular, or partially intravascular and partially extravascular. Furthermore, devices may reside wholly in or on arterial vasculature, wholly in or on venous vasculature, or in or on some combination of both. In some embodiments, for example, implantable devices may positioned within an artery or vein, while in other embodiments devices may be placed extravascularly, on the outside of an artery or vein. In yet other embodiments, one or more components of a device, such as electrodes, a controller or both, may be positioned outside the patient's body. In introducing and placing devices of the present invention, any suitable technique and access route may be employed. For example, in some embodiments an open surgical procedure may be used to place an implantable device. Alternatively, an implantable device may be placed within an artery or vein via a transvascular, intravenous approach. In still other embodiments, an implantable device may be introduced into vasculature via minimally invasive means, advanced to a treatment position through the vasculature, and then advanced outside the vasculature for placement on the outside of an artery or vein. For example, an implantable device may be introduced into and advanced through the venous vasculature, made to exit the wall of a vein, and placed at an extravascular site on an artery.

Figure 30:
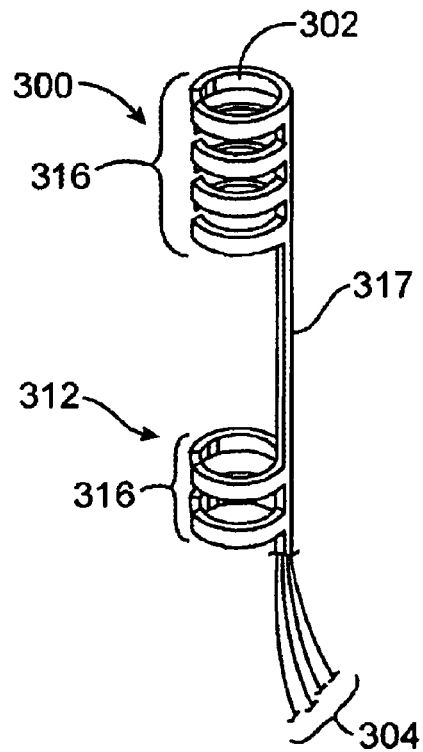
FIG. 30 is a schematic illustration of an alternative extravascular electrical activation device including a plurality of ribs and a spine.

Refer now to FIG. 30 which schematically illustrates an alternative extravascular electrical activation device 300 including one or more electrode ribs 316 interconnected by spine 317. Optionally, a support collar 312 having one or more (non-electrode) ribs 316 may be used to isolate the activation device 300 from movements and forces transmitted by the cables 304 proximal of the support collar 312.

The ribs 316 of the activation device 300 are sized to fit about the carotid anatomy, such as the internal carotid artery 19 adjacent the carotid sinus 20. Similarly, the ribs 316 of the support collar 312 may be sized to fit about the carotid anatomy, such as the common carotid artery 14 proximal of the carotid sinus 20. The ribs 316 may be separated, placed on a carotid artery, and closed thereabout to secure the device 300 to the carotid anatomy.

Each of the ribs 316 of the device 300 includes an electrode 302 on the inside surface thereof for electrical connection to carotid tissues. The ribs 316 provide insulative material around the electrodes 302, leaving only an inside portion exposed to the vascular wall. The electrodes 302 are coupled to the multi-channel cable 304 through spine 317. Spine 317 also acts as a tether to ribs 316 of the support collar 312, which do not include electrodes since their function is to provide support. The multi-channel electrode 302 functions discussed with reference to FIGS. 25-28 are equally applicable to this embodiment.

The ends of the ribs 316 may be connected (e.g., sutured) after being disposed about a carotid artery, or may remain open as shown. If the ends remain open, the ribs 316 may be formed of a relatively stiff material to ensure a mechanical lock around the carotid artery. For example, the ribs 316 may be formed of polyethylene, polypropylene, PTFE, or other similar insulative and biocompatible material. Alternatively, the ribs 316 may be formed of a metal such as stainless steel or a nickel titanium alloy, as long as the metallic material was electrically isolated from the electrodes 302. As a further alternative, the ribs 316 may comprise an insulative and biocompatible polymeric material with the structural integrity provided by metallic (e.g., stainless steel, nickel titanium alloy, etc.) reinforcement. In this latter alternative, the electrodes 302 may comprise the metallic reinforcement.

Figure 31:
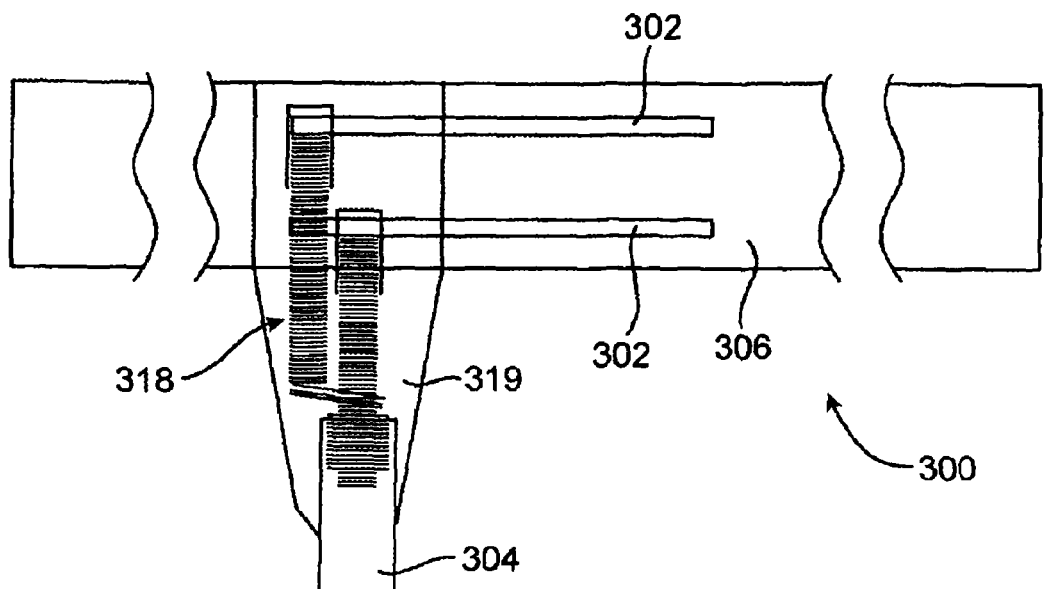
FIG. 31 is a schematic illustration of an electrode assembly for extravascular electrical activation embodiments.

Refer now to FIG. 31 which schematically illustrates a specific example of an electrode assembly for an extravascular electrical activation device 300. In this specific example, the base structure 306 comprises a silicone sheet having a length of 5.0 inches, a thickness of 0.007 inches, and a width of 0.312 inches. The electrodes 302 comprise platinum ribbon having a length of 0.47 inches, a thickness of 0.0005 inches, and a width of 0.040 inches. The electrodes 302 are adhesively connected to one side of the silicone sheet 306.

The electrodes 302 are connected to a modified bipolar endocardial pacing lead, available under the trade name CONIFIX from Innomedica (now BIOMEC Cardiovascular, Inc.), model number 501112. The proximal end of the cable 304 is connected to the control system 60 or driver 66 as described previously. The pacing lead is modified by removing the pacing electrode to form the cable body 304. The MP35 wires are extracted from the distal end thereof to form two coils 318 positioned side-by-side having a diameter of about 0.020 inches. The coils 318 are then attached to the electrodes utilizing 316 type stainless steel crimp terminals laser welded to one end of the platinum electrodes 302. The distal end of the cable 304 and the connection between the coils 318 and the ends of the electrodes 302 are encapsulated by silicone.

Figure 32:
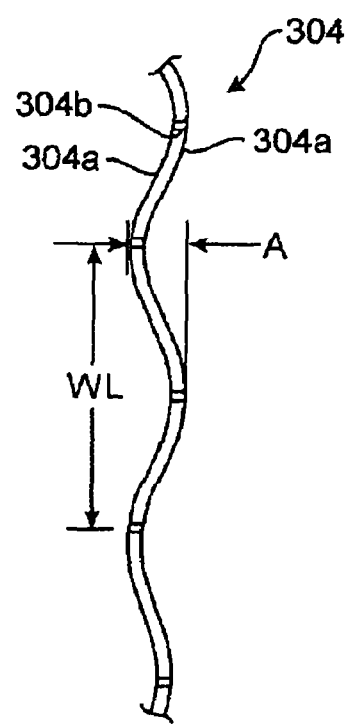
FIG. 32 is a schematic illustration of a fragment of an alternative cable for use with an electrode assembly such as shown in FIG. 31.

The cable 304 illustrated in FIG. 31 comprises a coaxial type cable including two coaxially disposed coil leads separated into two separate coils 318 for attachment to the electrodes 302. An alternative cable 304 construction is illustrated in FIG. 32. FIG. 32 illustrates an alternative cable body 304 which may be formed in a curvilinear shape such as a sinusoidal configuration, prior to implantation. The curvilinear configuration readily accommodates a change in distance between the device 300 and the control system 60 or the driver 66. Such a change in distance may be encountered during flexion and/or extension of the neck of the patient after implantation.

In this alternative embodiment, the cable body 304 may comprise two or more conductive wires 304a arranged coaxially or collinearly as shown. Each conductive wire 304a may comprise a multifilament structure of suitable conductive material such as stainless steel or MP35N. An insulative material may surround the wire conductors 304a individually and/or collectively. For purposes of illustration only, a pair of electrically conductive wires 304a having an insulative material surrounding each wire 304a individually is shown. The insulated wires 304a may be connected by a spacer 304b comprising, for example, an insulative material. An additional jacket of suitable insulative material may surround each of the conductors 304a. The insulative jacket may be formed to have the same curvilinear shape of the insulated wires 304a to help maintain the shape of the cable body 304 during implantation.

If a sinusoidal configuration is chosen for the curvilinear shape, the amplitude (A) may range from 1 mm to 10 mm, and preferably ranges from 2 mm to 3 mm. The wavelength (WL) of the sinusoid may range from 2 mm to 20 mm, and preferably ranges from 4 mm to 10 mm. The curvilinear or sinusoidal shape may be formed by a heat setting procedure utilizing a fixture which holds the cable 304 in the desired shape while the cable is exposed to heat. Sufficient heat is used to heat set the conductive wires 304a and/or the surrounding insulative material. After cooling, the cable 304 may be removed from the fixture, and the cable 304 retains the desired shape.

For any of the applications described above, it may be desirable to focus the output of the activation device 70 on portions of the carotid sinus 20 that are rich in baroreceptors 30, and minimize the output delivered to portions of the carotid sinus 20 with fewer or no baroreceptors 30. By focusing the output as such, baroreceptor activation may be maximized and the required device output (i.e., the required power or energy output of the baroreflex activation device 70) may be minimized. In particular, the ratio of baroreceptor activation to device output (A/O) may be maximized. In addition, by focusing the output as such, extraneous tissue activation may be minimized, power consumption (by the device 70) may minimize, and the degradation rate of baroreceptor responsiveness may be minimized.

It has been found that the A/O ratio is a function of the position of the baroreflex activation device. In particular, it has been found that the A/O ratio varies about the circumference of the carotid artery near the carotid sinus 20, perhaps due to variations in the location or density of baroreceptors. Although described herein with reference to the carotid sinus 20, it is also likely that the A/O ratio varies at all of the anatomical locations which contain baroreceptors as described previously.

In order to position the baroreflex activation device 70 to maximize the A/O ratio, a mapping technique may be employed. For example, the device 70 may be oriented in two or more different positions and/or at two or more different anatomical locations. More specifically, the output means of the device 70 may be disposed in two or more different positions/locations. The output means generally refers to the structure through which the stimulus is transferred to the tissue surrounding the baroreceptors. In electrical activation embodiments, for example, the output means may comprise electrodes.

At each position/location, the device 70 may be activated to a specified level, and the degree of baroreceptor activation may be observed or measured. The degree of baroreceptor activation may be inferentially determined by measuring changes in heart rate, blood pressure, and/or other physiological parameters indicative of baroreceptor activation. The resulting measurements may be used to generate an A/O ratio for each position/location. The A/O ratios for each location may be graphically plotted to generate a map. The A/O ratios may be compared, and the position/location having the most desirable A/O ratio may be selected for the device 70.

Figure 34:
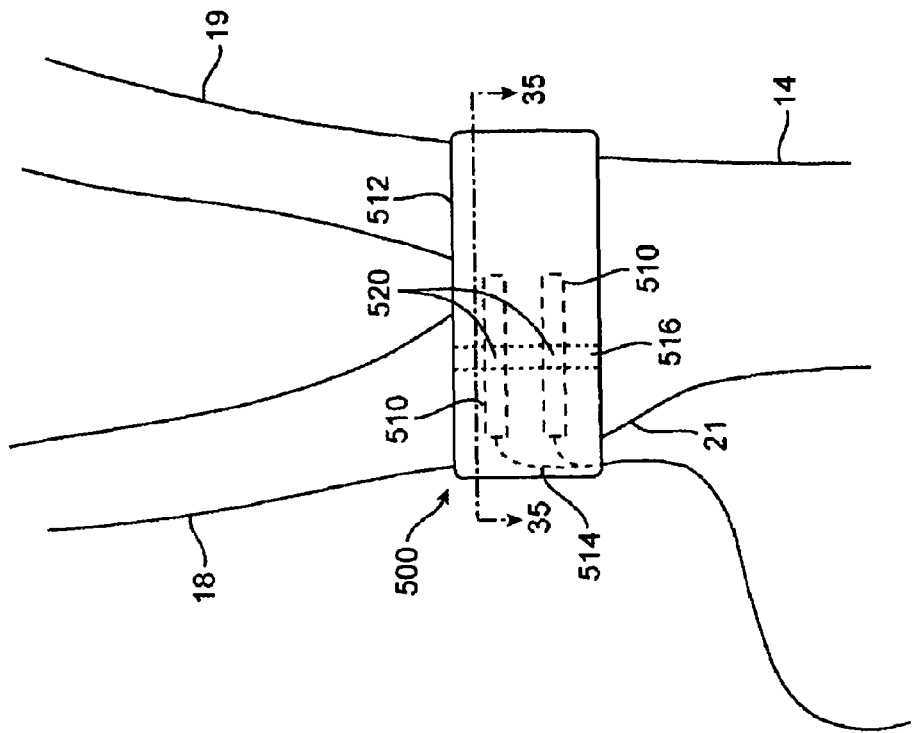
FIG. 34 is a schematic illustration of a baroreflex activation device disposed about the right carotid artery which may be used for mapping baroreceptors therein.
Figure 33:
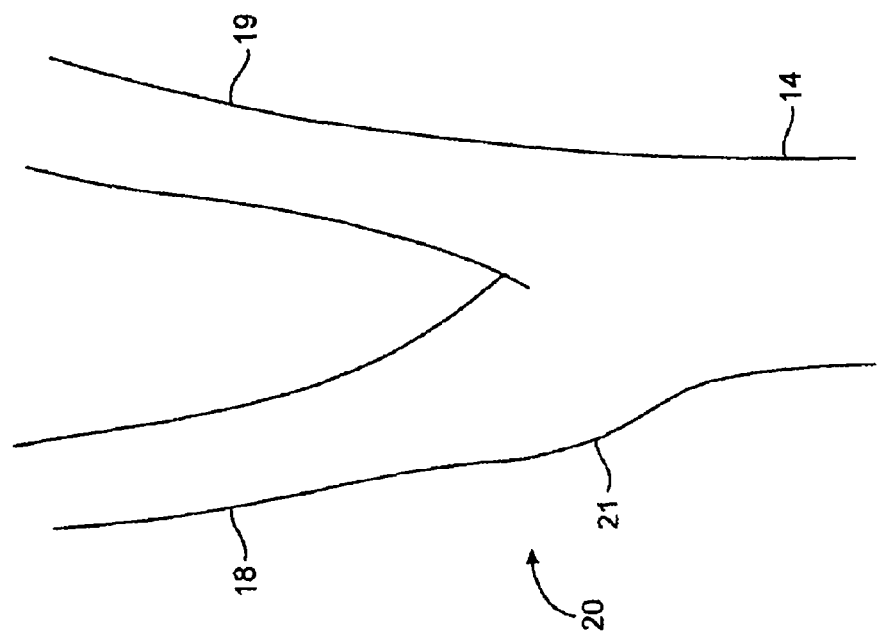
FIG. 33 is a schematic illustration of the right carotid artery showing a bulge in the vascular wall which is a landmark of the carotid sinus.
Figure 35:
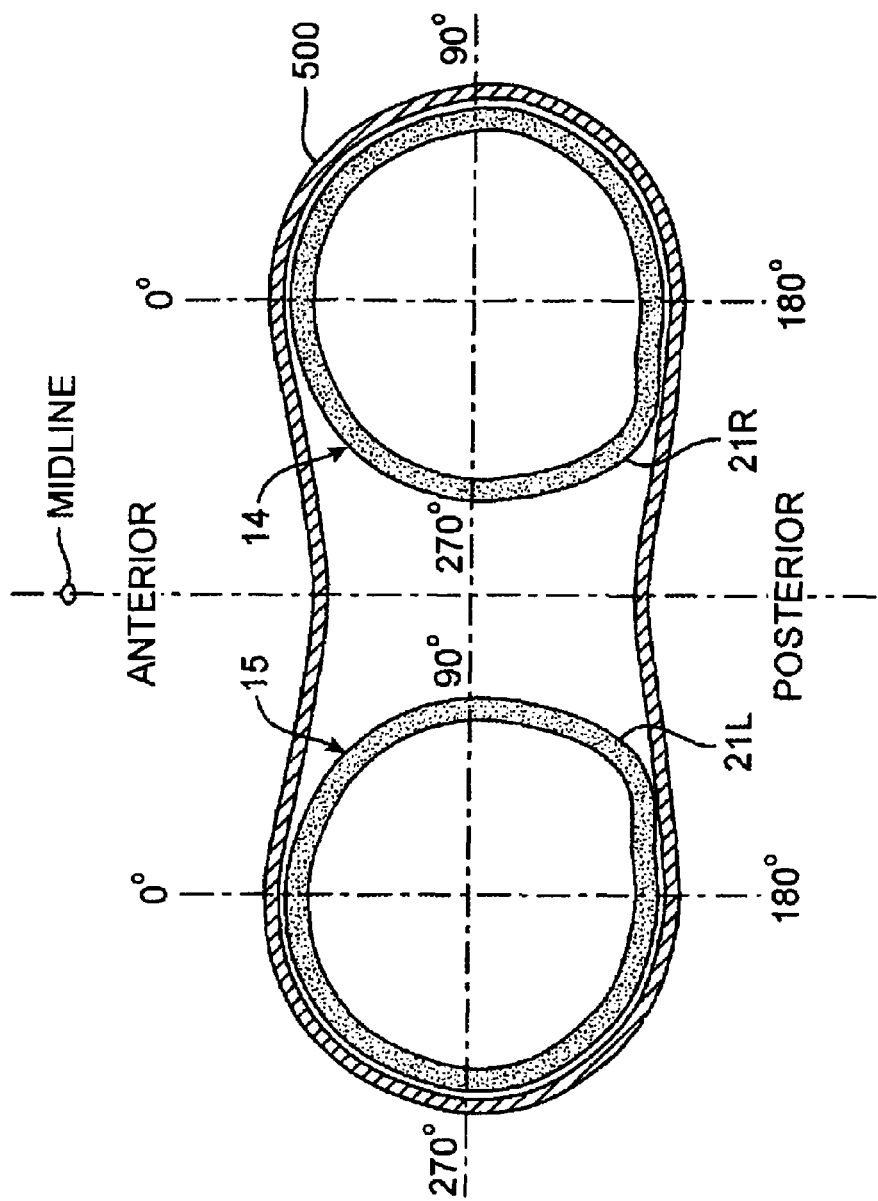
FIG. 35 is a schematic cross sectional view taken along line 35 in FIG. 34, showing a mapping coordinate system for the left and right carotid arteries.

To illustrate this mapping method, reference may be made to FIGS. 33-35. By way of example, not limitation, the mapping method is described with specific reference to the arteries, but the method is equally applicable to all anatomical structures containing baroreceptors. FIG. 33 shows the right carotid arteries including the common 14, internal 18, and external 19 carotid arteries. The carotid sinus 20 may be highlighted by a bulge 21, which typically extends from the common carotid artery 14 to the internal carotid artery 18 near the bifurcation. The carotid sinus 20 contains a significant number of baroreceptors, the number and density of which may vary around the circumference and along the length of the sinus 20. As such, it is desirable to determine the optimal position for the baroreflex activation device 70, both in terms of circumferential and longitudinal position.

The mapping method described herein is equally applicable to all baroreflex activation devices 70, regardless of the mode of activation (mechanical, electrical, thermal, chemical, biological, or other means) and regardless of their in vivo position (intravascular, extravascular, intramural). By way of example, not limitation, the device 70 is shown in FIG. 34 as an extravascular electrical device 500 having two electrodes 520 which contact the outside wall of the carotid sinus 20 at two different locations. The device 500 includes a molded silicone housing 512. The housing 512 carries two metal strips 510 which are separated by approximately 4 mm and are formed of platinum ribbon (0.040 in. wide by 0.0005 in. thick by 10 mm long). The metal strips 510 are insulated by the housing 512 except at the 1 mm wide exposed area 516. The metal strips 510 in the exposed area 516 define two electrodes 520 that contact the outside surface of the carotid artery. Leads 514 couple the metal strips 510 to cable 502 which is connected to a control system 60 as described previously with reference to FIG. 3.

With the device 500 disposed about the carotid arteries as shown in FIG. 34, the device 500 may be activated to produce an output signal from the electrodes 520, which in turn activates the baroreceptors, as evidenced by a change in heart rate and/or blood pressure. The position and/or location of the electrodes 520 is recorded along with the amount of output (e.g., power) and the corresponding change in the heart rate, blood pressure and/or other physiological parameters indicative of baroreceptor activation. From this information, the A/O ratio may be determined for this particular position/location.

The electrodes 520 of the device 500 are then oriented in a different position (e.g., rotated) and/or placed at a different anatomical location, and the same measurements are made. These steps are repeated to collect the desired amount of data, which may be graphically plotted to generate a map to determine an optimal position/location. The A/O ratios may be compared, and the position/location having the most desirable A/O ratio may be selected for the device 500. As an alternative to device 500, a hand held probe or similar device incorporating electrodes 520 may be used to permit easier manipulation and quicker changes between different locations/positions.

To keep track of different circumferential positions around the carotid arteries, a coordinate system may be used as shown in FIG. 35. FIG. 35 is a schematic cross-sectional view taken along line 35-35 in FIG. 34, showing a mapping coordinate system for the left carotid artery 15 and right carotid artery 14. In this coordinate system, the left carotid artery 15 and right carotid artery 14 are viewed in cross-section looking from the head of the patient toward the feet, with 0.degree. positioned anteriorly and 180.degree. positioned posteriorly. The center or apex of the left bulge 21 L which identifies the left carotid sinus 20L is typically located at 110.degree. to 160.degree. The center or apex of the right bulge 21 R which identifies the right carotid sinus 20R is typically located at 200.degree. to 250.degree. This coordinate system is particularly useful for mapping the circumference of the carotid arteries, in addition to other arteries and tubular organs.

Although the above description provides a complete and accurate representation of the invention, the present invention may be manifested in a variety of forms other than the specific embodiments described and contemplated herein. Accordingly, departures in form and detail may be made without departing from the scope and spirit of the present invention as described in the appended claims.

The invention claimed is:

1. A system for implantation of a medical lead configured to deliver electrical stimulation to nerve tissue located adjacent a blood vessel, the system comprising:
an electrode;
a means for delivering the electrode through a lumen of the blood vessel;
a means for determining a suitable implant location for the electrode proximate the nerve tissue; and
a means for deploying the electrode through a wall of the blood vessel, so as to position the electrode outside of the blood vessel proximate the nerve tissue,
wherein the means for determining is configured to detect one or more physiological signals from the patient in response to a baroreceptor activation signal delivered through the electrode.

2. The system of claim 1, wherein the means for determining comprises a physiological sensor.

3. The system of claim 2, wherein the physiological sensor comprises one of a sense electrode, pressure sensor, pressure transducer, ultrasound sensor, motion sensor, acoustic sensor, optical sensor, blood oxygen sensor, activity sensor, posture state sensor, respiration sensor, or temperature sensor.

4. The system of claim 1, wherein the physiological sensor is configured to detect one or more of neurological activity, electrocardiogram, heart rate, blood pressure, blood flow, blood oxygen content, cardiac output, respiration, nerve signals.

5. The system of claim 1, wherein the means for deploying is configured to temporarily deploy and retract the electrode so as to deliver the baroreceptor activation signal from multiple locations prior to deploying the electrode.

6. The system of claim 1, further comprising:
a lead connected to the electrode and configured to be connectable to a pulse generator.

7. The system of claim 1, further comprising a means for anchoring the electrode outside of the blood vessel adjacent the nerve tissue.

8. The method of claim 1, wherein the blood vessel is selected from the group consisting of: a carotid sinus, an aortic arch, a common carotid artery, a subclavian artery, a brachiocephalic artery, pulmonary artery, pulmonary vein, jugular vein, femoral artery, femoral vein, and a heart.

9. A system for implantation of a medical lead configured to deliver electrical stimulation to nerve tissue located adjacent a blood vessel, the system comprising:
an electrode;
a means for delivering the electrode through a lumen of the blood vessel;
a means for determining a suitable implant location for the electrode proximate the nerve tissue; and
a means for deploying the electrode through a wall of the blood vessel, so as to position the electrode outside of the blood vessel proximate the nerve tissue,
wherein the nerve tissue comprises a baroreceptor disposed in the wall of the blood vessel, or a carotid sinus nerve.

10. The method of claim 9, wherein the blood vessel is selected from the group consisting of: a carotid sinus, an aortic arch, a common carotid artery, a subclavian artery, a brachiocephalic artery, pulmonary artery, pulmonary vein, jugular vein, femoral artery, femoral vein, and a heart.

11. A method comprising:
delivering a lead through a lumen of a blood vessel to a location proximate a target nerve tissue site outside the blood vessel, the lead including an electrode at a distal end;
determining a suitable implant location for the electrode;
advancing the lead from within the lumen such that the electrode passes through a wall of the blood vessel; and
determining a suitable implant location for the electrode, proximate the nerve tissue,
wherein determining a suitable implant location for the electrode comprises a mapping procedure including:
delivering a baroreceptor activation signal through the electrode from a plurality of locations within the blood vessel; and
measuring a patient response to each baroreceptor activation signal.

12. The method of claim 11, further comprising temporarily deploying the electrode toward the nerve tissue at each location.

13. The method of claim 11, further comprising anchoring the electrode outside of the blood vessel adjacent the nerve tissue.

14. The method of claim 11, wherein the blood vessel is selected from the group consisting of: a carotid sinus, an aortic arch, a common carotid artery, a subclavian artery, a brachiocephalic artery, pulmonary artery, pulmonary vein, jugular vein, femoral artery, femoral vein, and a heart.

15. A method comprising:
   delivering a lead through a lumen of a blood vessel to a location proximate a target nerve tissue site outside the blood vessel, the lead including an electrode at a distal end;
   determining a suitable implant location for the electrode; and
   advancing the lead from within the lumen such that the electrode passes through a wall of the blood vessel,
   wherein the nerve tissue comprises one of a baroreceptor disposed in the wall of the blood vessel, or a carotid sinus nerve.

16. The method of claim 15, further comprising:
   determining a suitable implant location for the electrode, proximate the nerve tissue.

* * * * *